(12) United States Patent
Cho et al.

(10) Patent No.: US 9,090,642 B2
(45) Date of Patent: Jul. 28, 2015

(54) METHODS FOR THE PREPARATION OF DIASTEROMERICALLY PURE PHOSPHORAMIDATE PRODRUGS

(75) Inventors: Aesop Cho, Mountain View, CA (US); Michael O'Neil Hanrahan Clarke, Redwood City, CA (US); Scott Alan Wolckenhauer, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 186 days.

(21) Appl. No.: 13/813,886

(22) PCT Filed: Jul. 19, 2011

(86) PCT No.: PCT/US2011/044581
§ 371 (c)(1),
(2), (4) Date: Jun. 25, 2013

(87) PCT Pub. No.: WO2012/012465
PCT Pub. Date: Jan. 26, 2012

(65) Prior Publication Data
US 2013/0281686 A1    Oct. 24, 2013

Related U.S. Application Data

(60) Provisional application No. 61/365,621, filed on Jul. 19, 2010.

(51) Int. Cl.
| | |
|---|---|
| C07H 21/00 | (2006.01) |
| C07H 1/00 | (2006.01) |
| A61K 31/7052 | (2006.01) |
| A61K 31/7042 | (2006.01) |
| C07H 19/02 | (2006.01) |
| C07H 19/10 | (2006.01) |
| C07H 19/20 | (2006.01) |
| C07F 9/6558 | (2006.01) |
| C07F 9/6561 | (2006.01) |
| C07F 9/24 | (2006.01) |

(52) U.S. Cl.
CPC .............. *C07H 1/00* (2013.01); *A61K 31/7042* (2013.01); *A61K 31/7052* (2013.01); *C07F 9/2458* (2013.01); *C07F 9/6561* (2013.01); *C07F 9/65586* (2013.01); *C07F 9/65616* (2013.01); *C07H 19/02* (2013.01); *C07H 19/10* (2013.01); *C07H 19/20* (2013.01)

(58) Field of Classification Search
None
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,663,159 A | 9/1997 | Starrett, Jr. et al. |
| 5,792,756 A | 8/1998 | Starrett, Jr. et al. |
| 6,312,662 B1 | 11/2001 | Erion et al. |
| 6,476,030 B1 | 11/2002 | Carling et al. |
| 6,656,915 B1 | 12/2003 | Bantia et al. |
| 6,909,011 B2 | 6/2005 | Skranc et al. |
| 7,105,493 B2 | 9/2006 | Sommadossi et al. |
| 7,125,855 B2 | 10/2006 | Bhat et al. |
| 7,176,203 B2 | 2/2007 | Chambers et al. |
| 7,268,119 B2 | 9/2007 | Cook et al. |
| 7,285,658 B2 | 10/2007 | Cook et al. |
| 7,368,437 B1 | 5/2008 | Bojack et al. |
| 7,429,571 B2 | 9/2008 | Chand et al. |

(Continued)

FOREIGN PATENT DOCUMENTS

| | | |
|---|---|---|
| CA | 2367921 C | 7/2009 |
| CN | 1443189 A | 9/2003 |

(Continued)

OTHER PUBLICATIONS

Shekunov et al. Journal of Crystal Growth (2000), vol. 211, pp. 122-136.*
Colacino, E. et al., "Synthesis and Biological Evaluation of Some 5-Nitro- and 5-Amino Derivatives of 2'-Deoxycytidine, 2', 3'-Dideoxyuridine, and 2', 3' -Dideoxycytidine," Nucleoside, Nucleotides & Nucleic Acids, vol. 22, No. 11, pp. 2013-2026 (2003).
El Safadi, Y. et al., "5-Modified-2'-dU and 2'-dC as Mutagenic Anti HIV-1 Proliferation Agents: Synthesis and Activity," J. Med. Chem., vol. 53, No. 4, pp. 1534-1545 (2010).

(Continued)

*Primary Examiner* — Patrick Lewis

(57) ABSTRACT

Provided are methods and intermediates for preparing diastereomerically pure phosphoramidate prodrugs of nucleosides of Formulas Ia and Ib:

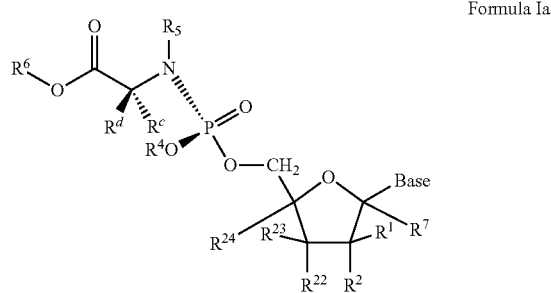

Formula Ia

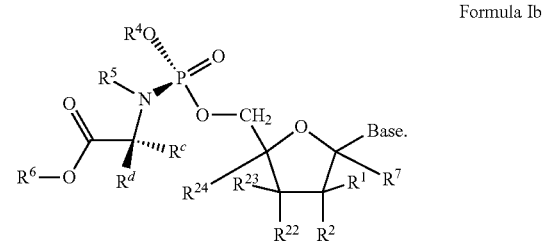

Formula Ib

The compounds of Formula Ia and Ib are useful for the treatment Hepatitis C infections.

34 Claims, No Drawings

(56) References Cited

U.S. PATENT DOCUMENTS

| | | | |
|---|---|---|---|
| 7,514,410 | B2 | 4/2009 | Babu et al. |
| 7,560,434 | B2 | 7/2009 | Babu et al. |
| 7,598,230 | B2 | 10/2009 | Cook et al. |
| 7,608,597 | B2 | 10/2009 | Sommadossi et al. |
| 7,713,941 | B2 | 5/2010 | Cook et al. |
| 7,807,653 | B2 | 10/2010 | Cook et al. |
| 7,842,672 | B2 | 11/2010 | Boojamra et al. |
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,071,568 | B2 | 12/2011 | Narjes et al. |
| 8,119,607 | B2 | 2/2012 | Francom et al. |
| 8,242,085 | B2 | 8/2012 | Babu et al. |
| 8,318,682 | B2 | 11/2012 | Butler et al. |
| 8,415,308 | B2 | 4/2013 | Cho et al. |
| 8,455,451 | B2 | 6/2013 | Cho et al. |
| 8,853,171 | B2 | 10/2014 | Butler et al. |
| 2003/0050229 | A1 | 3/2003 | Sommadossi et al. |
| 2004/0006002 | A1 | 1/2004 | Sommadossi et al. |
| 2004/0023901 | A1 | 2/2004 | Cook et al. |
| 2004/0063658 | A1 | 4/2004 | Roberts et al. |
| 2004/0067901 | A1 | 4/2004 | Bhat et al. |
| 2004/0138170 | A1 | 7/2004 | Montgomery et al. |
| 2005/0187180 | A1 | 8/2005 | Loeb et al. |
| 2005/0215513 | A1 | 9/2005 | Boojamra et al. |
| 2005/0250728 | A1 | 11/2005 | Bantia et al. |
| 2006/0058303 | A1 | 3/2006 | Chambers et al. |
| 2006/0241064 | A1 | 10/2006 | Roberts et al. |
| 2008/0107628 | A1 | 5/2008 | Boojamra et al. |
| 2008/0161324 | A1 | 7/2008 | Johansen et al. |
| 2008/0280842 | A1 | 11/2008 | Maccoss et al. |
| 2009/0004138 | A1 | 1/2009 | Francom et al. |
| 2009/0221524 | A1 | 9/2009 | Kotra et al. |
| 2009/0233879 | A1 | 9/2009 | Reddy et al. |
| 2009/0317361 | A1 | 12/2009 | Cho et al. |
| 2010/0015094 | A1 | 1/2010 | Babu et al. |
| 2010/0016251 | A1 | 1/2010 | Sofia et al. |
| 2010/0021425 | A1 | 1/2010 | Butler et al. |
| 2010/0035835 | A1 | 2/2010 | Narjes et al. |
| 2010/0035836 | A1 | 2/2010 | Francom et al. |
| 2010/0203015 | A1 | 8/2010 | Butler et al. |
| 2010/0234584 | A1 | 9/2010 | Chang |
| 2010/0291031 | A2 | 11/2010 | Francom et al. |
| 2010/0298257 | A1 | 11/2010 | Ross et al. |
| 2011/0070194 | A1 | 3/2011 | Cho et al. |
| 2011/0230654 | A1 | 9/2011 | Butler et al. |
| 2011/0257122 | A1 | 10/2011 | Sofia et al. |
| 2011/0293563 | A1 | 12/2011 | Butler et al. |
| 2012/0009147 | A1 | 1/2012 | Cho et al. |
| 2012/0020921 | A1 | 1/2012 | Cho et al. |
| 2012/0027752 | A1 | 2/2012 | Mackman et al. |
| 2012/0107274 | A1 | 5/2012 | Clarke et al. |
| 2013/0034521 | A1 | 2/2013 | Butler et al. |
| 2013/0344028 | A2 | 12/2013 | Butler et al. |

FOREIGN PATENT DOCUMENTS

| | | |
|---|---|---|
| CN | 1498221 A | 5/2004 |
| CN | 1852915 A | 10/2006 |
| CN | 1291994 | 12/2006 |
| CN | 101043893 A | 9/2007 |
| CN | 101611046 A | 12/2009 |
| CN | 102906102 A | 1/2013 |
| EA | 201071170 | 8/2011 |
| EA | 201171417 | 5/2012 |
| EA | 201200525 | 9/2012 |
| EP | 2 396 340 B1 | 12/2013 |
| JP | 41017629 B | 10/1966 |
| JP | 2004-520367 | 7/2004 |
| JP | 2008-502685 | 1/2008 |
| JP | 2008-518934 | 6/2008 |
| TW | 1401084 B | 7/2013 |
| WO | 91/19721 A1 | 12/1991 |
| WO | 00/56734 A1 | 9/2000 |
| WO | 01/32153 A2 | 5/2001 |
| WO | 01/60315 A2 | 8/2001 |
| WO | 01/90121 A2 | 11/2001 |
| WO | WO 02/08241 A2 | 1/2002 |
| WO | 02/18404 A2 | 3/2002 |
| WO | 02/32920 A2 | 4/2002 |
| WO | 02/057287 A2 | 7/2002 |
| WO | 02/057425 A2 | 7/2002 |
| WO | 03/093272 A1 | 11/2003 |
| WO | 03/093273 A1 | 11/2003 |
| WO | 03/100009 A2 | 12/2003 |
| WO | 2004/046331 A2 | 6/2004 |
| WO | 2005/009418 A2 | 2/2005 |
| WO | 2005/123087 A2 | 12/2005 |
| WO | 2006/031725 A2 | 3/2006 |
| WO | 2006/050161 A2 | 5/2006 |
| WO | 2006/065335 A2 | 6/2006 |
| WO | 2006/121820 A1 | 11/2006 |
| WO | 2007/027248 A2 | 3/2007 |
| WO | 2007/056170 A2 | 5/2007 |
| WO | 2007/064883 A2 | 6/2007 |
| WO | 2007/064931 A2 | 6/2007 |
| WO | WO 2007/065289 A2 | 6/2007 |
| WO | 2007/097991 A2 | 8/2007 |
| WO | WO 2007/135134 A1 | 11/2007 |
| WO | 2008/005542 A2 | 1/2008 |
| WO | 2008/079206 A1 | 7/2008 |
| WO | 2008/082601 A2 | 7/2008 |
| WO | 2008/085508 A2 | 7/2008 |
| WO | 2008/089105 A2 | 7/2008 |
| WO | 2008/116064 A2 | 9/2008 |
| WO | 2008/121634 A2 | 10/2008 |
| WO | 2008/141079 A1 | 11/2008 |
| WO | 2009/009951 A1 | 1/2009 |
| WO | 2009/131926 A1 | 10/2009 |
| WO | 2009/132123 A1 | 10/2009 |
| WO | 2009/132135 A1 | 10/2009 |
| WO | 2010/002877 A2 | 1/2010 |
| WO | 2010/036407 A2 | 4/2010 |
| WO | WO 2010/093608 A1 | 8/2010 |
| WO | WO 2010/099458 A1 | 9/2010 |
| WO | WO 2010/111381 A2 | 9/2010 |
| WO | 2010/135569 A1 | 11/2010 |
| WO | 2011/035231 A1 | 3/2011 |
| WO | 2011/035250 A1 | 3/2011 |
| WO | 2011/123672 A1 | 10/2011 |
| WO | WO 2011/123645 A2 | 10/2011 |
| WO | WO 2011/150288 A1 | 12/2011 |
| WO | WO 2012/012465 A1 | 1/2012 |
| WO | WO 2012/012776 A1 | 1/2012 |
| WO | WO 2012/039787 A1 | 3/2012 |
| WO | WO 2012/039791 A1 | 3/2012 |
| WO | WO 2012/051570 A1 | 4/2012 |

OTHER PUBLICATIONS

Harki, D. et al., "Synthesis and Antiviral Activity of 5-Substituted Cytidine Analogues: Identification of Potent Inhibitor of Viral RNA-Dependent RNA Polymerases," J. Med. Chem., vol. 49, No. 21, pp. 6166-6169 (2006).

Jasko, M. et al., "5'-Phosphonates of Ribonucleosides and 2'-Deoxyribonucleosides: Synthesis and Antiviral Activity," Nucleosides and Nucleotides, vol. 12, No. 8, pp. 879-893 (1993).

Meppen, M. et al., "Medi-404—A Prodrug Approach for the Treatment of HCV Infection," Abstracts of Papers, 236th ACS National Meeting, Philadelphia, PA, United States, Aug. 17-21, 2008.

Poduch, E. et al., "Design of Inhibitors of Orotidine Monophosphate Decarboxylase Using Bioisosteric Replacement and Determination of Inhibition Kinetics," J. Med. Chem., vol. 49, No. 16, pp. 4937-4945 (2006).

Srivastav, N. et al., "Antiviral Activity of Various 1-(2'-Deoxy-β-D-lyxofuranosyl), 1-(2'-Fluoro-β-D-xylofuranosyl),1-(3'- Fluoro-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," J. Med. Chem., vol. 53, No. 19, pp. 7156-7166 (2010).

(56) References Cited

OTHER PUBLICATIONS

Tapia, N. et al., "Combination of a Mutagenic Agent with a Reverse Transcriptase Inhibitor Results in Systematic Inhibition of HIV-1 Infection," Virology, vol. 338, pp. 1-8 (2005).
Vaghefi, M. et al.,"Synthesis and Antiviral Activity of Certain Nucleoside 5'-Phosphonoformate Derivatives," J. Med. Chem., vol. 29, pp. 1389-1393 (1986).
Arimilli, MN et al. (1997) "Synthesis, in vitro biological evaluation and oral bioavailability of 9-[2-(phosphonomethoxy)propyl]adenine (PMPA) prodrugs", Antiviral Chemistry & Chemotherapy, vol. 8(6), p. 557-564.
Benzaria, S. et al. (1996) "Synthesis in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability", Journal of Medicinal Chemistry, vol. 39, pp. 4958-4965.
Bio, M. et al. (2004) "Practical Synthesis of a Potent Hepatitis C Virus RNA Replication Inhibitor", Journal of Organic Chemistry, vol. 69, pp. 6257-6266.
Bobeck D.R. et al. (2010) "Advances in nucleoside monophosphate prodrugs as anti-HCV agents", Antiviral Therapy, vol. 15, pp. 935-950.
Bojack G. et al. (2001), "Design and Synthesis of Inhibitors of Adenosine and AMP Deaminases", Organic Letters, vol. 3(6), pp. 839-842.
International Preliminary Report on Patentability and Written Opinion for PCT/US2009/041432, mailed Oct. 26, 2010 (7 pages).
Calisher, C. et al. (1989) "Antigenic Relationships between Flaviviruses as Determined by Cross-neutralization Tests with Polyclonal Antisera", Journal of General Virology, vol. 70, pp. 37-43.
De Clercq, E. (2001) "Antiviral drugs: current state of the art", Journal of Clinical Virology, vol. 22, pp. 73-89.
De Clercq, E. (2001) "Molecular Targets for Antiviral Agents" The Journal of Pharmacology and Experimental Therapeutics, vol. 297(1), pp. 1-10.
De Francesco, R. et al. (2003) "Approaching a new era for hepatitis C virus therapy: inhibitors of the NS3-4A serine protease and the NS5B RNA-dependent RNA polymerase", Antiviral Research, vol. 58, pp. 1-16.
De Lombaert, S. et al. (1994) "N—Phosphonomethyl Dipeptides and Their Phosphonate Prodrugs, a New Generation of Neutral Endopeptidase (NEP, EC 3.4.24.11) Inhibitors", Journal of Medicinal Chemistry, vol. 37, pp. 498-511.
Di Bisceglie, A. et al. (Oct. 1999) "The Unmet Challenges of Hepatitis C", Scientific American, Inc. pp. 80-85.
Dolzhenko, A.V. et al. (2008) "Pyrazolo[1,5-a][1,3,5]Triazines(5-AZA-9-Deazapurines):Synthesis and Biological Activity", Heterocycles, vol. 75, No. 7, pp. 1575-1622.
Dudfield, P. et al. (1999) "Synthesis of C- ribosyl imidazo[2,1-f][1,2,4]triazines as inhibitors of adenosine and AMP deaminases," J. Chem. Soc, Perkin Trans. 1, pp. 2929-2936.
Dudfield, P.J. et al. (1999) "Synthesis of C-ribosyl 1,2,4-triazolo[3,4-f][1,2,4]triazines as inhibitors of adenosine and AMP deaminases", J. Chem. Soc., Perkin Trans. 1, pp. 2937-2942.
Dymock, B. et al. (2000) "Novel approaches to the treatment of hepatits C virus infection", Antiviral Chemistry & Chemotherapy, vol. 11, pp. 79-96.
Farquhar, D. et al. (1983), "Biologically Reversible Phosphate-Protective Groups", Journal of Pharmaceutical Sciences, vol. 72, No. 3, pp. 324-325.
Gleeson, P.M. et al. (2003) "Prediction of the potency of inhibitors of adenosine deaminase by QM/MM calculations," Chem. Commun., pp. 2180-2181.
Gordon, C.P. et al. (2005) "Control of Hepatitis C: A Medicinal Chemistry Perspective", Journal of Medicinal Chemistry, vol. 48, No. 1, pp. 1-20.
Haraguchi, K. et al. (1995) "Stereoselective Synthesis of 1'-C-Branched Uracil Nucleosides From Uridine," Nucleosides & Nucleotides, vol. 14, Nos. 3-5, pp. 417-420.

Hayashi, M. et al. (1992) "C-Nucleosides, A Synthesis of 2-Substituted 7-((β-D-Ribofuranosyl)-Pyrrolo[2,1-f]-1,2,4-Triazines. A New Type of "Purine Like" C-Nucleoside," Heterocycles, vol. 34, No. 3, pp. 569-574.
Hecker, S.J.et al. (2007) "Liver Targeted Prodrugs of 2'-C—Methyladenosine for Therapy of Hepatitis C Virus Infection", Journal of Medicinal Chemistry, vol. 50, pp. 3891-3896.
International Search Report for PCT/US2009/041432 mailed on Aug. 11, 2009 (5 pages).
International Search Report for PCT/US2009/041447, mailed on Aug. 7, 2009 (5 pages).
International Search Report for PCT/US2010/049471, mailed Nov. 18, 2010 (5 pages).
International Search Report for PCT/US2010/049508, mailed Nov. 5, 2010 (4 pages).
Itoh, Y. et al. (1995) "Divergent and Stereocontrolled Approach to the Synthesis of Uracil Nucleosides Branched at the Anomeric Position," J. Org. Chem., vol. 60, pp. 656-662.
Khamnei, S. et al. (1996) "Neighboring Group Catalysis in the Design of Nucleotide Prodrugs", Journal of Medicinal Chemistry, vol. 39, pp. 4109-4115.
Knutsen, L. et al. (1984) "Synthesis of Imidazo-fused Bridgehead-nitrogen C-Nucleosides via Dehydrative Coupling Reactions of 2,5-Anhydro-3,4,6-tri-O-benzoyl-D- allonic Acid," J. Chem. Soc. Perkin Trans. I, pp. 229-238.
Knutsen, L. et al. (1985) "Synthesis of Imidazo-fused Bridgehead-nitrogen C -Nucleosides: Coupling-Elimination Reactions of 2,5-Anhydro-3,4,6-tri-O-benzoyl-D- allonic Acid," J. Chem. Soc. Perkin Trans. I, pp. 621-630.
Kobe, B. et al. (1992) "Use of distance geometry approach for the in vitro antiviral activity evaluation of N-bridgehead C-nucleosides", European Journal of Medicinal Chemistry, vol. 27, pp. 259-266.
McGuigan, C. et al. (1993) "Intracellular Delivery of Bioactive AZT Nucleotides by Aryl Phosphate Derivatives of AZT", Journal of Medicinal Chemistry, vol. 36, pp. 1048-1052.
Mitchell, A.G. et al. (1992) "Bioreversible Protection for the Phospho Group: Bioactivation of the Di(4-acyloxybenzyl) and Mono (4-acyloxybenzyl) Phosphoesters of Methylphosphonate and Phosphonoacetate", J. Chem. Soc. Perkin Trans. 1, pp. 2345-2353.
Mitchell, W. L. et al. (1984) "Synthesis of C-Nucleoside Isosteres of 9-(2- Hydroxyethoxymethyl)guanine (Acyclovir) [1]", Journal of Heterocyclic Chemistry, vol. 21, pp. 697-699.
Moennig, V. et al. (1992) "The Pestiviruses", Advances in Virus Research, vol. 41, pp. 53-98.
Moradpour, D. et al. (2007) "Replication of hepatitis C virus", Nature Reviews Microbiology, vol. 5, pp. 453-463.
Nishimura, N. et al. (2001) "Synthesis of pyrrolo[2,1-f][1,2,4]triazine C-nucleosides. Isosteres of sangivamycin, tubercidin, and toyocamycin," Carbohydrate Research, vol. 331, pp. 77-82.
Otter, B. et al. (1996) "Conformational Properties of Purine-Like C-Nucleosides", Nucleosides & Nucleotides, vol. 15, Nos. 1-3, pp. 793-807.
Patil, S. et al. (1994) "4-Aza-7,9-Dideazaadenosine, a New Cytotoxic Synthetic C-Nucleoside Analogue of Adenosine," Tetrahedron Letters, vol. 35, No. 30, pp. 5339-5342.
Patil, S.A. et al. (1994) "Synthesis of Pyrrolo[2,1-f][1,2,4]triazine Congeners of Nucleic Acid Purines via the N-Amination of 2-Substituted Pyrroles[1]", Journal of Heterocyclic Chemistry, vol. 31, pp. 781-786.
Puech, F. et al. (1993) "Intracellular delivery of nucleoside monophosphates through a reductase-mediated activiation process", Antiviral Research, vol. 22, pp. 155-174.
Ramasamy, K. et al. (1986) "Synthesis and Antitumor Activity of Certain 3-β-D-Ribofuranosyl-1,2,4-triazolo[3,4-f]-1,2,4-triazines Related to Formycin Prepared via Ring Closure of a 1,2,4-Triazine Precursor", Journal of Medicinal Chemistry, vol. 29, pp. 2231-2235.
Reddy, K.R. et al. (2005) "Stereoselective synthesis of nucleoside monophosphate HepDirect™ Prodrugs", Tetrahedron Letters, vol. 46, pp. 4321-4324.
Schul, W. et al. (2007) "A Dengue Fever Viremia Model in Mice Shows Reduction in Viral Replication and Suppression of the Inflam-

(56) References Cited

OTHER PUBLICATIONS matory Response after Treatment with Antiviral Drugs", Journal of Infectious Diseases, vol. 195, pp. 665-674.
Scott, L. J. et al. (2002) "Interferon-α-2b Plus Ribavirin", Drugs, vol. 62, No. 3, pp. 507-556.
International Preliminary Report on Patentability and Written Opinion for PCT/US2010/049471, mailed Mar. 27, 2012 (7 pages).
International Preliminary Report on Patentability and Written Opinion for PCT/US2010/049508, mailed Mar. 27, 2012 (6 pages).
Yoshimura, Y. et al. (1996) "Synthesis and Biological Evaluation of 1'-C-Cyano-Pyrimidine Nucleosides," Nucleosides & Nucleotides, vol. 15, Nos. 1-3, pp. 305-324.
Boyer, N. et al. (2000) "Pathogenesis, diagnosis and management of hepatitis C", Journal of Hepatology, vol. 32, Suppl. 1, pp. 98-112.
Ali, H. M. et al., "Quantitative Structure-Activity Relationships (QSAR) of Two Series of O-Aryl or N-Aryl O-Ethyl Phosphoramidate and Phosphorodiamidate Fungicides Incorporating Amino Acid Ethyl Esters", Bulletin of Environmental Contamination and Toxicology, vol. 65, No. 4, pp. 415-420 (2000).
Gardelli, C., et al., "Phosphoramidate Prodrugs of 2'-C-Methylcytidine for Therapy of Hepatitis C Virus Infection," J Med. Chem., vol. 52, No. 17, pp. 5394-5407 (2009).
International Preliminary Report on Patentability and Written Opinion of the International Searching Authority in International Application No. PCT/US2011/038253, dated Dec. 4, 2012 (6 pages).
International Search Report in International Application No. PCT/US2011/038253, dated Jul. 29, 2011 (4 pages).
International Search Report in International Application No. PCT/US2011/044581, dated Jul. 11, 2011 (4 pages).
International Preliminary Report on Patentability and Written Opinion of the International Searching Authority in International Application No. PCT/US2011/044581, dated Jan. 22, 2013 (7 pages).
Perrone, P., et al., "Application of the Phosphoramidate ProTide Approach to 4'-Azidouridine Confers Sub-micromolar Potency versus Hepatitis C Virus on an Inactive Nucleoside," J. Med. Chem., vol. 50, No. 8, pp. 1840-1849 (2007).
Silverman, R.B., "The Organic Chemistry of Drug Design and Drug Action," 2nd Edition, Elsevier Academic Press, pp. 29-34 (2004).
Examiner-Initiated Interview Summary dated Nov. 3, 2014 for U.S. Appl. No. 12/886,248 (10 pages).
Final Rejection mailed Nov. 4, 2014 for U.S. Appl. No. 13/189,373 (11 pages).
Resolution No. 48031 for CO Patent Application No. 10-121.513, rec'd Oct. 7, 2014 (English translation) (8 pages).
Office Action for JP Patent Application No. 2013-218129, dated Sep. 29, 2014 (2 pages).
Office Action for JP Patent Application No. 2013-218139, dated Sep. 29, 2014 (with English translation) (4 pages).
Fourth Office Action for EA Application No. 201190110/28, dated Nov. 2, 2014 (with English translation) (4 pages).
Substantive Search and Examination Report for AP/P/2013/006767, dated Nov. 14, 2014 (6 pages).
Notification of Defects for IL Patent Application No. 218752, dated Sep. 1, 2014 (English translation) (2 pages).
Extended European Search Report for EP Application No. 14181224.8, dated Oct. 29, 2014 (10 pages).
Notification of the Second Office Action for CN Patent Application No. 201180035776.1, dated Oct. 30, 2014 (with English transation) (7 pages).
Notice of Allowance mailed Jan. 6, 2011 for U.S. Appl. No. 12/428,176.
Notice of Allowance mailed Apr. 12, 2011 for U.S. Appl. No. 12/428,176.
Office Action mailed Sep. 23, 2011 for U.S. Appl. No. 13/196,117.
Notice of Allowance mailed Mar. 27, 2012 for U.S. Appl. No. 13/196,117.
Notice of Allowance mailed Jul. 16, 2012 for U.S. Appl. No. 13/196,117.
Office Action mailed Jan. 22, 2013 for U.S. Appl. No. 13/649,511.
Office Action mailed Aug. 15, 2013 for U.S. Appl. No. 13/649,511.
Notice of Allowance mailed Feb. 13, 2014 for U.S. Appl. No. 13/649,511.
Notice of Allowance mailed Jun. 3, 2014 for U.S. Appl. No. 13/649,511.
Office Action mailed Dec. 23, 2010 for U.S. Appl. No. 12/428,234.
Notice of Allowance mailed Apr. 7, 2011 for U.S. Appl. No. 12/428,234.
Office Action mailed Dec. 23, 2010 for U.S. Appl. No. 12/702,957.
Notice of Allowance mailed Apr. 26, 2011 for U.S. Appl. No. 12/702,957.
Notice of Allowance mailed Feb. 17, 2011 for U.S. Appl. No. 12/885,917.
Office Action mailed Mar. 27, 2012 for U.S. Appl. No. 13/050,820.
Office Action mailed Oct. 16, 2012 for U.S. Appl. No. 13/050,820.
Notice of Allowance mailed Jan. 31, 2013 for U.S. Appl. No. 13/050,820.
Office Action (Restriction Requirement) mailed Sep. 14, 2012 for U.S. Appl. No. 12/886,248.
Office Action mailed Nov. 6, 2012 for U.S. Appl. No. 12/886,248.
Office Action mailed Mar. 4, 2013 for U.S. Appl. No. 12/886,248.
Final Rejection mailed Aug. 21, 2014 for U.S. Appl. No. 12/886,248.
Notice of Allowance mailed Aug. 10, 2012 for U.S. Appl. No. 13/117,060.
Notice of Allowance mailed Nov. 28, 2012 for U.S. Appl. No. 13/117,060.
Office Action (Restriction Requirement) mailed Jul. 3, 2012 for U.S. Appl. No. 13/189,373.
Office Action mailed Sep. 14, 2012 for U.S. Appl. No. 13/189,373.
Written Opinion for PCT International Application No. PCT/US2009/041447, mailed Aug. 7, 2009 (6 pages).
International Preliminary Report on Patentability for PCT International Application No. PCT/US2009/041447, mailed Oct. 26, 2010 (7 pages).
International Search Report for PCT International Application No. PCT/US2010/023586, mailed Aug. 4, 2010 (4 pages).
Written Opinion for PCT International Application No. PCT/US2010/023586, mailed Aug. 4, 2010 (5 pages).
International Preliminary Report on Patentability for PCT International Application No. PCT/US2010/023586, mailed Aug. 16, 2011 (6 pages).
Written Opinion for PCT International Application No. PCT/US2010/049471, mailed Nov. 18, 2010 (6 pages).
International Search Report for PCT International Application No. PCT/US2011/028897, mailed Aug. 1, 2011 (6 pages).
Written Opinion for PCT International Application No. PCT/US2011/028897, mailed Aug. 1, 2011 (6 pages).
International Preliminary Report on Patentability for PCT International Application No. PCT/US2011/028897, mailed Mar. 26, 2013 (7 pages).
International Search Report for PCT International Application No. PCT/US2011/029441, mailed Aug. 1, 2011 (6 pages).
Written Opinion for PCT International Application No. PCT/US2011/029441, mailed Aug. 1, 2011 (6 pages).
International Preliminary Report on Patentability for PCT International Application No. PCT/US2011/029441, mailed Mar. 26, 2013 (7 pages).
Written Opinion for PCT International Application No. PCT/US2011/038253, mailed Jul. 29, 2011 (5 pages).
Written Opinion for PCT International Application No. PCT/US2011/044581, mailed Nov. 7, 2011 (6 pages).
International Search Report for PCT International Application No. PCT/US2011/045102, mailed Nov. 9, 2011 (4 pages).
Written Opinion for PCT International Application No. PCT/US2011/045102, mailed Nov. 9, 2011 (4 pages).
International Preliminary Report on Patentability for PCT International Application No. PCT/US2011/045102, mailed Jan. 22, 2013 (5 pages).
Official Action (ARIPO Form No. 18) with Substantive Search and Examination Report for AP Application No. AP/P/2010/005414, dated Mar. 14, 2014 (6 pages).
First Examination Report for AU Patent Application No. 2009240642, dated Aug. 2, 2012.

(56) References Cited

OTHER PUBLICATIONS

Office Action for CN Patent Application No. 200980114224.2, dated Nov. 30, 2012 (with English translation).
Office Action for CN Patent Application No. 200980114224.2, dated Aug. 19, 2013 (with English translation).
First Examination Report for CO Patent Application No. 10-121513-5, dated Dec. 10, 2012 (with English translation).
Resolution No. 72986 for CO Patent Application No. 10-121513-5, rec'd Dec. 23, 2013) (12 pages) (English translation).
First Examination Report for EA Patent Application No. 201071170, dated Apr. 25, 2012 (with English translation).
Second Examination Report for EA Patent Application No. 201071170, dated Oct. 25, 2012 (with English translation).
Third Examination Report for EA Patent Application No. 201071170, dated Oct. 10, 2013 (with English translation).
Statement of Opposition, Mar. 31, 2011, for EC Patent Application No. SP-10-10609 (with English translation).
First Examination Report for ID Patent Application No. W00 2010 03923, dated Apr. 5, 2013 (with English translation).
First Examination Report for IL Patent Application No. 208515, dated Jan. 6, 2013 (English translation).
Supplement Supplement to First Examination Report for IL Patent Application No. 208515, dated Jan. 15, 2013 (English translation).
First Examination Report for JP Patent Application No. 2011-506435, dated Aug. 22, 2013 (with English translation).
First Examination Report (in English) for MX Patent Application No. MX/a/2010/011661, dated Oct. 26, 2011.
First Examination Report for NZ Patent Application No. 588400, dated Apr. 11, 2011.
Second Examination Report and Notice of Acceptance for NZ Patent Application No. 588400 dated Jul. 27, 2012.
First Examination Report for TW Patent Application No. 098113324, dated Oct. 30, 2012 (English translation).
First Examination Report for VN Patent Application No. 1-2010-02653, dated Apr. 26, 2012 (with English translation).
Office Action with Search Report for TW Patent Application No. 102115415, dated May 15, 2014 (with English translation).
ARIPO Form 21 and Substantive Examination Report for AP Application No. AP/P/2010/005439, dated Mar. 18, 2014.
First Examination Report for AU Patent Application No. 2009240630, dated Jun. 14, 2012.
Second Examination Report for CN Patent Application No. 200980120218.8, dated Jun. 21, 2013 (with English translation).
First Examination Report for CN Patent Application No. 200980120218.8, dated Nov. 13, 2012 (with English translation).
Rejection Decision for CN Patent Application No. 200980120218.8, dated Feb. 7, 2014 (with English translation).
Notification of Reexamination for CN Patent Application No. 200980120218.8, dated Sep. 1, 2014 (with English translation).
First Examination Report for CO Patent Application No. 10-131479, dated Oct. 23, 2012.
Second Examination Report for CO Patent Application No. 10-131479, dated Jun. 20, 2013.
Resolution No. 56673 for CO Patent Application No. 10-131479, dated Sep. 27, 2013 with English translation.
First Examination Report for EA Patent Application No. 201071128, dated Apr. 25, 2012 (with English translation).
Second Examination Report for EA Patent Application No. 201071128, dated Oct. 24, 2012 (with English translation).
Third Examination Report for EA Patent Application No. 201071128, dated Apr. 29, 2013 (with English translation).
First Examination Report for ID Patent Application No. W00 2010 03957, dated Apr. 25, 2013 (with English translation).
First Examination Report for IL Patent Application No. 208701, dated Jan. 13, 2013 (English translation).
First Examination Report for JP Patent Application No. 2011-506429, dated Aug. 22, 2013 (with English translation).
First Examination Report for NZ Patent Application No. 588670, dated Apr. 8, 2011.
First Examination Report for UA Patent Application No. 2010 13030, dated Mar. 2, 2013 (with English translation).
First Examination Report for VN Patent Application No. 1-2010-02939, dated Apr. 19, 2012 (with English translation).
Second Examination Report for VN Patent Application No. 1-2010-02939, dated Jul. 26, 2012 (with English translation).
Search Report for AP Patent Application No. AP/P/2011/005818, dated Sep. 19, 2013.
Form 21 for AP Patent Application No. AP/P/2011/005818, dated Sep. 19, 2013.
Patent Examination Report No. 1 for AU Patent Application No. 2010213873, Jun. 4, 2014.
First Office Action for CL Patent Application No. 1906-2011, received May 7, 2013 (with English translation).
Second Office Action for CL Patent Application No. 1906-2011, Oct. 16, 2013 (with English translation).
First Office Action for CN Patent Application No. 201080011960.0, dated Jun. 8, 2013 (with English translation).
Notification of the Second Office Action & Search Report for CN Patent Application No. 201080011690.0, dated Jan. 8, 2014 (with English translation).
Notification of the Third Office Action for CN Patent Application No. 201080011690.0, dated Jul. 29, 2014 (with English translation).
Office Action for CO Patent Application No. 11-109.501 dated Nov. 27, 2012 (English translation).
Office Action for CO Patent Application No. 13-235103-1 rec'd Aug. 27, 2014 (English translation).
First Office Action for EA Patent Application No. 201190110/28, dated Apr. 26, 2012 (with English translation).
Second Office Action for EA Patent Application No. 201190110/28, dated Jan. 28, 2013 (with English translation).
Third Office Action for EA Application No. 201190110/28, dated Oct. 18, 2013.
Communication under 161/162 for EP Patent Application No. 10704068.5, dated Sep. 6, 2011.
First Office Action for EP Patent Application No. 10704068.5, dated Jun. 18, 2012.
Extended European Search Report for EP Application No. 13194605.5, dated Mar. 13, 2014.
Substantive Examination Report Stage 1 for ID Application No. W-00201103126, received Jun. 10, 2014 (with English translation).
First Office Action for IL Patent Application No. 214396, dated Jul. 8, 2013 (English translation).
Notification of Defects for IL Patent Application No. 214396, dated Nov. 11, 2013 (English translation).
Notice of Reasons for Rejection for JP Application No. 2011-549324, dated Mar. 26, 2014 (with English translation).
Notice of Reasons for Rejection for JP Application No. 2011-549324, dated Jul. 28, 2014 (with English translation).
Office Action for MX Application No. MX/a/2011/008409, dated Mar. 25, 2014 (with English translation).
Further Examination Report for NZ Application No. 594370, dated Oct. 8, 2013.
Office Action in PE Application No. 1464 dated Sep. 12, 2013 (with English translation).
First Office Action for UA Application No. a 2011 10568, received Apr. 7, 2014 (with English translation).
Search and Exam Report for AP Application No. AP/P/2012/006189, dated Jun. 26, 2014.
Patent Examination Report No. 1 for AU Application No. 2011306066, dated Nov. 21, 2013.
Office Action for CA Patent Application No. 2,773,772, dated Aug. 12, 2014.
Opposition for CL Patent Application No. 727-2013, dated Oct. 15, 2013 (with English translation).
Notification of the First Office Action and Search Report for CN Patent Application No. 201080041902.X, dated Nov. 12, 2013 (with English translation).
Office Action No. 425 for CO Patent Application No. 12 050 579, dated Jan. 21, 2014 (with English translation).
First Office Action for EA Patent Application No. 201390141/28, with English translation, received Aug. 14, 2014.

(56) References Cited

OTHER PUBLICATIONS

Opposition for EC Patent Application No. SP-2012-11817, dated May 27, 2013.
Communication under 161/162 for EP Patent Application No. 10763083.2, dated May 11, 2012.
Communication pursuant to Article 94(3) EPC for EP Patent Application No. 10763083.2, dated May 2, 2014.
Communication under 161/162 for EP Patent Application No. 11715792.5, dated Apr. 26, 2013.
Communication pursuant to Article 94(3) EPC for EP Patent Application No. 11715792.5, dated Feb. 14, 2014.
Notification Prior to Examination for IL Patent Application No. 218599, dated Nov. 13, 2012 (English translation).
Notification of Reasons for Rejection for JP Patent Application No. 2012-529958, dated Aug. 5, 2014.
Office Action for MX Application No. MX/a/2013/003179, dated Feb. 25, 2014 (English translation).
First Examination Report for NZ Patent Application No. 608070, dated Nov. 7, 2013.
Official Action for SV National Phase Entry of International Application No. PCT/US2010/049471, dated Nov. 6, 2013 (with English translation).
Patent Examination Report No. 1 for AU Patent Application No. 2010295392, dated Sep. 16, 2014.
Notification of the First Office Action for CN Patent Application No. 201080041946.2, dated Dec. 18, 2013 with Search Report (and English translation).
Notification Prior to Examination for IL Patent Application No. 218752, dated Jan. 20, 2014 (English translation) (3 pages).
Notification of Reasons for Rejection for JP Patent Application No. 2012-529963, dated Aug. 28, 2014 (with English translation).
Office Action with Search Report for TW Patent Application No. 099131868, dated May 22, 2014 (with English translation).
Patent Examination Report No. 1 for AU Patent Application No. 2011282241, dated Jul. 9, 2014.
Opposition filed Against CL Patent Application 00076-2013, dated Jun. 18, 2014 (with English translation).
Office Action with Search Report, dated Jun. 27, 2014 for CN Patent Application No. 201180035281.9 (with English translation).
Official Action for EA Patent Application No. 201390133, dated Mar. 27, 2014 (and English translation).
Opposition for EC Patent Application No. SP-13-12451, date of Notification Apr. 23, 2014 (and English translation).
Communication under 161/162 for EP Patent Application No. 11743400.1, dated Feb. 26, 2013.
Office Action for MX Application No. MX/a/2013/000656, dated Apr. 22, 2014 (and English translation).
Office Action for MX Application No. MX/a/2013/000656, dated Aug. 4, 2014 (and English translation).
Second Office Action for UA Patent Application No. 2011 10568, dated Aug. 11, 2014 (and English translation).
Patent Examination Report No. 1 for AU Application No. 2011280910, dated Jun. 10, 2014.
Notification of the First Office Action for CN Patent Application No. 201180035776.1, dated Feb. 27, 2014 (with English translation).
Office Action for CO Application No. 13 004212, dated Dec. 4, 2013 (and English translation).
Office Action for EA Patent Application No. 201390152, dated Apr. 14, 2014 (and English translation).
Communication under 161/162 for EP Patent Application No. 11743709.5, dated Mar. 1, 2013.
Office Action for MX Application No. MX/a/2013/000744, dated Apr. 22, 2014 (and English translation).
First Office Action for VN Patent Application No. 1-2012-03895, dated Feb. 8, 2013 (with English translation).
Alessandrini, L. et al., "Synthesis of Differently Protected 1-C-methyl-ribofuranoses Intermediates for the Preparation of Biologically Active 1'-C-methyl-ribonucleosides," *Journal of Carbohydrate Chemistry*, 27(5):332-344, 2008.

Notification of Defects for IL Patent Application No. 208515, dated Aug. 25, 2014 (English translation).
Notification of Defects for IL Patent Applicaton No. 208701, dated Aug. 25, 2014 (English translation).
Notification of Defects for IL Patent Application No. 218599, dated Aug. 25, 2014 (English translation).
Asbun, W. et al., "Synthesis of 5-substituted Pyrimidines. II," *Journal of Organic Chemistry*, 31:140-142, 1968.
Ballini, R. et al., "Enantioselective Synthesis of the Lactone Moiety of the Mevinic Acids using D-Xylose as a Chiral Precursor," *Journal of the Chemical Society, Perkin Transactions 1*, pp. 490-491, 1991.
Bandini, M. et al., "Indium tribromide: a highly effective catalyst for the addition of trimethylsilyl cyanide to α-hetero-substituted ketone," *Tetrahedron Letters*, 42:3041-3043, 2001.
Barker, R. et al., "2,3,5-Tri-O-benzyl-D-ribosyl and -L-arabinosyl Bromides," *Journal of Organic Chemistry*, 26(11):4605-4609, 1961.
Belokon, Y. et al., "Optimized catalysts for the asymmetric addition of trimethylsilyl cyanide to aldehydes and ketones," *Tetrahedron*, 57:771-779, 2001.
Benksim, A. et al., "A Novel Stereospecific Synthesis of Glycosyl Cyanides from 1,2-O-sulfinyl Derivatives," *Organic Letters*, 6(22):3913-3915, 2004.
Brown, N., "Progress towards improving antiviral therapy for hepatitis C virus polymerase inhibitors. Part O: Nucleoside analogues," *Expert Opinion*, 18:709-725, 2009.
Butora et al., "Synthesis and HCV inhibitory properties of 9-deaza- and 7,9-dideaza-7-oxa-2'-C-methyladenosine," *Bioorganic & Medicinal Chemistry*, 15(15)5219-5229, 2007.
Cabirol, F. et al., "robust and Efficient, yet Uncatalyzed, Synthesis of Triarylsilyl-protected Cyanohydrins from Ketones," *Journal of Organic Chemistry*, 73:2446-2449, 2008.
Calès, P. et al., "Treatment of liver fibrosis: clinical aspects," *Gastroentérologie Clinique et Biologique*, 33(10-11):958-966, 2009.
Camps, P., "Studies on Structurally Simple -αβ-butenolides-II," *Tetrahedron*, 38(15):2395-2402, 1982.
Carroll, S., "Robust Antiviral Efficacy upon Administration of a Nucleoside Analog to Hepatitis C Virus-Infected Chimpanzees," *Antimicrobial Agents and Chemotherapy*, 53(3):926-934, 2009.
Chapman, J. et al., "RSV604, a Novel Inhibitor of Respiratory Syncytial Virus Replication," *Antimicrobial Agents and Chemotherapy*, 51(9):3346-53, 2007.
Cihlar, T. et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," *Antimicrobial Agents and Chemotherapy*, 52(2):655-65, 2008.
Clark, J. et al., "Design, Synthesis, and Antiviral Activity of 2'-Deoxy-2'-fluoro-2'-C-methylcytidine, a Potent Inhibitor of Hepatitis C Virus Replication," *Journal of Medicinal Chemistry*, 48(17):5504-5508, 2005.
Dai, Q. et al., "Synthesis of 2'-C-β-Fluoromethyluridine," *Organic Letters*, 5(6):807-810, 2003.
De Las Heras, "Synthesis of Ribosyl and Arabinosyl Cyanides by Reaction of 1-O-Acyl Sugars with Trimethylsilyl Cyanide," *Journal of the Chemical Society, Perkin Transactions 1*, 1982:903-907, 1982.
Domingo, E. et al., "The quasispecies (extremely heterogeneous) nature of viral RNA genome populations: biological relevance—a review," *Gene*, 40:1-8, 1985.
Dondoni, A. et al., "Thiazole-Based Synthesis of Formyl C-Glycosides," *Journal of Organic Chemistry*, 59:6404-6414, 1994.
Fukumoto, T. et al., "Viral Dynamics of Hepatiis C Early After Orthotopic Liver Transplantation: Evidence for Rapid Turnover of Serum Virions," *Hepatology*, 24:1351-1354, 1996.
Garcia, I. et al., "Synthesis of (2,3,4,6-tetra-O-acetyl-alpha-D-glycopyranosyl)thiophene derivatives as new C-nucleoside analogues," *J. Carbohydrate Chemistry* 20(7/8)681-687, 2001.
Greene, T.W., *Protective Groups in Organic Chemistry* (John Wiley & Sons, New York, 1991).
Gudmundsson, K. et al., "Synthesis of imidazo[1,2-a]pyridine C-Nucleosides with an Unexpected Site of Ribosylation," *Journal of Organic Chemistry*, 62:3453-3459, 1997.

(56) References Cited

OTHER PUBLICATIONS

Gudmundsson, K. et al., "The Condensation of 2,6-dichloroimidazo[1,2-a]pyridine C-nucleoside with an Unexpected Site of Ribosylation," *Tetrahedron Letters*, 37(14):2365-2368, 1996.
Gunic, E. et al., "Cyclic monophosphate prodrugs of base-modified 2'-C-methyl ribonucleosides as potent inhibitors of hepatitis C virus Rna replication," *Bioorganic & Medicinal Chemistry Letters*, 17:2452-2455, 2007.
Hamann, M. et al., "Synthesis and antiviral evaluation of 7,9-dideaza-8-thiapurine C-nucleoside derivatives," *Collection Symposium Series*, 10:347-349, 2008.
Hamann, M. et al., "Synthesis and antiviral evaluation of thieno[3,4-d]pyrimidine C-nucleoside analogues of 2',3'dideoxy- and 2',3'-dideoxy-2',3'-didehydro-adenosine and -inosine," *Bioorganic & Medicinal Chemistry*, 17:2321-2326, 2009.
Han, H.K. et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," *Synthetic Communications*, 22(19):2815-2822, 1992.
Hoffman, M. et al., "When, in the Context of Drug Design, Can a Fluorine Atom Successfully Substitute a Hydroxyl Group?," *International Journal of Quantum Chemistry*, 89:419-427, 2002.
Kabat, M. et al., "Nucleosides, CXLVIII, Synthesis of 6-(β-D-Ribofuranosyl)picolinamide: A Novel C-Nucleoside from D-Ribonolactone," *Chemical & Pharmaceutical Bulletin*, 36(2):634-640, 1988.
Klumpp, K. et al., "The Novel Nucleoside Analog R1479 (4'-Azidocytidine) is a Potent Inhibitor of NS5B-dependent Rna Synthesis and Hepatitis C virus Replication in Cell Culture," *Journal of Biological Chemistry*, 281(7):3793-3799, 2006.
Lefebvre, I. et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," *Journal of Medicinal Chemistry*, 38(20):3941-3950, 1995.
Lefebvre, I. et al., "Synthesis, Decomposition Pathways and 'in Vitro' Evaluation of Bioreversible Phosphotriesters of Azt," *Nucleosides, Nucleotides & Nucleic Acids*, 14(3-5):763-766, 1995.
Lindell, S. D. et al., "Synthesis and Biochemical Testing of 3-(Carboxyphenylethyl)imidazo[2,1-f][1,2,4]triazines as Inhibitors of Amp Deaminase," *ACS Medicinal Chemistry Letters*, 1(6):286-289, 2010.
Lovelette, C.A., "1,2,4-Triazines. Synthesis of selected members of the s-triazolo[3,4-f][1,2,4]triazine and tetrazolo[1,5-f][1,2,4]triazine ring systems," *Journal of Heterocyclic Chemistry*, 16:555-560, 1979.
Martell, M. et al., "Hepatitis C Virus (HCV) Circulates as a Population of Different but Closely Related Genomes: Quasispecies Nature of HCV Genome Distribution," *Journal of Virology*, 6695:3225-3229, 1992.
Mason, S. et al., "Polyadenylation-dependent screening assay for respiratory syncytial virus RNA transcriptase activity and identification of an inhibitor," *Nucleic Acids Research*, 32(16):4758-4767, 2004.
Matulic-Adamic, J. et al., "Synthesis of 3-(β-D-Ribofuranosyl)-2-Fluoropyridine and 3-(β-D-Ribofuranosyl)-Pyridin-2-one," *Tetrahedron Letters*, 38(2):203-206, 1997.
Matulic-Adamic, J. et al., "Synthesis of 5-(β-D-Ribofuranosyl)-Pyridin-2-one: a 'Deletion-Modified' Analogue of Uridine," *Tetrahedron Letters*, 38(10):1669-1672, 1997.
Meppen, M. et al., "Cyclic phosphoramidates as prodrugs of 2'-C-methylcytidine," *European Journal of Medicinal Chemistry*, 44(9):3765-3770, 2009.
Migliaccio, G. et al., "Characterization of Resistance to Non-obligate Chain-terminating Ribonucleoside Analogs That Inhibit Hepatitis C Virus Replication in vitro," *The Journal of Biological Chemistry*, 278(49):49164-49170, 2003.
Murakami et al., "Mechanism of Activation of Beta-D-2'-Fluoro-2'-C-Methylcytidine and Inhibition of Hepatitis C Virus NS5B RNA Polymerase," *Antimicrob Agents Chemother.* 51(2):503-509, Feb. 2007.
Moscow, J. et al., "Reduced Folate Carrier Gene (RFC1) Expression and Anti-Folate Resistance in Transfected and Non-Selected Cell Lines," *International Journal of Cancer*, 72:184-190, 1997.
Neumann, A. et al., "Hepatitis C Viral Dynamics in Vivo and the Antiviral Efficacy of Interferon-α Therapy," *Science*, 282:103-107, 1998.
Ogura, H. et al., "Reaction of Ethynyl Compounds with Lactones," *Journal of Organic Chemistry*, 37(1):72-75, 1972.
Pankiewicz, K. et al., "C-Nucleoside Analogues of Nicotinamide Mononucleotide (NMN)," *Nucleosides and Nucleotides*, 7(5&6):589-593, 1988.
Pankiewicz, K. et al., "Efficient Synthesis of 5-(β-D-Ribofuranosyl)nicotinamide and its α-Isomer," *Journal of Organic Chemistry*, 53:3473-3479, 1988.
Patil, S et al., "C-Glycosylation of Substituted Heterocycles under Friedel-Crafts Conditions (II): Robosylation of Multi-Functionalized Thiophenes and Furans for the Synthesis of Purine-Like C-Nucleosides," *Nucleosides & Nucleotides*, 9(7):937-956, 1990.
Patil, S.A. et al., "Synthesis of some new thieno[3,4-d]pyrimidines and their C-nucleosides," *Journal of Heterocyclic Chemistry*, 30(2):509-515, 1993.
Piccirilli, J. et al., "A Direct Route to 3-(D-Ribofuranosyl)pyridine Nucleosides," *Helvetica Chimica Acta*, 74:397-406, 1991.
Pierra, C. et al., "Synthesis and Pharmacokinetics of Valopicitabine (NM283), and Efficient Prodrug of the Potent Anti-HCV Agent 2'-C-Methylcytidine," *Journal of Medicinal Chemistry*, 49(22):6614-6620, 2006.
Rao, S. et al., "C-Glycosylation of Substituted Heterocycles under Friedel-Crafts Conditions (I): A Two-Step Synthesis of the Thieno[3,4-d]Pyrimidine C-Nucleoside Analog of Inosine," *Tetrahedron Letters*, 29(29):3537-3540, 1988.
Schultz, C., "Prodrugs of Biologically Active Phosphate Esters," *Bioorganic & Medicinal Chemistry*, 11:885-898, 2003.
Silverman, R.B., "The Organic Chemistry of Drug Design and Drug Action," 2nd Ed., pp. 29-34 (2004).
Uchiyama et al., "O-selective Phosphorylation of Nucleosides without N-protection," *J. Org. Chem.* 58(2), Jan. 1, 1993.
Wu, Q. et al., "Synthetic Methodologies for C-Nucleosides," *Synthesis*, 10:1533-1553, 2004.
Yamanaka, G. et al., "Metabolic Studies on BMS-200475, a New Antiviral Compound Active against Hepatitis B Virus," *Antimicrobial Agents and Chemotherapy*, 43(1):190, 1999.
Zhang, P. et al., "A Practical Synthesis of (2R)-3,5-di-O-benzoyl-2-fluoro-2-C-methyl-D-ribono-y-lactone," *Tetrahedron: Asymmetry*, 20:305-312, 2009.

\* cited by examiner

US 9,090,642 B2

METHODS FOR THE PREPARATION OF DIASTEROMERICALLY PURE PHOSPHORAMIDATE PRODRUGS

CROSS-REFERENCE TO RELATED APPLICATIONS

This application is a National Stage Application of International Application No. PCT/US2011/044581, filed Jul. 19, 2011, which claims the benefit of U.S. Provisional Application No. 61/365,621, filed Jul. 19, 2010. The contents of the aforementioned applications are incorporated herein by reference in their entirety.

FIELD OF THE INVENTION

The invention relates generally to methods for preparing compounds with antiviral activity, most particularly to prodrugs of inhibitors of hepatitis C virus RNA-dependent RNA polymerase.

BACKGROUND OF THE INVENTION

The hepatitis C virus (HCV) is a leading cause of chronic liver disease worldwide (Boyer, N. et al. J Hepatol. 32:98-112, 2000) and may lead to hepatic fibrosis, cirrhosis and hepatocellular carcinoma (Cale, P., *Gastroenterolgy Clin. Biol.* 2009, 33, 958). A significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000).

Currently, there are primarily two antiviral compounds, ribavirin, a nucleoside analog, and interferon-alpha (α) (IFN), which are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079 but additional treatments for HCV infections have not yet become available for patients. Therefore, drugs having improved antiviral and pharmacokinetic properties with enhanced activity against development of HCV resistance, improved oral bioavailability, greater efficacy, fewer undesirable side effects and extended effective half-life in vivo (De Francesco, R. et al. (2003) Antiviral Research 58:1-16) are urgently needed.

RNA-dependent RNA polymerase (RdRp) is one of the best studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Biochemical targets such as NS5B are important in developing HCV therapies since HCV does not replicate in the laboratory and there are difficulties in developing cell-based assays and preclinical animal systems.

Inhibition of viral replication by nucleosides has been extensively studied (De Clercq, E. (2001) J. Clin. Virol. 22:73-89) including nucleosides that inhibit RdRp. Generally, the antiviral activity of these nucleosides are attributed to the conversion of the nucleosides to their nucleoside triphosphates (NTPs) which act as inhibitors of DNA and RNA polymerases or as chain terminators following incorporation into the lengthening viral DNA or RNA strand. However, many NTPs lack adequate specificity for viral polymerases compared to host polymerases and, as a result, cause substantial toxicity. This has led to efforts to modify the core structures of nucleosides to achieve higher selectivity but many of the structural modifications have simultaneously compromised NTP production in the cells (Yamanaka, Antimicrob. Agents Chemother. 1999: 190-193).

The poor conversion of the nucleoside to NTP can often be attributed to the inability of nucleoside kinases to convert the nucleoside to the nucleoside 5'-monophosphate (NMP). NMP prodrugs have been used to bypass poor nucleoside kinase activity (Schultz, Bioorg. Med. Chem. 2003, 11, 885). Among these prodrugs, NMP phosphoramidates have been reported to increase intracellular concentrations of NTP compared to the nucleoside alone (McGuigan, J. Med. Chem. 1993, 36, 1048-1052). However, these NMP prodrugs are substrates for esterases and phosphodiesterases in the blood and other body tissues which can cleave the prodrug to a charged molelcule or to the nucleoside, respectively. The charged molecule is then impermeable to the target organ or cell and the nucleoside is poorly phosphorylated intracellularly.

The development of a highly effective, non-toxic NMP prodrug is largely an unpredictable trial and error exercise requiring the balancing of the stability of the NMP prodrug in blood with the ability of the prodrug to reach a target organ or cell, be absorbed or actively taken up by the target cell, being efficiently cleaved to the NMP intracellularly and subsequently converted to a NTP that is selective for inhibiting the viral polymerase (Perrone, *J. Med. Chem.* 2007, 50, 1840-49; Gardelli, *J. Med. Chem.* 2009, 52, 5394-5407). For the case of an orally effective RdRp inhibitor for treating HCV infection, the NMP prodrug would need to be chemically stable to the conditions of the upper intestinal tract, be efficiently absorbed from the intestinal tract, survive the many esterases of the intestinal cells and blood, be efficiently extracted by the hepatocytes, and be cleaved to the NMP and subsequently converted to a NTP in hepatocytes that is specific for inhibiting the HCV NS5B polymerase. Notably, the anti-HCV activity of phosphate prodrugs can markedly depend upon the chirality of the phosphorous in the prodrug (Gardelli, *J. Med. Chem.* 2009, 52, 5394-5407; Meppen, Abstracts of Papers, 236th ACS National Meeting, Philadelphia, Pa., United States, Aug. 17-21, 2008 (2008), MEDI-404.).

Babu, Y. S., WO2008/089105 and WO2008/141079, discloses ribosides of pyrrolo[1,2-f][1,2,4]triazine nucleobases with antiviral, anti-HCV, and anti-RdRp activity.

Butler, et al., WO2009132135, disclose 1' substituted ribosides and prodrugs comprising pyrrolo[1,2-f][1,2,4]triazine nucleobases which have anti-HCV and anti-RdRp activity but does not disclose species of the 3'-O-acylated derivatives of those ribosides or the expected properties of such derivatives. Cho, et al., U.S. 61/353,351, discloses 3'-O-acylated 1' substituted ribosides phosphate prodrugs comprising pyrrolo[1,2-f][1,2,4]triazine nucleobases that have anti-HCV activity that are efficiently delivered to the liver after oral administra-

3 tion. The efficient delivery of the prodrugs to the liver is dependent on the chirality of the phosphorous prodrug.

In view of the importance of anti-HCV therapeutics that are NMP prodrugs with chiral phosphorous atoms such as those described by Cho, et al., Gardelli, et al., Perrone et al., and Meppen, et al., new efficient methods of producing chiral phosphates of these prodrugs are needed.

SUMMARY OF THE INVENTION

Provided are methods for preparing compounds that inhibit hepatitis C virus. The compounds are prodrugs of nucleoside monophosphates that, when administered to animals, are intracellularly converted to nucleoside triphosphates. The chirality of the phosphorous atom determines the efficiency of the conversion to the nucleoside triphosphate in the animal. The method disclosed, provides a convergent synthesis of these single diastereomeric prodrugs which is an improvement over the previously disclosed chromatographic methods of separating a single diastereomer from a mixture of diastereomers.

In one embodiment, provided is a method for preparing a compound of Formula Ia or Ib:

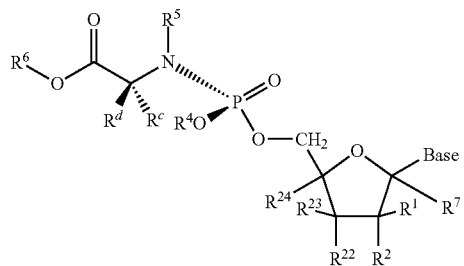

Formula Ia

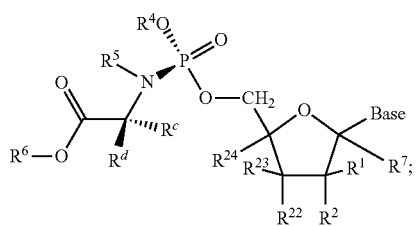

Formula Ib or a pharmaceutically acceptable salt or acid thereof;
wherein:
each $R^1$, $R^2$, $R^7$, $R^{22}$, $R^{23}$ or $R^{24}$ is independently H, $OR^{11}$, $NR^{11}R^{12}$, $C(O)NR^{11}R^{12}$, $-OC(O)NR^{11}R^{12}$, $C(O)OR^{11}$, $OC(O)OR^{11}$, $S(O)_nR^a$, $S(O)_2NR^{11}R^{12}$, $N_3$, CN, halogen, $(C_1\text{-}C_8)$alkyl, $(C_3\text{-}C_8)$carbocyclyl, $(C_4\text{-}C_8)$carbocyclylalkyl, $(C_2\text{-}C_8)$alkenyl, $(C_2\text{-}C_8)$alkynyl or aryl$(C_1\text{-}C_8)$alkyl;

or any two $R^1$, $R^2$, $R^7$, $R^{22}$, $R^{23}$ or $R^{24}$ on adjacent carbon atoms when taken together are $-O(CO)O-$ or $-O(CR^{11}R^{12})O-$ or when taken together with the ring carbon atoms to which they are attached form a double bond;

each Base is independently a naturally occurring or modified purine or pyrimidine base linked to the furanose ring through a carbon or nitrogen atom;

each n is independently 0, 1, or 2;

each $R^a$, $R^4$ or $R^6$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

4 each $R^c$ or $R^d$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl provided that $R^c$ and $R^d$ are not the same;

each $R^5$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

each $R^{11}$ or $R^{12}$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl, heteroaryl, $-C(=O)(C_1\text{-}C_8)$alkyl, $-S(O)_n(C_1\text{-}C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and wherein each $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2 NH(R^a)$, $S(O)_2NH_2$, $OR^a$ or $R^a$;

said method comprising:
(a) providing a compound of Formula II
and

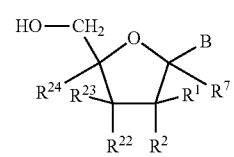

Formula II (b) treating the compound of Formula II with a compound of Formula IIIa and a base

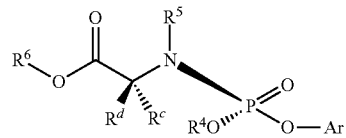

Formula IIIa thereby forming a compound of Formula Ia or
(c) treating the compound of Formula II with a compound of Formula IIIb and a base

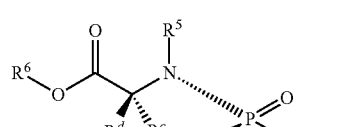

Formula IIIb thereby forming a compound of Formula Ib;

wherein:

each Ar is a $(C_6-C_{20})$ aryl or heteroaryl wherein said $(C_6-C_{20})$ aryl or heteroaryl is substituted with one or more halogen, $NO_2$, or $(C_1-C_8)$haloalkyl and optionally substituted with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$. In another aspect, Base is not uracil. In another aspect, Base is not cytosine.

In another aspect, the invention also provides novel intermediates disclosed herein which are useful for preparing Formula Ia or Formula Ib.

In other aspects, methods for the synthesis, analysis, separation, isolation, purification, and characterization of the novel intermediates of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

Typically, the method of for preparing a compound of Formula Ia from Formula II and Formula IIIa or Formula Ib from Formula II and Formula IIIb is performed in a suitable solvent. The suitable solvent is preferably an anhydrous, non-acid, non-hydroxylic solvent. Non-limiting examples of suitable solvents are ethers, for example, diethyl ether, diisopropyl ether, di t-butyl ether, tetrahydrofuran, dioxane and various glyme solvents; dimethylformamide or dimethylacetamide. A preferred solvent is tetrahydrofuran. The concentration of Formula II in the solvent is typically about 0.01 to about 1 mole per liter of solvent. The method is performed at a temperature of about 0° C. to about 80° C., more preferably about 20° C. to about 60° C.

The solution of Formula II is typically treated with a hindered base or a non-nucleophilic base. Typical, but non-limiting, examples of hindered bases are t-butyllithium, sec-isobutyllithium, lithium or sodium diisopropylamide and t-butylmagnesium halides. A preferred hindered base is t-butylmagnesium chloride. Typical, but non-limiting, examples of non-nucleophic bases are sodium hydride, potassium hydride, lithium hydride and calcium hydride. The hindered bases or non-nucleophic bases may be used as solutions in or as undiluted bases. Preferably, the bases are used as solutions in anhydrous, non-hydroxylic solvents wherein the concentration of the base in the solvent is about 0.5 to about 3 moles per liter. The molar ratio of base to the compound of Formula II is about 1:1 to about 3:1, preferably about 1.1:1 to about 1.5:1. The solution of the compound of Formula II is typically treated with the base for about 5 minutes to about two hours, preferably less than 30 minutes.

The mixture of the solution of the compound of Formula II and the base is treated with a compound of Formula IIIa or Formula IIIb for about 30 minutes to about 24 hours, preferably about one to about four hours. The molar ratio of the compound Formula II to the compound of Formula IIIa or Formula IIIb is typically about 1:1 to about 1:4. Preferably, the molar ratio is about 1:1.1 to about 1:2.

In another embodiment of the method for preparing a compound of Formula Ia or Ib or a pharmaceutically salt or ester thereof, Formula Ia is Formula IVa, Formula Ib is Formula IVb and Formula II is Formula V:

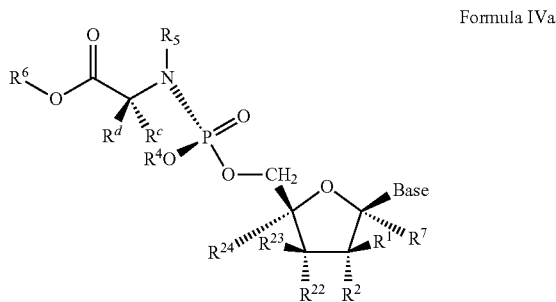

Formula IVa

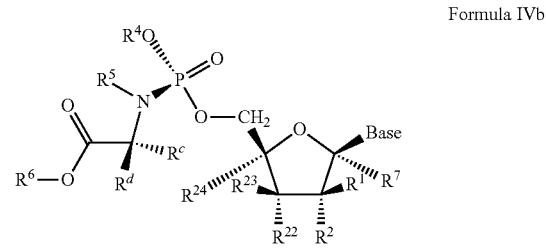

Formula IVb

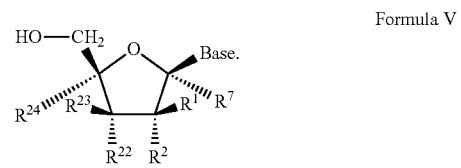

Formula V

In one embodiment of the method for preparing a compound of Formula IVa or IVb from a compound of Formula V, $R^1$ is H, halogen, optionally substituted $(C_1-C_8)$alkyl, optionally substituted $(C_2-C_8)$alkenyl or optionally substituted $(C_2-C_8)$alkynyl. In another aspect of this embodiment, $R^1$ is H. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted $(C_2-C_8)$alkynyl. In another aspect of this embodiment, $R^1$ is F. In another aspect of this embodiment, $R^2$ is F. In another aspect of this embodiment, $R^2$ is $OR^{11}$. In another aspect of this embodiment, $R^2$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is CN. In another aspect of this embodiment, $R^5$ is H. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, Ar is optionally substituted nitrophenyl. In another aspect of this embodiment, $R^{23}$ is H. In another aspect of this embodiment, $R^{22}$ is $OR^{11}$. In another aspect of this embodiment, $R^{22}$ is OH. In another aspect of this embodiment, $R^{24}$ is $N_3$. In another aspect of this embodiment, $R^{24}$ is H. In another aspect of this embodiment, Base is selected from the group consisting of:

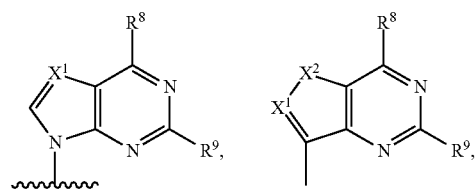

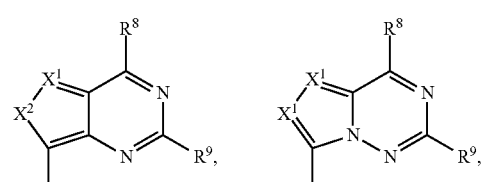

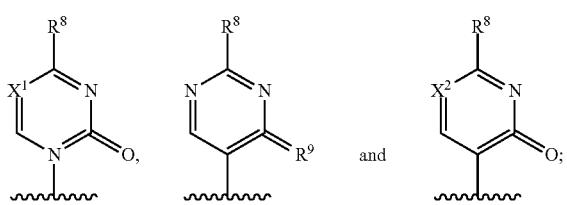

wherein:
each $X^1$ is independently N or $CR^{10}$;
each $X^2$ is independently $NR^{11}$, O, or $S(O)_n$;
each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=N($OR^{11}$), —CH($OR^{11}$)$_2$, —C(=O)$NR^{11}R^{12}$, —C(=S)$NR^{11}R^{12}$, —C(=O)$OR^{11}$, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)aryl, ($C_2$-$C_{20}$)heterocyclyl, heteroaryl, —C(=O)($C_1$-$C_8$)alkyl, —S(O)$_n$($C_1$-$C_8$)alkyl, aryl($C_1$-$C_8$)alkyl, $OR^{11}$ or $SR^{11}$;
each n is independently 0, 1, or 2;
each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=N($OR^{11}$), —CH($OR^{11}$)$_2$, —C(=O)$NR^{11}R^{12}$, —C(=S)$NR^{11}R^{12}$, —C(=O)$OR^{11}$, $R^{11}$, $OR^{11}$ or $SR^{11}$;
each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl, heteroaryl, —C(=O)($C_1$-$C_8$)alkyl, —S(O)$_n$$C_1$-$C_8$alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—; and
wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect, Base is not uracil. In another aspect, the Base is not cytosine.

In another aspect of this embodiment, Base is selected from the group consisting of:

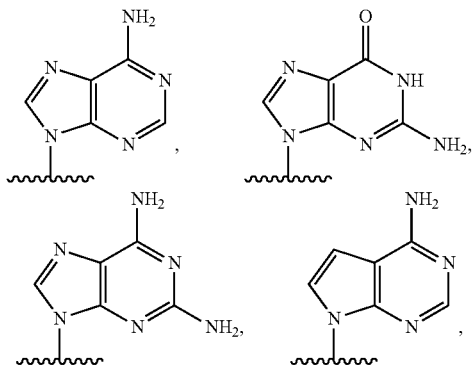

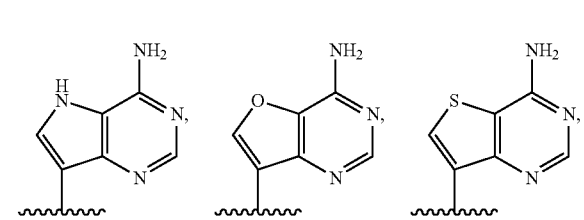

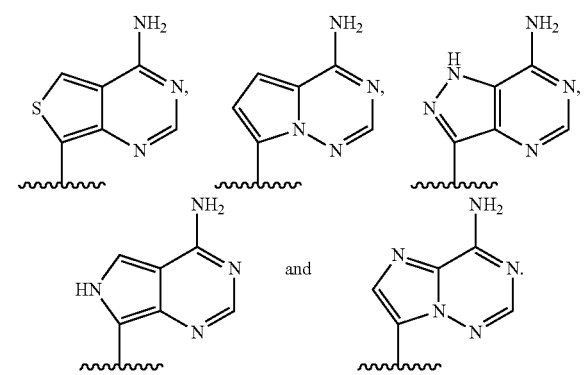

In another aspect of this embodiment, Base is selected from the group consisting of

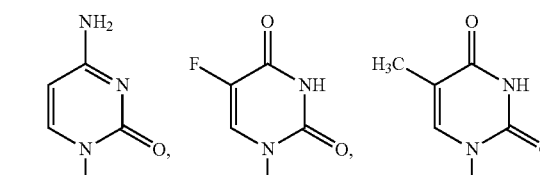

In another aspect of this embodiment, Base is selected from the group consisting of

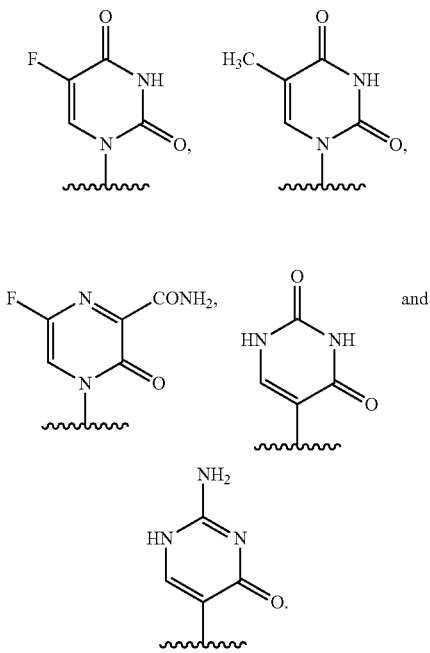

In another embodiment of the method for preparing a compound of Formula IVa or IVb from a compound of Formula V, $R^1$ is H, halogen, optionally substituted ($C_1$-$C_8$)alkyl, optionally substituted ($C_2$-$C_8$)alkenyl or optionally substituted ($C_2$-$C_8$)alkynyl; $R^2$ is $OR^{11}$ or halogen; $R^{22}$ is $OR^{11}$ and each $R^5$, $R^{23}$ and $R^{24}$ is H. In another aspect of this embodiment, $R^1$ is H. In another aspect of this embodiment, $R^1$ is optionally substituted ($C_1$-$C_8$)alkyl. In another aspect of this embodiment, $R^1$ is methyl. In another aspect of this embodiment, $R^1$ is optionally substituted ($C_2$-$C_8$)alkenyl. In another aspect of this embodiment, $R^1$ is optionally substituted ($C_2$-$C_8$)alkynyl. In another aspect of this embodiment, $R^1$ is F. In another aspect of this embodiment, $R^2$ is F. In another aspect of this embodiment, $R^2$ is OH. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is optionally substituted ($C_2$-$C_8$)alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl. In another aspect of this embodiment, Base is selected from the group consisting of:

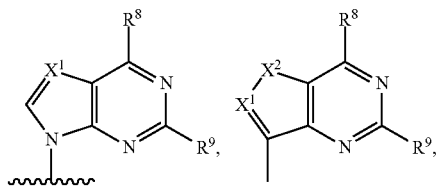

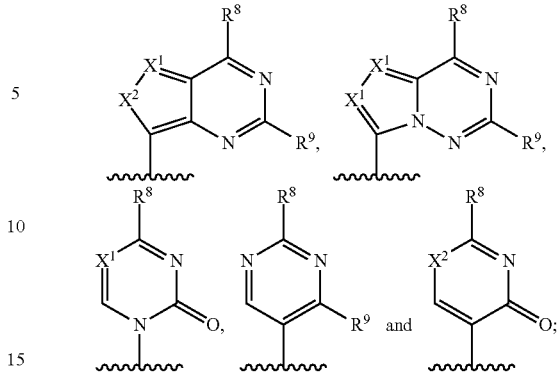

wherein:
each $X^1$ is independently N or $CR^{10}$;
each $X^2$ is independently $NR^{11}$, O, or $S(O)_n$;
each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=N($OR^{11}$), —CH($OR^{11}$)$_2$, —C(=O)$NR^{11}R^{12}$, —C(=S)$NR^{11}R^{12}$, —C(=O)$OR^{11}$, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)aryl, ($C_2$-$C_{20}$)heterocyclyl, heteroaryl, —C(=O)($C_1$-$C_8$)alkyl, —S(O)$_n$($C_1$-$C_8$)alkyl, aryl($C_1$-$C_8$)alkyl, $OR^{11}$ or $SR^{11}$;
each n is independently 0, 1, or 2;
each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=N($OR^{11}$), —CH($OR^{11}$)$_2$, —C(=O)$NR^{11}R^{12}$, —C(=S)$NR^{11}R^{12}$, —C(=O)$OR^{11}$, $R^{11}$, $OR^{11}$ or $SR^{11}$;
each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl, heteroaryl, —C(=O)($C_1$-$C_8$)alkyl, —S(O)$_n$($C_1$-$C_8$)alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—; and
wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, C(O)$N(R^a)_2$, C(O)$NH(R^a)$, C(O)$NH_2$, OC(O)$N(R^a)_2$, OC(O)$NH(R^a)$, OC(O)$NH_2$, C(O)$OR^a$, OC(O)$OR^a$, C(O)$R^a$, OC(O)$R^a$, S(O)$_nR^a$, S(O)$_2N(R^a)_2$, S(O)$_2NH(R^a)$, S(O)$_2NH_2$, $OR^a$ or $R^a$. In another aspect, Base is not uracil. In another aspect, the Base is not cytosine.

In another aspect of this embodiment, Base is selected from the group consisting of:

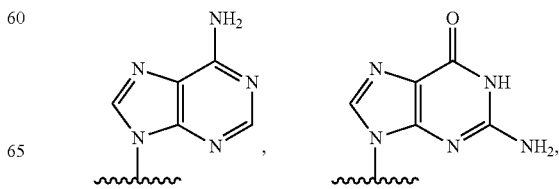

-continued

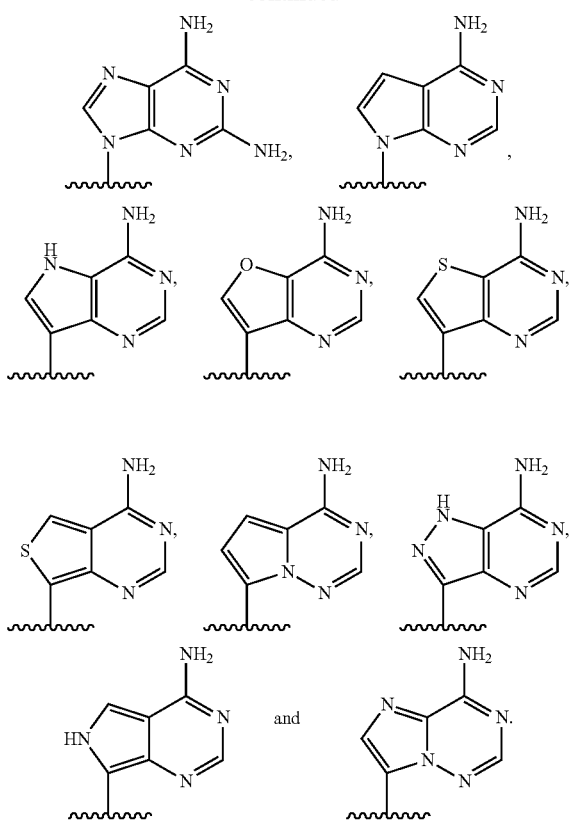

In another aspect of this embodiment, Base is selected from the group consisting of

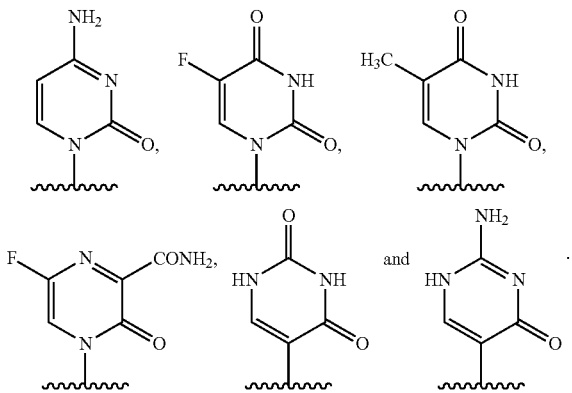

In another aspect of this embodiment, Base is selected from the group consisting of

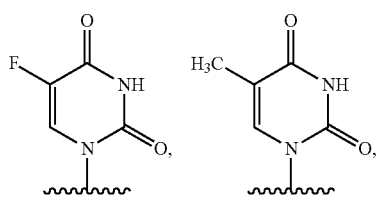

-continued

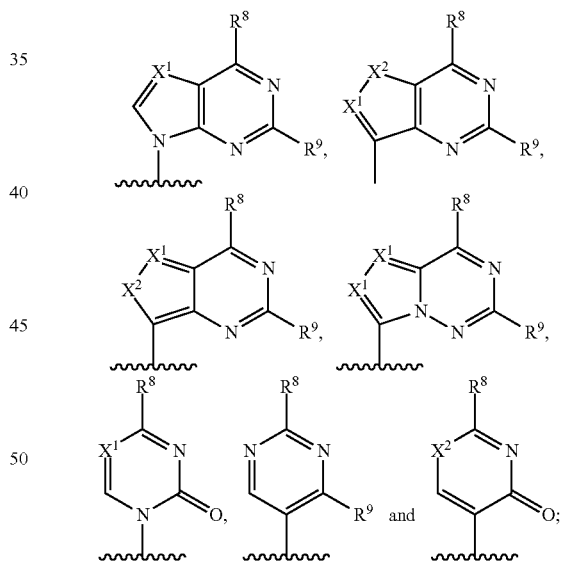

In another embodiment of the method for preparing a compound of Formula IVa or IVb from a compound of Formula V, $R^1$ is H or $CH_3$; $R^2$ is $OR^{11}$ or halogen; $R^6$ is optionally substituted $(C_1-C_8)$alkyl; one of $R^c$ or $R^d$ is H and the other of $R^c$ or $R^d$ is optionally substituted $(C_1-C_8)$alkyl; $R^{22}$ is $OR^{11}$, and each $R^5$, $R^{23}$ and $R^{24}$ is H. In another aspect of this embodiment, $R^1$ is H. In another aspect of this embodiment, $R^1$ is $CH_3$. In another aspect of this embodiment, $R^2$ is F. In another aspect of this embodiment, $R^2$ is OH. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is $CH_3$. In another aspect of this embodiment, $R^7$ is ethynyl. In another aspect of this embodiment, $R^7$ is CN. In another aspect of this embodiment, $R^4$ is optionally substituted $(C_6-C_{20})$aryl. In another aspect of embodiment, $R^4$ is optionally substituted phenyl. In another aspect of this embodiment, $R^4$ is optionally substituted napthyl. In another aspect of this embodiment, Ar is optionally substituted nitrophenyl. In another aspect of this embodiment, Base is selected from the group consisting of:

wherein:
each $X^1$ is independently N or $CR^{10}$;
each $X^2$ is independently $NR^{11}$, O, or $S(O)_n$;
each $R^8$ is independently halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1-C_8)$alkyl, $(C_2-C_8)$alkenyl, $(C_2-C_8)$alkynyl, $(C_4-C_8)$carbocyclylalkyl, $(C_6-C_{20})$aryl, $(C_2-C_{20})$heterocyclyl, heteroaryl, $-C(=O)(C_1-C_8)$alkyl, $-S(O)_n(C_1-C_8)$alkyl, aryl $(C_1-C_8)$alkyl, $OR^{11}$ or $SR^{11}$;
each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=NR$^{11}$), —CH=NHNR$^{11}$, —CH=N(OR$^{11}$), —CH(OR$^{11}$)$_2$, —C(=O)NR$^{11}$R$^{12}$, —C(=S)NR$^{11}$R$^{12}$, —C(=O)OR$^{11}$, R$^{11}$, OR$^{11}$ or SR$^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, —C(=O)$(C_1-C_8)$alkyl, —S(O)$_n$$(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —NR$^a$—; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect, Base is not uracil. In another aspect, the Base is not cytosine.

In another aspect of this embodiment, Base is selected from the group consisting of:

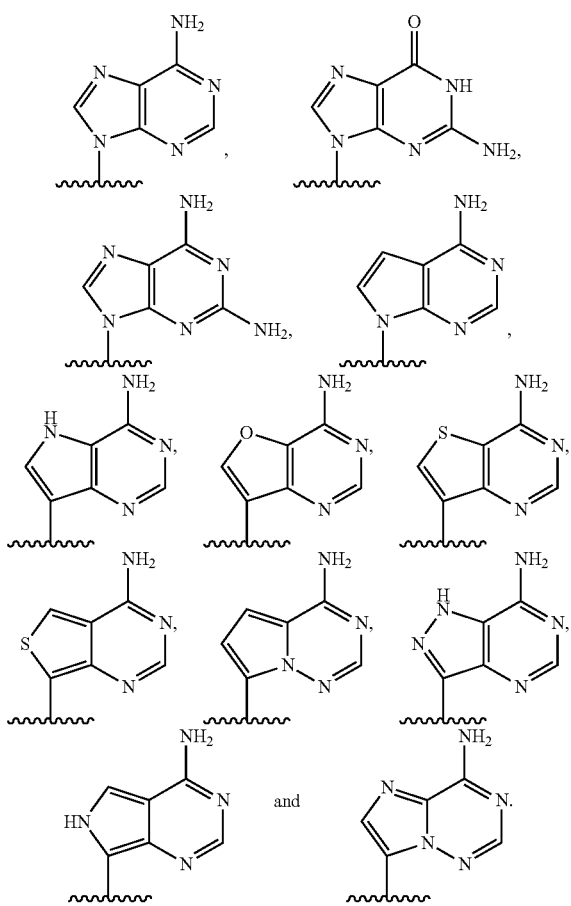

In another aspect of this embodiment, Base is selected from the group consisting of

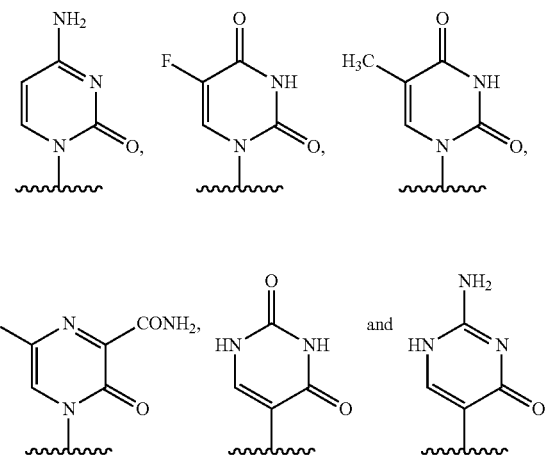

In another aspect of this embodiment, Base is selected from the group consisting of

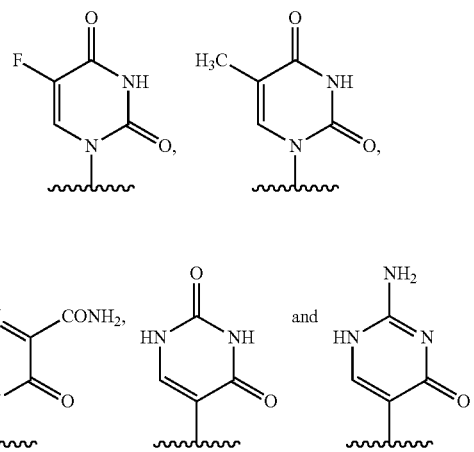

In another embodiment of the method for preparing a compound of Formula IVa or IVb from a compound of Formula V, $R^1$ is H or $CH_3$; $R^2$ is $OR^{11}$ or halogen; $R^6$ is optionally substituted $(C_1-C_8)$alkyl; one of $R^c$ or $R^d$ is H and the other of $R^c$ or $R^d$ is optionally substituted $(C_1-C_8)$alkyl; $R^{22}$ is $OR^{11}$, each $R^5$, $R^{23}$ and $R^{24}$ is H and Base is selected from the group consisting of:

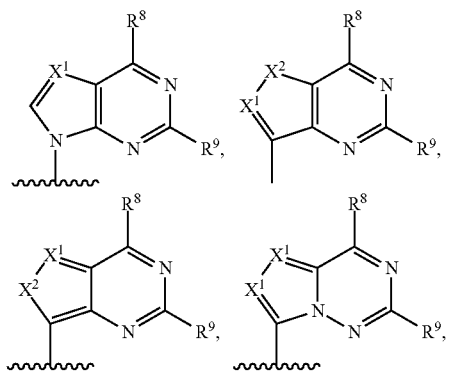

-continued

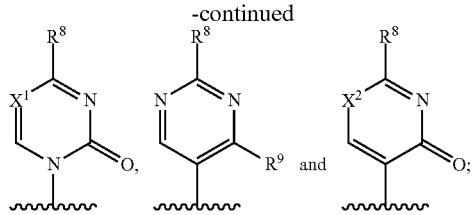

wherein:

each $X^1$ is independently N or $CR^{10}$;

each $X^2$ is independently $NR^{11}$, O, or $S(O)_n$;

each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, $(C_1$-$C_8)$alkyl, $(C_2$-$C_8)$alkenyl, $(C_2$-$C_8)$alkynyl, $(C_4$-$C_8)$carbocyclylalkyl, $(C_6$-$C_{20})$aryl, $(C_2$-$C_{20})$heterocyclyl, heteroaryl, —C(=O)$(C_1$-$C_8)$alkyl, —S(O)$_n(C_1$-$C_8)$alkyl, aryl$(C_1$-$C_8)$alkyl, $OR^{11}$ or $SR^{11}$;

each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, $R^{11}$, $OR^{11}$ or $SR^{11}$;

each $R^{11}$ or $R^{12}$ is independently H, $(C_1$-$C_8)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl$(C_1$-$C_8)$alkyl, heterocyclyl$(C_1$-$C_8)$alkyl, $(C_6$-$C_{20})$aryl, $(C_2$-$C_{20})$heterocyclyl, heteroaryl, —C(=O)$(C_1$-$C_8)$alkyl, —S(O)$_n(C_1$-$C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—; and wherein each $(C_1$-$C_8)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl$(C_1$-$C_8)$alkyl, heterocyclyl$(C_1$-$C_8)$alkyl, $(C_6$-$C_{20})$aryl, $(C_2$-$C_{20})$heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect Base is not uracil. In another aspect, the Base is not cytosine.

In another aspect of this embodiment, $R^1$ is H. In another aspect of this embodiment, $R^1$ is $CH_3$. In another aspect of this embodiment, $R^2$ is F. In another aspect of this embodiment, $R^2$ is OH. In another aspect of this embodiment, $R^{22}$ is OH. In another aspect of this embodiment, each $R^2$ and $R^{22}$ is OH. In another aspect of this embodiment, $R^7$ is H. In another aspect of this embodiment, $R^7$ is $CH_3$. In another aspect of this embodiment, $R^7$ is ethynyl. In another aspect of this embodiment, $R^7$ is CN. In another aspect of this embodiment, $R^4$ is optionally substituted $(C_6$-$C_{20})$aryl. In another aspect of embodiment, $R^4$ is optionally substituted phenyl. In another aspect of this embodiment, $R^4$ is optionally substituted napthyl. In another aspect of this embodiment, one of $R^c$ or $R^d$ is H and the other of $R^c$ or $R^d$ is $CH_3$. In another aspect of this embodiment, Ar is optionally substituted nitrophenyl. In another aspect of this embodiment, Base is

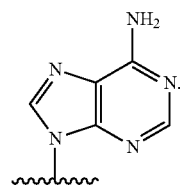

In another aspect of this embodiment, Base is

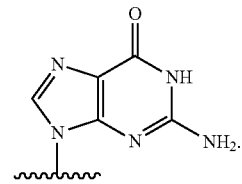 [SMILES: *n1cnc2c(=O)[nH]c(N)nc21]

In another aspect of this embodiment, Base is

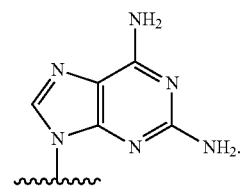 [SMILES: *n1cnc2c(N)nc(N)nc21]

In another aspect of this embodiment, Base is

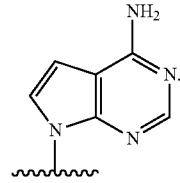

In another aspect of this embodiment, Base is

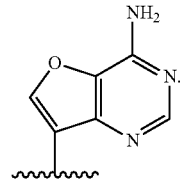

In another aspect of this embodiment, Base is

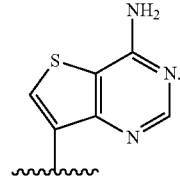

In another aspect of this embodiment, Base is

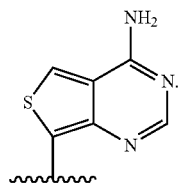

In another aspect of this embodiment, Base is

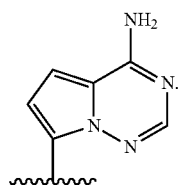

In another aspect of this embodiment, Base is

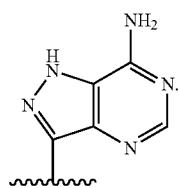

In another aspect of this embodiment, Base is

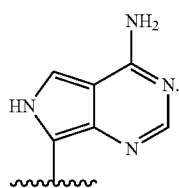 [SMILES: *c1scc2c(N)ncnc12]

In another aspect of this embodiment, Base is

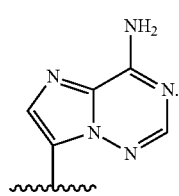

In another aspect of this embodiment, Base is

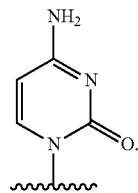

In another aspect of this embodiment, Base is

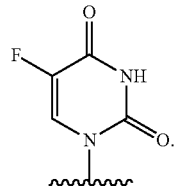

In another aspect of this embodiment, Base is

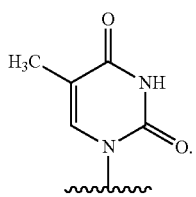

In another aspect of this embodiment, Base is

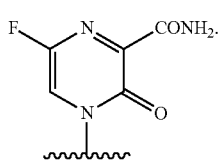 [SMILES: *n1cc(F)nc(C(N)=O)c1=O]

In another aspect of this embodiment, Base is

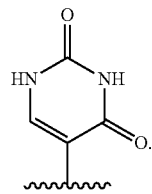 [SMILES: *c1c[nH]c(=O)[nH]c1=O]

In another aspect of this embodiment, Base is

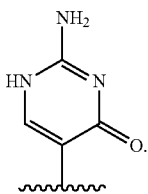

In another embodiment of the method for preparing a compound of Formula Ia or Ib or a pharmaceutically acceptable salt or ester thereof, Formula Ia is Formula VIa, Formula Ib is Formula VIb and Formula II is Formula VII:

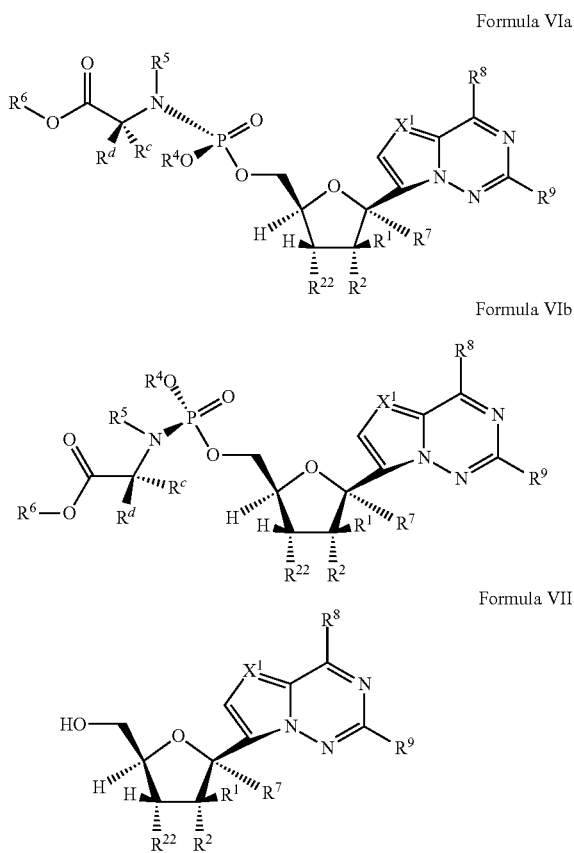

wherein:
each $R^1$ is independently H, halogen, optionally substituted $(C_1\text{-}C_8)$alkyl, optionally substituted $(C_2\text{-}C_8)$alkenyl or optionally substituted $(C_2\text{-}C_8)$alkynyl;
each $R^2$ is independently halogen or $OR^{11}$;
each $R^5$ is H;
each $R^{22}$ is $OR^{11}$ and
the remaining variables are defined as for Formulas Ia or Ib or II or IIIa or IIIb.

In one embodiment of the method for preparing a compound of Formula VIa or Formula VIb from a compound of Formula VII, $X^1$ is $CR^{10}$. In another aspect of this embodiment, $R^{10}$ is H. In another aspect of this embodiment, $R^1$ is H. In another aspect of this embodiment, $R^1$ is F. In another aspect of this embodiment, $R^1$ is optionally substituted $(C_1\text{-}C_8)$alkyl. In another aspect of this embodiment, $R^1$ is methyl.

In another aspect of this embodiment, $R^1$ is optionally substituted $(C_2\text{-}C_8)$alkenyl. In another aspect of this embodiment, $R^1$ is optionally substituted ethenyl. In another aspect of this embodiment, $R^1$ is optionally substituted $(C_2\text{-}C_8)$alkynyl. In another aspect of this embodiment, $R^1$ is optionally substituted ethynyl. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1\text{-}C_8)$alkyl. In another aspect of this embodiment, $R^7$ is optionally substituted $(C_2\text{-}C_8)$alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted $(C_1\text{-}C_8)$alkyl. In another aspect of this embodiment, $R^6$ is optionally substituted $(C_1\text{-}C_8)$alkyl. In another aspect of this embodiment, $R^4$ is optionally substituted $(C_6\text{-}C_{20})$aryl. In another aspect of this embodiment, Ar is optionally substituted nitrophenyl.

In another embodiment of the method for preparing a compound of Formula VIa or Formula VIb from a compound of Formula VII, $X^1$ is CH, $R^1$ is H or $CH_3$ and one of $R^c$ or $R^d$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, $R^7$ is H. In another aspect of this embodiment, $R^7$ is optionally substituted $(C_1\text{-}C_8)$alkyl. In another aspect of this embodiment, $R^7$ is $CH_3$. In another aspect of this embodiment, $R^7$ is optionally substituted $(C_2\text{-}C_8)$alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted $(C_1\text{-}C_8)$alkyl. In another aspect of this embodiment, $R^6$ is optionally substituted $(C_1\text{-}C_8)$alkyl. In another aspect of this embodiment, $R^4$ is optionally substituted $(C_6\text{-}C_{20})$aryl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NR^{11}R^{12}$ and $R^9$ is $NR^{11}R^{12}$.

In another embodiment of the method for preparing a compound of Formula VIa or Formula VIb from a compound of Formula VII, $X^1$ is CH, $R^1$ is H or $CH_3$, one of $R^c$ or $R^d$ is H and $R^7$ is CN. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, one of $R^c$ or $R^d$ is H and the other of $R^c$ or $R^d$ is optionally substituted $(C_1\text{-}C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1\text{-}C_8)$allyl. In another aspect of this embodiment, $R^4$ is optionally substituted $(C_6\text{-}C_{20})$aryl. In another aspect of this embodiment, $R^4$ is optionally substituted phenyl. In another aspect of this embodiment, Ar is optionally is $NR^{11}R^{12}$. In substituted nitrophenyl. In another aspect of this embodiment, $R^8$ another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NH_2$ and $R^9$ is H. In another aspect of this embodiment, $R^8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is OH and $R^9$ is $NH_2$.

In another embodiment, provided is a method of preparing a compound of Formula IIIa or Formula IIIb

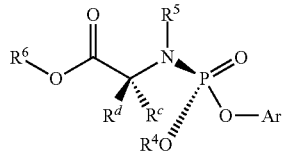

Formula IIIa

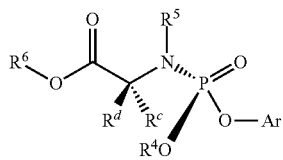

Formula IIIb wherein:

each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a $(C_6-C_{20})$ aryl or heteroaryl wherein said $(C_6-C_{20})$ aryl or heteroaryl is substituted with one or more halogen, $NO_2$, or $(C_1-C_8)$haloalkyl and optionally substituted with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2 N(R^a)_2$, $OR^a$ or $R^a$ with the proviso that Ar is different from $R^4$;

said method comprising:

(d) providing a diastereomeric compound of Formula VIII

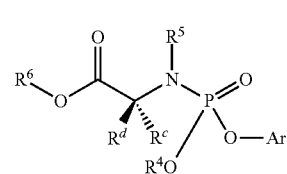

Formula VIII and (e) crystallizing the compound of Formula VIII from a suitable solvent;

thereby forming a pure diasteromer of Formula IIIa or Formula IIIb.

In one embodiment of the method of preparing a compound of Formula IIIa or Formula IIIb, $R^5$ is H and one of $R^c$ or $R^d$ is H. In another aspect of this embodiment, one of $R^c$ or $R^d$ is H and the other of $R^c$ or $R^d$ is optionally substituted $(C_1-C_8)$alkyl.

In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $(C_1-C_8)$ secondary or tertiary alkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula Ina or Formula IIIb, $R^5$ is H, one of $R^c$ or $R^d$ is H, $R^6$ is optionally substituted $(C_1-C_8)$alkyl, and $R^4$ is optionally substituted $(C_6-C_{20})$aryl. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula IIIa or Formula IIIb, $R^5$ is H, one of $R^c$ or $R^d$ is H and the other of $R^c$ or $R^d$ is optionally substituted $(C_1-C_8)$alkyl, $R^6$ is optionally substituted $(C_1-C_8)$alkyl, and $R^4$ is optionally substituted phenyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

In another embodiment of the method of preparing a compound of Formula IIIa or Formula IIIb, $R^5$ is H, one of $R^c$ or $R^d$ is H and the other of $R^c$ or $R^d$ is $CH_3$, $R^6$ is optionally substituted $(C_1-C_8)$alkyl, and $R^4$ is optionally substituted phenyl. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^6$ is 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R.

The diastereomeric mixture of the compound of Formula VIII is resolved by crystallization of the compound of Formula VIII from a suitable solvent. Non-limiting examples of suitable solvents are diethyl ether, dipropyl ether, di t-butyl ether, methyl t-butyl ether, $C_1-C_6$ halogenated alkanes, $C_5-C_8$ hydrocarbon, tetrahydrofuran, toluene, xylene, dioxane and the like. In another embodiment, the compound of Formula IV is dissolved in a suitable solvent and crystallization is induced by addition of a $C_5-C_8$ hydrocarbon or $C_5-C_8$ cyclic hydrocarbon. In a preferred embodiment, the compound of Formula VIII is dissolved in an ether solvent and crystallization is induced by addition of a $C_5-C_8$ hydrocarbon. In a particularly preferred embodiment, the compound of Formula VIII is dissolved in diethyl ether and crystallization is induced by the addition of hexane.

The diastereomeric mixture of the compound of Formula VIII is resolved by crystallization of the compound of Formula VIII from a suitable solvent at a temperature of about 80° C. to about −20° C. Preferrably, the temperature is about 30° C. to about −20° C., more preferably about ambient to −10° C.

The diastereomeric mixture of the compound of Formula VIII is resolved by crystallization of the compound of Formula VIII from a suitable solvent wherein the concentration of the compound of Formula VIII in solution is about 25 g to about 1000 g per liter of solvent. More typically, the concentration of the compound of Formula VIII is about 50 to 500 g per liter of solvent.

The resolution of the diastereomeric mixture of the compound of Formula VIII by crystallization may be promoted by the addition of seed crystals of the pure diastereomer. Seed crystals of pure diastereomers may be obtained through purification of the diastereomeric mixture of the compound of Formula VIII by liquid chromatography, chiral liquid chromatography, high pressure liquid chromatography, or chiral high pressure liquid chromatography such as by the non-limiting methods described herein.

Typically, the crystallization of the diastereomeric mixture of the compound of Formula VIII produces a mixture of diastereomers containing at least 60% of a single diastereomer. More typically, the mixture produced contains at least 70% of a single diastereomer, most typically, at least 80% of a single diastereomer, preferably at least 90% of a single diastereomer, and more preferably at least 95% of a single diastereomer. Higher diastereomeric purity, for example at least 99% diastereomeric purity, may be obtained by one or more subsequent crystallizations. The yield of crystalline material from a single crystallization is typically about 10 to 45%, more typically about 20-35%.

In another embodiment, provided is a compound of Formula IIIa or Formula IIIb

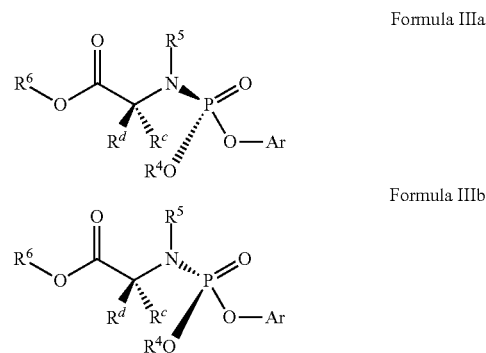

Formula IIIa

Formula IIIb or a salt or ester thereof;
wherein:

each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^c$ or $R^d$ is independently H, $(C_1-C_8)$alkyl, $(C_2-C_8)$alkenyl, $(C_2-C_3)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a $(C_6-C_{20})$ aryl or heteroaryl wherein said $(C_6-C_{20})$ aryl or heteroaryl is substituted with one or more halogen, $NO_2$, or $(C_1-C_8)$haloalkyl and optionally substituted with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$.

In another embodiment of the compound of Formula IIIa or Formula IIIb, $R^5$ is H and one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $(C_1-C_8)$ secondary or tertiary alkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

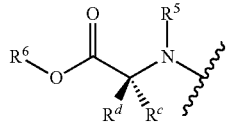

of Formula IIIa or Formula IIIb comprises a nitrogen-linked ester of a naturally occurring α-amino acid.

In another embodiment of the compound of Formula IIIa or Formula IIIb, $R^5$ is H, one of $R^c$ or $R^d$ is H, $R^6$ is optionally substituted ($C_1$-$C_8$)alkyl and $R^4$ is optionally substituted ($C_6$-$C_{20}$)aryl. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

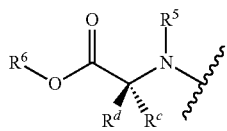

of Formula IIIa or Formula IIIb comprises a nitrogen-linked ester of a naturally occurring α-amino acid.

In another embodiment of the compound of Formula IIIa or Formula IIIb, $R^5$ is H, one of $R^c$ or $R^d$ is H and the other of $R^c$ or $R^d$ is optionally substituted ($C_1$-$C_8$)alkyl, $R^6$ is optionally substituted ($C_1$-$C_8$)alkyl and $R^4$ is optionally substituted phenyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

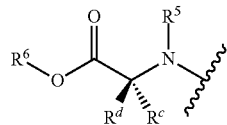

of Formula IIIa or Formula IIIb comprises a nitrogen-linked ester of a naturally occurring α-amino acid.

In another embodiment of the compound of Formula IIIa or Formula IIIb, $R^5$ is H, one of $R^c$ or $R^d$ is H and the other of $R^c$ or $R^d$ is $CH_3$, $R^6$ is optionally substituted ($C_1$-$C_8$)alkyl, and $R^4$ is optionally substituted phenyl. In another aspect of this embodiment, $R^6$ is optionally substituted ($C_1$-$C_8$) secondary or tertiary alkyl. In another aspect of this embodiment, $R^6$ is optionally substituted 2-propyl. In another aspect of this embodiment, $R^6$ is 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the moiety

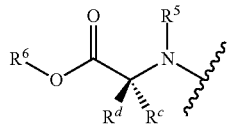

of Formula IIIa or Formula IIIb comprises a nitrogen-linked ester of a naturally occurring α-amino acid.

In another embodiment, provided are compounds of Formula IIIa or Formula IIIb selected from the group consisting of:

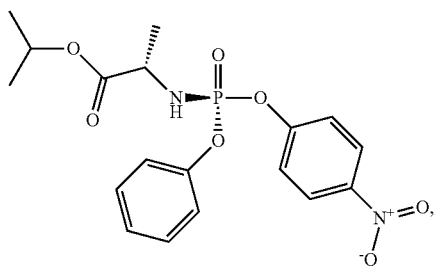

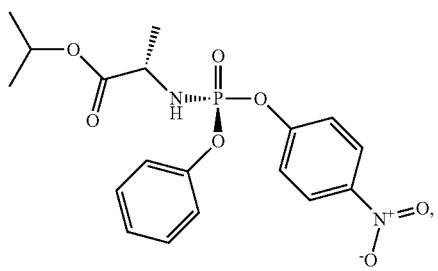

| 27 | 28 |
|---|---|
| -continued | -continued |
| 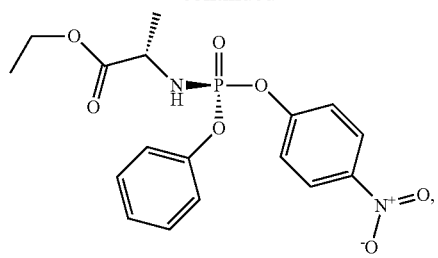 | 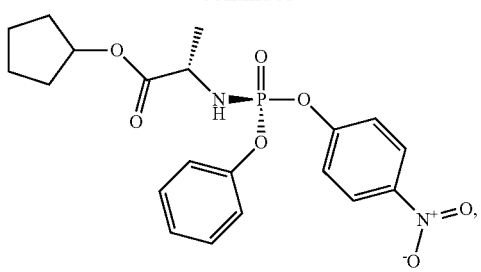 |
| 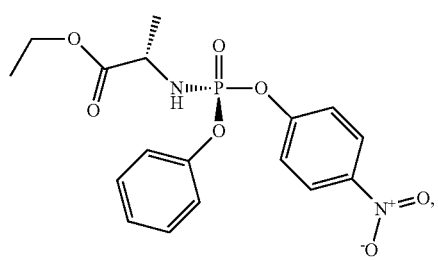 | 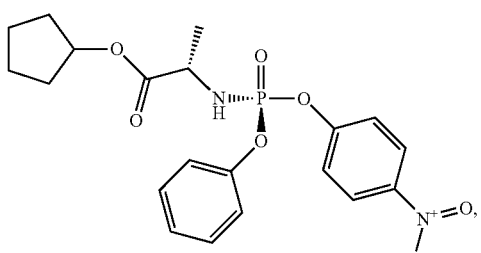 |
| 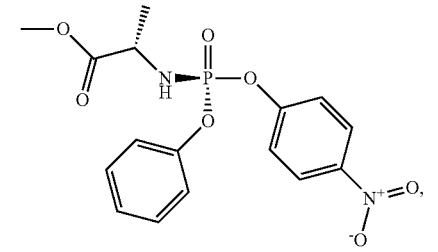 | 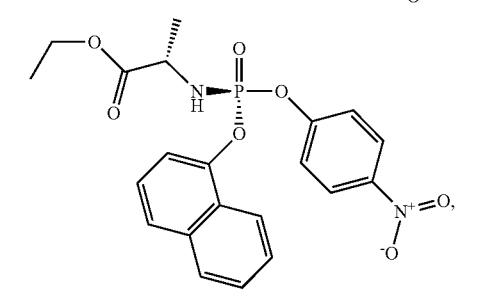 |
| 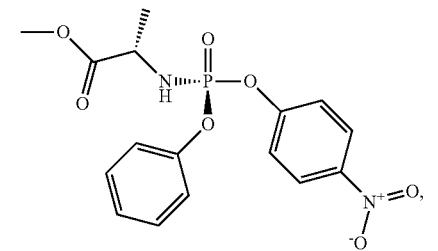 | 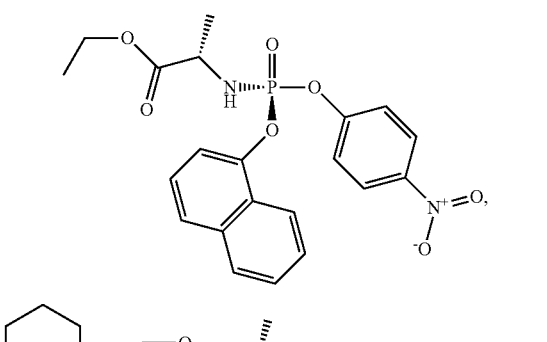 |
| 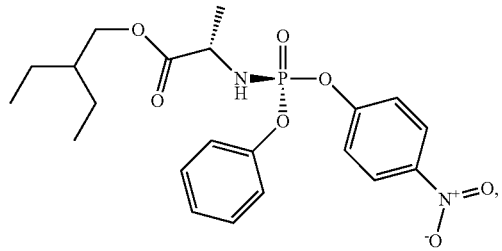 | 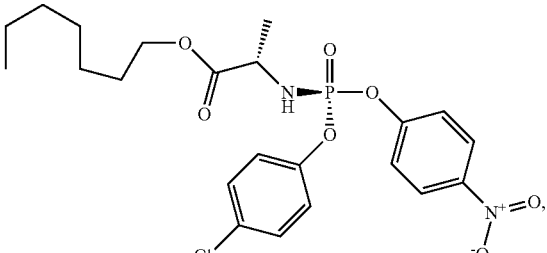 |
| 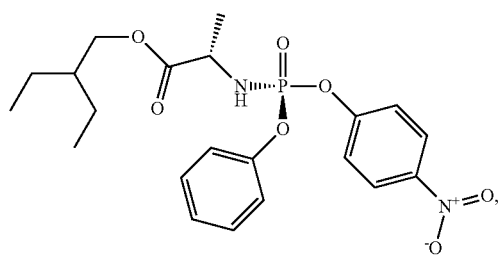 | 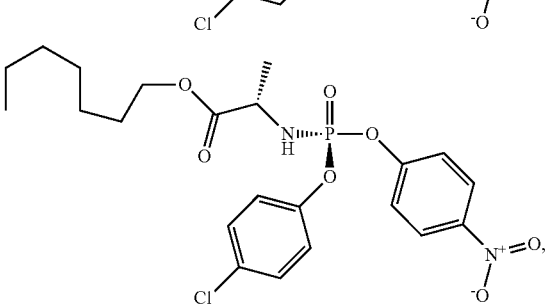 |

-continued

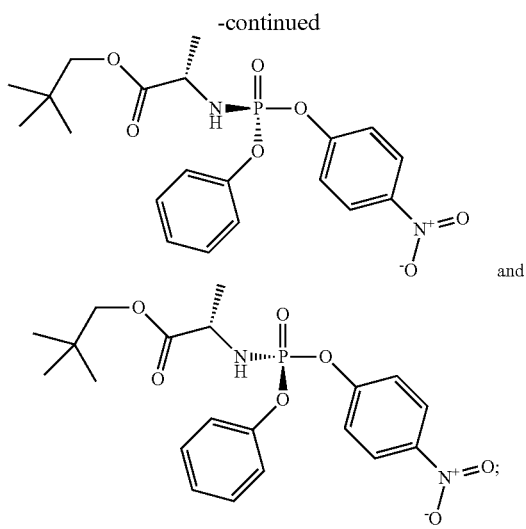

and

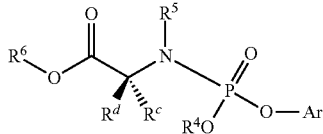

or salts or esters thereof.

In another embodiment, provided is a method of preparing a compound of Formula VIII

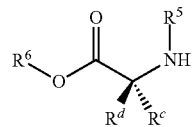

Formula VIII wherein each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a $(C_6-C_{20})$ aryl or heteroaryl wherein said $(C_6-C_{20})$ aryl or heteroaryl is substituted with one or more halogen, $NO_2$, or $(C_1-C_8)$haloalkyl and optionally substituted with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$;

said method comprising:

(f) providing a chirally pure amino acid ester of Formula IX or a salt thereof

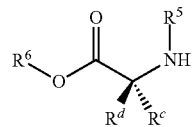

Formula IX (g) treating the compound of Formula IX with a compound of Formula X in the presence of a base

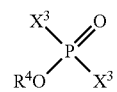

Formula X wherein each $X^3$ is halogen; and (h) treating the resulting mixture with ArOH;

thereby forming a compound of Formula VIII.

Typically, the chirally pure amino acid of Formula IX or a salt thereof is dissolved or suspended in a suitable non-nucleophilic solvent. Non-limiting non-nucleophilic solvents include haloalkanes, e.g., methylene chloride, dichloroethane and ethers, e.g. dioxane, tetrahydrofuran and glymes. Typically, the suspension or solution contains about 0.1 to about 5 moles of the compound of Formula IX per liter of solvent.

The suspension or solution of the chirally pure amino acid of Formula IX is treated with a compound of Formula X. Typically, the reaction is conducted at about −20 to about 60° C. The mole ratio of the compound of Formula IX to the compound of Formula X is about 1:2 to about 2:1, preferably about 1:1. The reaction is conducted in the presence of a non-nucleophilic base. Non-limiting examples of non-nucleophilic bases are tertiary amines, e.g. triethylamine, diisopropylethylamine and triethylamine; metal hydrides, e.g. LiH, NaH and $CaH_2$; and nitrogen containing heterocycles, e.g. pyridine and dimethylaminopyridine. In a preferred embodiment, the base is a tertiary amine such as triethylamine. When the compound of Formula IX is a salt of a mono-protic acid, the mole ratio of base to the compound of Formula IX is typically about 2:1. If the compound of Formula IX is a free base, the mole ratio of base to the compound of Formula IX is about 1:1.

The reaction of the compound of Formula IX with the compound of Formula X may be followed by many conventional means known to those skilled in the art. Such means include thin-layer chromatography and hplc. When the reaction between the compound Formula IX and the compound of Formula X is complete, the reaction is treated with a phenolic compound ArOH where Ar is defined as herein. The mole ratio of the compound of Formula X to ArOH is about 1.1:1 to about 1:1.1, preferably about 1:1. After the addition of ArOH, additional base is required, typically enough base to neutralize the acid generated in the reaction. Typically, the additional base is a non-nucleophilic base such as described above.

The compound of Formula VIII is isolated by conventional means known to those skilled in the art. For example, the salt formed in the reaction may be precipitated from the reaction mixture and the compound of Formula VIII isolated by evaporation of the solvent followed by crystallization or chromatography.

In one embodiment of the method of preparing a compound of Formula VIII, $R^5$ is H and one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^6$ is optionally substituted $(C_1-C_8)$ secondary or tertiary alkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method of preparing a compound of Formula VIII, $R^5$ is H, one of $R^c$ or $R^d$ is H, $R^6$ is optionally substituted $(C_1-C_8)$alkyl, and $R^4$ is optionally substituted $(C_6-C_{20})$aryl. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is optionally substituted phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method of preparing a compound of Formula VIII, $R^5$ is H, one of $R^c$ or $R^d$ is H and the other of $R^c$ or $R^d$ is optionally substituted $(C_1-C_8)$alkyl, $R^6$ is optionally substituted $(C_1-C_8)$alkyl, and $R^4$ is optionally substituted phenyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method of preparing a compound of Formula VIII, $R^5$ is H, one of $R^c$ or $R^d$ is H and the other of $R^c$ or $R^d$ is $CH_3$, $R^6$ is optionally substituted $(C_1-C_8)$ alkyl, and $R^4$ is optionally substituted phenyl. In another aspect of this embodiment, $R^6$ is optionally substituted $(C_1-C_8)$ secondary or tertiary alkyl. In another aspect of this embodiment, $R^6$ is optionally substituted 2-propyl. In another aspect of this embodiment, $R^6$ is 2-propyl. In another aspect of this embodiment, $R^4$ is phenyl. In another aspect of this embodiment, Ar is optionally substituted nitrophenyl. In another aspect of this embodiment, Ar is optionally substituted para-nitrophenyl. In another aspect of this embodiment, Ar is para-nitrophenyl. In another aspect of this embodiment, the chirality at the carbon directly attached to $R^c$ and $R^d$ is S. In another aspect of this embodiment, the chirality at the carbon directly attached to $R^c$ and $R^d$ is R. In another aspect of this embodiment, the compound of Formula IX or salt thereof, is an ester of a naturally occurring α-amino acid.

In another embodiment of the method for preparing a compound of Formula Ia or Ib or a pharmaceutically acceptable salt or ester thereof, Formula Ia is Formula XIa, Formula Ib is Formula XIb and Formula II is Formula XII:

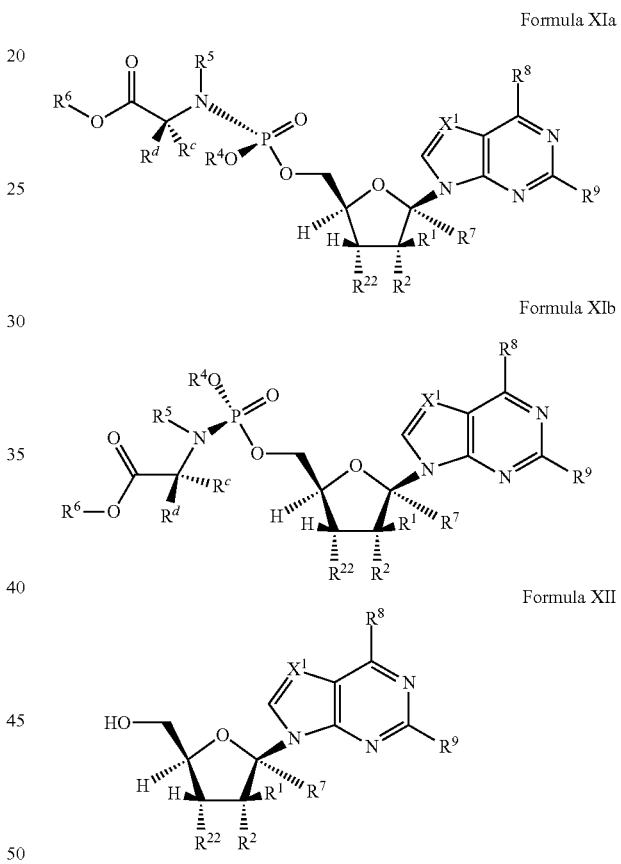

Formula XIa

Formula XIb

Formula XII wherein:
each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H;
each $R^{22}$ is $OR^{11}$ and the remaining variables are defined as for Formulas Ia or Ib or II or IIIa or IIIb.

In one embodiment of the method for preparing a compound of Formula XIa or Formula XIb from a compound of Formula XII, $X^1$ is $CR^{10}$. In another aspect of this embodiment, $R^{10}$ is H. In another aspect of this embodiment, $R^1$ is H. In another aspect of this embodiment, $R^1$ is F. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted ($C_2$-$C_8$)alkenyl. In another aspect of this embodiment, $R^1$ is optionally substituted ethenyl. In another aspect of this embodiment, $R^1$ is optionally substituted ($C_2$-$C_8$)alkynyl. In another aspect of this embodiment, $R^1$ is optionally substituted ethynyl. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is optionally substituted ($C_2$-$C_8$)alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl.

In another embodiment of the method for preparing a compound of Formula XIa or Formula XIb from a compound of Formula XII, $X^1$ is CH, $R^1$ is H or $CH_3$ and one of $R^c$ or $R^d$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is $CH_3$. In another aspect of this embodiment, $R^7$ is optionally substituted ($C_2$-$C_8$)alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NR^{11}R^{12}$ and $R^9$ is $NR^{11}R^{12}$.

In another embodiment of the method for preparing a compound of Formula XIa or Formula XIb from a compound of Formula XII, $X^1$ is CH, $R^1$ is H or $CH_3$, one of $R^c$ or $R^d$ is H and $R^7$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, $R^4$ is optionally substituted phenyl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NH_2$ and $R^9$ is H. In another aspect of this embodiment, $R^8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is $OR^{11}$ and $R^9$ is $NH_2$. In another aspect of this embodiment, $R^8$ is OH and $R^9$ is $NH_2$.

In one embodiment of the method for preparing a compound of Formula XIa or Formula XIb from a compound of Formula XII, $X^1$ is N. In another aspect of this embodiment, $R^1$ is H. In another aspect of this embodiment, $R^1$ is F. In another aspect of this embodiment, $R^1$ is optionally substituted ($C_1$-$C_8$)alkyl. In another aspect of this embodiment, $R^1$ is methyl. In another aspect of this embodiment, $R^1$ is optionally substituted ($C_2$-$C_8$)alkenyl. In another aspect of this embodiment, $R^1$ is optionally substituted ethenyl. In another aspect of this embodiment, $R^1$ is optionally substituted ($C_2$-$C_8$)alkynyl. In another aspect of this embodiment, $R^1$ is optionally substituted ethynyl. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is optionally substituted ($C_2$-$C_8$)alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl.

In another embodiment of the method for preparing a compound of Formula XIa or Formula XIb from a compound of Formula XII, $X^1$ is N, $R^1$ is H or $CH_3$ and one of $R^c$ or $R^d$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is $CH_3$. In another aspect of this embodiment, $R^7$ is optionally substituted ($C_2$-$C_8$)alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$.

In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NR^{11}R^{12}$ and $R^9$ is $NR^{11}R^{12}$.

In another embodiment of the method for preparing a compound of Formula XIa or Formula XIb from a compound of Formula XII, $X^1$ is N, $R^1$ is H or $CH_3$, one of $R^c$ or $R^d$ is H and $R^7$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, one of $R^c$ or $R^d$ is H and the other of $R^c$ or $R^d$ is optionally substituted $(C_1-C_8)$alkyl. In another aspect of this embodiment, one of $R^c$ or $R^d$ is H and the other of $R^c$ or $R^d$ is $CH_3$. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, $R^4$ is optionally substituted phenyl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH. In another aspect of this embodiment, $R^9$ is H. In another aspect of this embodiment, $R^9$ is $NR^{11}R^{12}$. In another aspect of this embodiment, $R^9$ is $OR^{11}$. In another aspect of this embodiment, $R^8$ is $NR^{11}R^{12}$ and $R^9$ is H. In another aspect of this embodiment, $R^8$ is $NH_2$ and $R^9$ is H. In another aspect of this embodiment, $R^8$ is $NR^{11}R^{12}$ and $R^9$ is $NR^{11}R^{12}$. In another aspect of this embodiment, $R^8$ is $NH_2$ and $R^9$ is $NH_2$. In another aspect of this embodiment, $R^8$ is $OR^{11}$ and $R^9$ is $NH_2$. In another aspect of this embodiment, $R^8$ is OH and $R^9$ is $NH_2$.

In another embodiment of the method for preparing a compound of Formula Ia or Ib or a pharmaceutically acceptable salt or ester thereof, Formula Ia is Formula XIIIa, Formula Ib is Formula XIIIb and Formula II is Formula XIV:

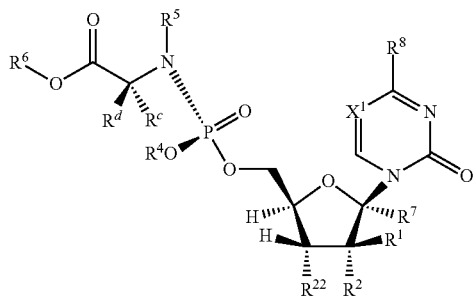

Formula XIIIa

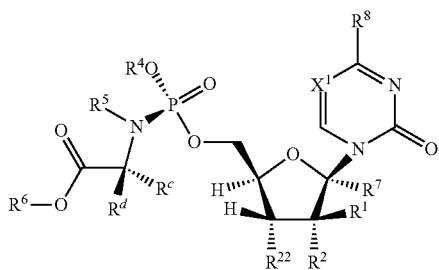

Formula XIIIb

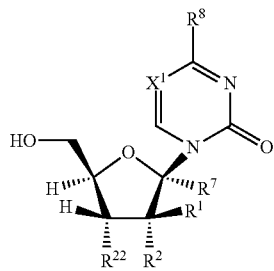

Formula XIV wherein:
each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H;
each $R^{22}$ is $OR^{11}$ and
the remaining variables are defined as for Formulas Ia or Ib or II or IIIa or IIIb.

In one embodiment of the method for preparing a compound of Formula XIIIa or Formula XIIIb from a compound of Formula XIV, $X^1$ is $CR^{10}$. In another aspect of this embodiment, $R^{10}$ is H. In another aspect of this embodiment, $R^{10}$ is $CH_3$. In another aspect of this embodiment, $R^1$ is H. In another aspect of this embodiment, $R^1$ is F. In another aspect of this embodiment, $R^1$ is optionally substituted $(C_1-C_8)$alkyl. In another aspect of this embodiment, $R^1$ is methyl. In another aspect of this embodiment, $R^1$ is optionally substituted $(C_2-C_8)$alkenyl. In another aspect of this embodiment, $R^1$ is optionally substituted ethenyl. In another aspect of this embodiment, $R^1$ is optionally substituted $(C_2-C_8)$alkynyl. In another aspect of this embodiment, $R^1$ is optionally substituted ethynyl. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is optionally substituted $(C_2-C_8)$alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted $(C_1-C_8)$alkyl. In another aspect of this embodiment, $R^6$ is optionally substituted $(C_1-C_8)$alkyl. In another aspect of this embodiment, $R^4$ is optionally substituted $(C_6-C_{20})$aryl. In another aspect of this embodiment, Ar is optionally substituted nitrophenyl.

In another embodiment of the method for preparing a compound of Formula XIIIa or Formula XIIIb from a compound of Formula XIV, $X^1$ is CH, $R^1$ is H or $CH_3$ and one of $R^c$ or $R^d$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted $(C_1-C_8)$alkyl. In another aspect of this embodiment, $R^7$ is $CH_3$. In another aspect of this embodiment, $R^7$ is optionally substituted $(C_2-C_8)$alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In another embodiment of the method for preparing a compound of Formula XIIIa or Formula XIIIb from a compound of Formula XIV, $X^1$ is CH, $R^1$ is H or $CH_3$, one of $R^c$ or $R^d$ is H and $R^7$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, $R^4$ is optionally substituted phenyl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In one embodiment of the method for preparing a compound of Formula XIIIa or Formula XIIIb from a compound of Formula XIV, $X^1$ is CF. In another aspect of this embodiment, $R^1$ is H. In another aspect of this embodiment, $R^1$ is F. In another aspect of this embodiment, $R^1$ is optionally substituted ($C_1$-$C_8$)alkyl. In another aspect of this embodiment, $R^1$ is methyl. In another aspect of this embodiment, $R^1$ is optionally substituted ($C_2$-$C_8$)alkenyl. In another aspect of this embodiment, $R^1$ is optionally substituted ethenyl. In another aspect of this embodiment, $R^1$ is optionally substituted ($C_2$-$C_8$)alkynyl. In another aspect of this embodiment, $R^1$ is optionally substituted ethynyl. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is optionally substituted ($C_2$-$C_8$)alkynyl. In another aspect of this embodiment, $R^7$ is CN. In another aspect of this embodiment, one of $R^c$ or $R^d$ is H. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl.

In another embodiment of the method for preparing a compound of Formula XIa or Formula XIb from a compound of Formula XII, $X^1$ is CF, $R^1$ is H or $CH_3$ and one of $R^c$ or $R^d$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, $R^7$ is H. In another aspect of this embodiment, $R^7$ is optionally substituted ($C_1$-$C_8$)alkyl. In another aspect of this embodiment, $R^7$ is $CH_3$. In another aspect of this embodiment, $R^7$ is optionally substituted ($C_2$-$C_8$)alkynyl. In another aspect of this embodiment, $R^7$ is ethynyl. In another aspect of this embodiment, $R^7$ is CN. In another aspect of this embodiment, one of $R^c$ or $R^d$ is H and the other of $R^c$ or $R^d$ is optionally substituted ($C_1$-$C_8$)alkyl. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

In another embodiment of the method for preparing a compound of Formula XIIIa or Formula XIIIb from a compound of Formula XIV, $X^1$ is CF, $R^1$ is H or $CH_3$, one of $R^c$ or $R^d$ is H and $R^7$ is H. In another aspect of this embodiment, $R^2$ is F. In another aspect of this embodiment, $R^2$ is OH. In another aspect of this embodiment $R^{22}$ is OH. In another aspect of this embodiment, each $R^2$ and $R^{22}$ is OH. In another aspect of this embodiment, each $R^2$ is F and $R^{22}$ is OH. In another aspect of this embodiment, one of $R^c$ or $R^d$ is H and the other of $R^c$ or $R^d$ is optionally substituted ($C_1$-$C_8$)alkyl. In another aspect of this embodiment, one of $R^c$ or $R^d$ is H and the other of $R^c$ or $R^d$ is $CH_3$. In another aspect of this embodiment, $R^6$ is optionally substituted ($C_1$-$C_8$)alkyl. In another aspect of this embodiment, $R^4$ is optionally substituted ($C_6$-$C_{20}$)aryl. In another aspect of this embodiment, $R^4$ is optionally substituted phenyl. In another aspect of this embodiment, Ar is optionally substituted nitrophenyl. In another aspect of this embodiment, $R^8$ is $NR^{11}R^{12}$. In another aspect of this embodiment, $R^8$ is $OR^{11}$. In another aspect of this embodiment, $R^8$ is $NH_2$. In another aspect of this embodiment, $R^8$ is OH.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., C$_1$-C$_{20}$ alkoxy), 1 to 12 carbon atoms (i.e., C$_1$-C$_{12}$ alkoxy), or 1 to 6 carbon atoms (i.e., C$_1$-C$_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., C$_1$-C$_{20}$ haloalkyl), 1 to 12 carbon atoms (i.e., C$_1$-C$_{12}$ haloalkyl), or 1 to 6 carbon atoms (i.e., C$_1$-C$_6$ alkyl). Examples of suitable haloalkyl groups include, but are not limited to, —CF$_3$, —CHF$_2$, —CFH$_2$, —CH$_2$CF$_3$, and the like.

"Alkenyl" is a hydrocarbon containing normal, secondary, tertiary or cyclic carbon atoms with at least one site of unsaturation, i.e. a carbon-carbon, sp$^2$ double bond. For example, an alkenyl group can have 2 to 20 carbon atoms (i.e., C$_2$-C$_{20}$ alkenyl), 2 to 8 carbon atoms (i.e., C$_2$-C$_8$ alkenyl), or 2 to 6 carbon atoms (i.e., C$_2$-C$_6$ alkenyl). Examples of suitable alkenyl groups include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., C$_2$-C$_{20}$ alkynyl), 2 to 8 carbon atoms (i.e., C$_2$-C$_8$ alkyne,), or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^a$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means, unless otherwise stated, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b_2$, N$^+$R$^b_3$, NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b_2$, —S(=O)$_2$—, —S(=O)$_2$OH, —S(=O)$_2$R$^b$, —OS(=O)$_2$OR$^b$, —S(=O)$_2$NR$^b_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b_2$, —C(S)NR$^b_2$, —C(=NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-XIV should be selected in order to provide a compound which is sufficiently stable to provide a pharmaceutically useful compound which can be formulated into an acceptably stable pharmaceutical composition. Compounds of Formula I-XIV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

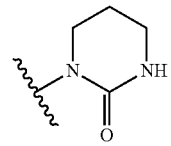

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

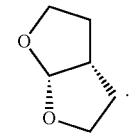

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

The term "purine" or "pyrimidine" base comprises, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-5-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Additional non-classical purine bases include pyrrolo[1,2-f][1,2,4]triazines, imidazo[1,5-f][1,2,4]triazines, imidazo[1,2-f][1,2,4]triazines, and [1,2,4]triazolo[4,3-f][1,2,4]triazines, all of which are optionally substituted. The purine and pyrimidine bases of Formula II are linked to the ribose sugar, or analog thereof, through a nitrogen atom or carbon atom of the base. Functional oxygen and nitrogen groups on the base can be protected as necessary or desired. Suitable protecting groups are well known to those skilled in the art, and include, but are not limited to, trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I-XIV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-XIV (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Some embodiments of the compounds of Formula I-XIV comprise the moiety

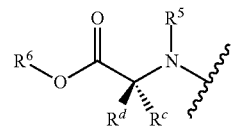

which may comprise a radical of a nitrogen-linked ester of a naturally occurring α-amino acid. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substitutent R$^6$, particularly those in which R$^6$ is optionally substituted (C$_1$-C$_8$)alkyl.

Unless otherwise specified, the carbon atoms of the compounds of Formula I-XIV are intended to have a valence of four. In some chemical structure representations where carbon atoms do not have a sufficient number of variables attached to produce a valence of four, the remaining carbon substitutents needed to provide a valence of four should be assumed to be hydrogen. For example,

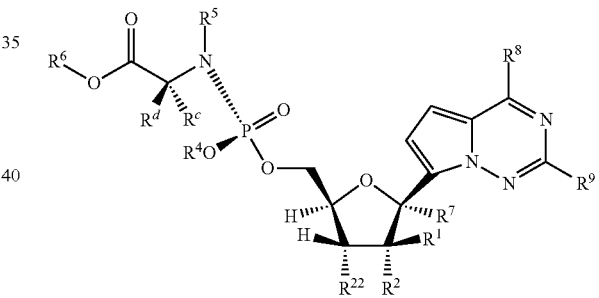

has the same meaning as

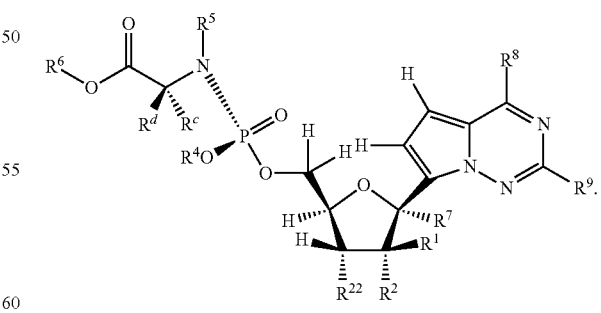

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself The phosphate group may be a phosphate prodrug moiety. The prodrug moiety may be sensitive to hydrolysis. Alternatively, the prodrug moiety may be sensitive to enzymatic cleavage, such as a lactate ester or a phosphonamidate-ester group.

It is to be noted that all enantiomers, diastereomers, and racemic mixtures, tautomers, polymorphs, pseudopolymorphs of compounds within the scope of Formula I-IV and pharmaceutically acceptable salts thereof are embraced by the present invention. All mixtures of such enantiomers and diastereomers are within the scope of the present invention.

A compound of Formula I-XIV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-IV and their pharmaceutically acceptable salts.

A compound of Formula I-XIV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IV and their pharmaceutically acceptable salts.

Selected substituents comprising the compounds of Formula I-XIV are present to a recursive degree. In this context, "recursive substituent" means that a substituent may recite another instance of itself. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents are an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The modifier "about" used in connection with a quantity is inclusive of the stated value and has the meaning dictated by the context (e.g., includes the degree of error associated with measurement of the particular quantity).

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR^a_4{}^+$ (wherein $R^a$ is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as Na$^+$ and NR$^a_4{}^+$.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

The compounds of the invention, exemplified by Formula I-XIV have chiral centers, e.g. chiral carbon or phosphorus atoms. For example, the phosphorous atoms of Formula I-XIV may be chiral because they have four different substituents. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-XIV may have a chiral phosphorus atom when phosphorus has four different substitutents, e.g., Formula XIV, where the chirality is R or S. When R$^c$ and R$^d$ of the amino acid of the phosphoramidate of Formula IV are different, there are two centers of chirality in the molecule leading to potential diastereomeric mixtures of compounds, e.g. R,S; S,R; S,S and R,R isomers. Mixtures of diastereomers may be separate under high resolution analytical procedures such as electrophoresis, crystallization and/or chromatography. Diastereomeres may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R$^a$" or "R$^1$", then it will be understood that the groups may be the same or different, i.e., each group is independently selected. Wavy lines, ⌇⌇⌇⌇, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that nucleoside bases such as the pyrrolo[1,2-f][1,2,4]triazine nucleosides can exist in tautomeric forms. For example, but not by way of limitation, structures (a) and (b) can have equivalent tautomeric forms as shown below:

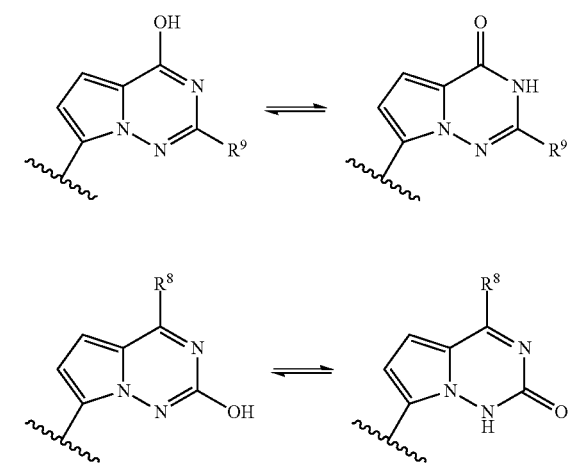

-continued

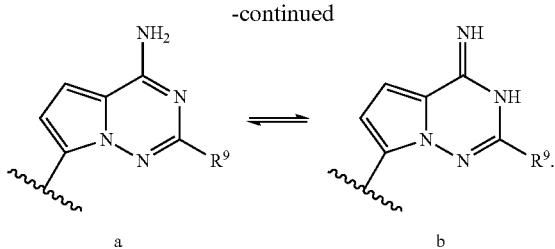

All possible tautomeric forms of the heterocycles and nucleobases in all of the embodiments disclosed herein are within the scope of the invention.

The compounds of Formula I-XIV also include molecules that incorporate isotopes of the atoms specified in the particular molecules. Non-limiting examples of these isotopes include D, T, $^{14}$C, $^{13}$C and $^{15}$N. All such isotopic variations of these molelcules are provided by the instant invention.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac$_2$O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]nonene-5 |
| DDQ | 2,3-dichloro-5,6-dicyano-1,4-benzoquinone |
| DBU | 1,5-diazabicyclo[5.4.0]undecene-5 |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH$^+$ | mass plus 1 |
| MH$^-$ | mass minus 1 |
| MsOH | methanesulfonic acid |
| MS or ms | mass spectrum |
| NBS | N-bromosuccinimide |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TEA | triethylamine |

TABLE 1-continued

List of abbreviations and acronyms.

| Abbreviation | Meaning |
|---|---|
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| δ | parts per million down field from tetramethylsilane |

Preparation of Compounds

Compound 1a-1f

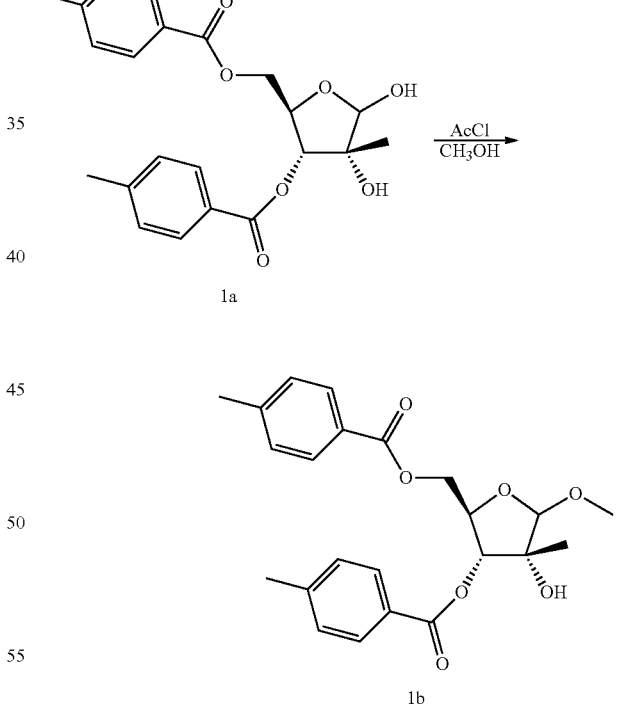

To a solution of 1a (22.0 g, 54.9 mmol, prepared according to the procedures described in J.O.C., 2004, 6257) in methanol (300 mL) was dropwise added acetyl chloride (22 mL) at 0° C. using a dropping funnel over a period of 30 min. and then stirred at room temperature for 16 h. The mixture was concentrated, re-dissolved in ethyl acetate (400 mL), washed with ice-cold 2 N NaOH, and concentrated to dryness, affording the crude methyl ether 1b as an oil. MS=437.2 (M+Na$^+$).

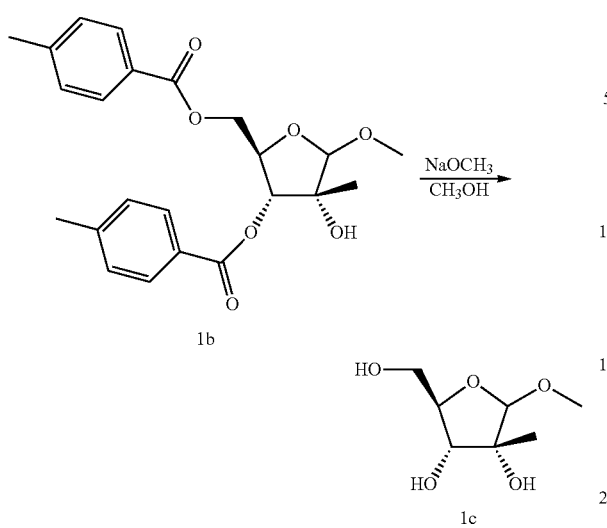

To a solution of 1b (obtained from the previous step) in methanol (300 mL) was added 0.5 M sodium methoxide solution in methanol (20 mL, 10 mmol), and stirred for 16 h at room temperature. The reaction was quenched with 4.0 N HCl solution in dioxane (2.5 mL, 10 mmol). The mixture was then concentrated, affording the crude 1c. MS=201.0 (M+Na$^+$).

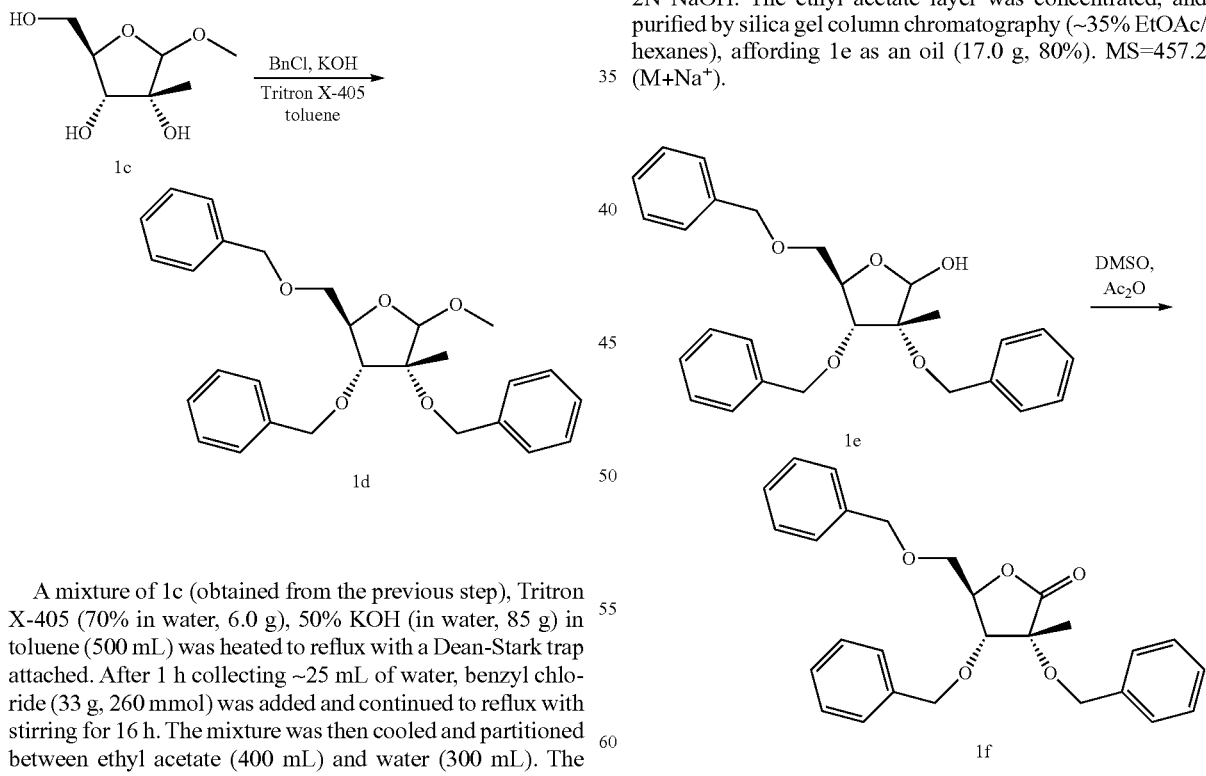

A mixture of 1c (obtained from the previous step), Tritron X-405 (70% in water, 6.0 g), 50% KOH (in water, 85 g) in toluene (500 mL) was heated to reflux with a Dean-Stark trap attached. After 1 h collecting ~25 mL of water, benzyl chloride (33 g, 260 mmol) was added and continued to reflux with stirring for 16 h. The mixture was then cooled and partitioned between ethyl acetate (400 mL) and water (300 mL). The organic layer was washed with water (300 mL), and concentrated. The residue was purified by silica gel column chromatography (~20% EtOAc/hexanes), affording the methyl ether 1d as an oil (22.0 g, 89% in three steps). $^1$H NMR (300 MHz, CDCl$_3$): δ 7.3 (m, 15H), 4.5-4.9 (m, 7H), 4.37 (m, 1H), 3.87 (d, 1H), 3.56 (m, 2H), 3.52 (s, 3H), 1.40 (s, 3H).

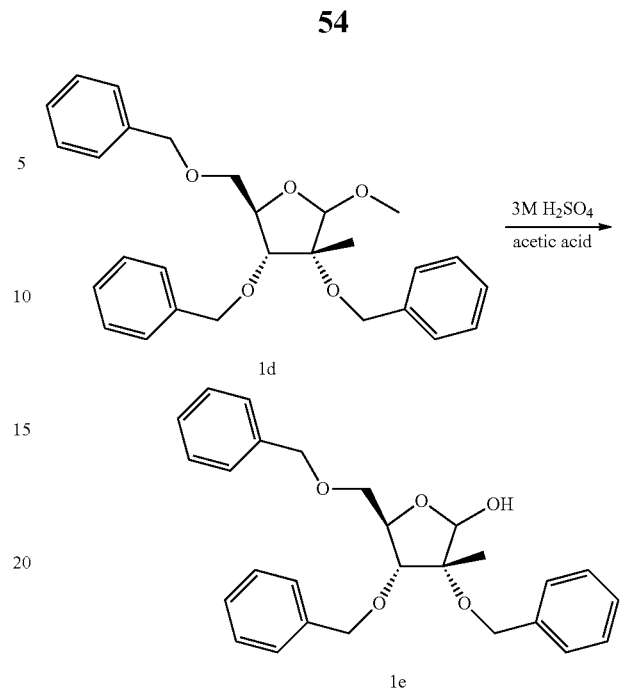

To a solution of 1d (22.0 g, 49.0 mmol) in acetic acid (110 mL) was added ~3 M sulfuric acid (prepared by mixing 4.8 g of concentrated sulfuric acid with 24 mL of water) and stirred at 70° C. for 8 h. The mixture was concentrated to a volume of ~20 mL, and partitioned between ethyl acetate and ice-cold 2N NaOH. The ethyl acetate layer was concentrated, and purified by silica gel column chromatography (~35% EtOAc/hexanes), affording 1e as an oil (17.0 g, 80%). MS=457.2 (M+Na$^+$).

To a solution of 1e (45 g, 104 mmol) in DMSO (135 mL) was dropwise added acetic anhydride (90 mL, 815 mmol) at room temperature under argon. The mixture was stirred for 16 h at room temperature, and then poured into ice-water (1 L) while stirring. After ice was completely melted (~30 min), ethyl acetate (~500 mL) was added. The organic layer was separated. This extraction process was repeated three times (3×500 mL). The organic extracts were combined and concentrated. The residue was purified by silica gel column chromatography (~20% EtOAc/hexanes), affording 1f as an oil (39 g, 88%). $^1$H NMR (300 MHz, DMSO-d$_6$): δ 7.3 (m, 15H), 4.4-4.8 (m, 7H), 4.08 (d, J=7.5 Hz, 1H), 3.75 (dd, J=2, 4, 11.4 Hz, 1H), 3.64 (dd, J=5.4, 11.4 Hz, 1H), 1.51 (s, 3H).

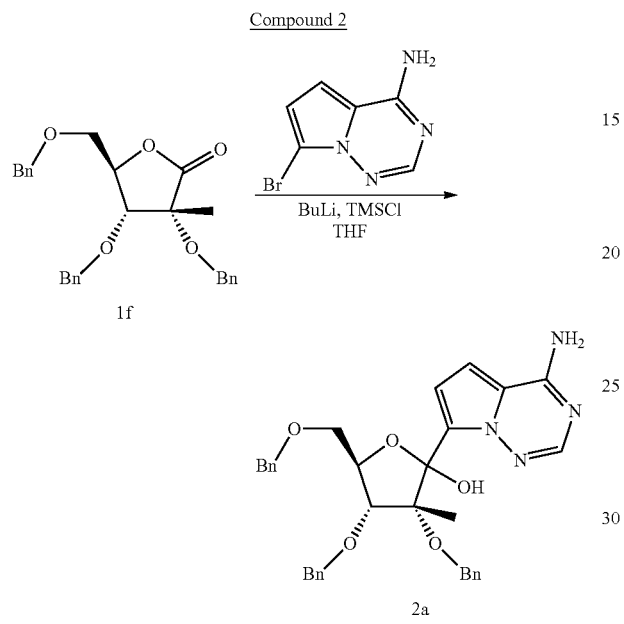

Compound 2

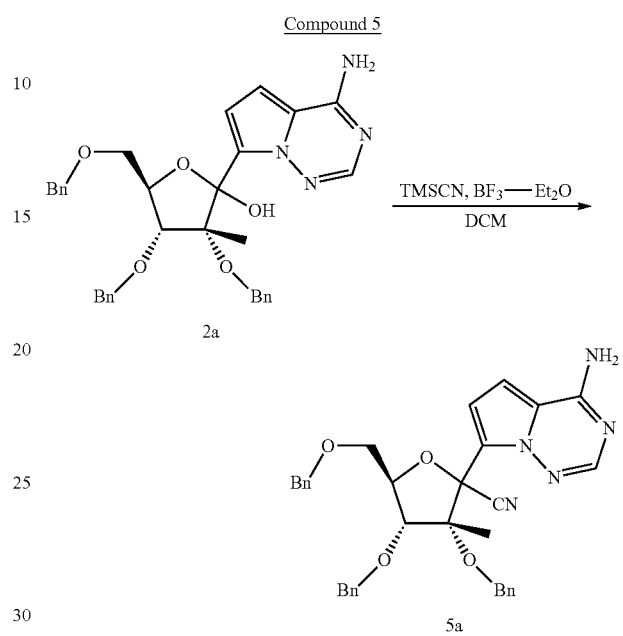

Compound 5

To a dry, argon purged round bottom flask (100 mL) were added 7-bromo-pyrrolo[2,1-f][1,2,4]triazin-4-ylamine (234 mg, 1.10 mmol) (prepared according to WO2007056170) and anhydrous THF (1.5 mL). TMSCl (276 µL, 2.2 mmol) was then added and the reaction mixture stirred for 2 h. The flask was placed into a dry ice/acetone bath (~–78° C.) and BuLi (2.5 mL, 4.0 mmol, 1.6M in hexanes) was added dropwise. After 1 h, a solution of 1f (432.5 mg, 1.0 mmol) in THF was cooled to 0° C. and then added to the reaction flask dropwise. After 1 h of stirring at –78° C., the flask was warmed to 0° C. and sat. NH$_4$Cl (5 mL) was added to quench the reaction. The organics were extracted using EtOAc (3×10 mL) and the combined organic layers were dried using MgSO$_4$. The solvent was removed under reduced pressure and the crude material was purified using flash chromatography (hexanes/EtOAc). 560 mg (90%) of 2a was isolated as a mixture of two anomers. LC/MS=567.2 (M+H$^+$). $^1$H NMR (300 MHz, CDCl$_3$): δ 7.85 (m, 1H), 7.27 (m, 15H), 7.01 (m, 1H), 6.51 (m, 1H), 4.66 (m, 8H), 4.40 (m, 2H), 3.79 (m, 3H), 1.62 (s, 2'-CH$_3$ from the one anomer), 1.18 (s, 2'-CH$_3$ from the other anomer).

Alternative Procedures for 2a

To a dry, argon purged round bottom flask were added 7-bromo-pyrrolo[2,1-f][1,2,4]triazin-4-ylamine (9.6 g, 45 mmol) and anhydrous THF (60 mL). TMSCl (12.4 mL, 99 mmol) was then added and the reaction mixture stirred for 2 h. The flask was placed into a dry ice/acetone bath (~–78° C.) and BuLi (98 mL, 158 mmol, 1.6M in hexanes) was added dropwise. After 1 h, this reaction mixture was added to a solution of 1f (13.0 g, 30 mmol) in THF at –78° C. via cannula. After 2 h of stirring at –78° C., the flask was warmed to 0° C. Saturated NH$_4$Cl (150 mL) was added to quench the reaction. The organics were extracted using EtOAc (3×100 mL) and the combined organic layers were dried using MgSO$_4$. The solvent was removed under reduced pressure and the crude material was purified using flash silica gel chromatography (hexanes/EtOAc). 7.5 g (44%) of the desired material 2a was isolated. LC/MS=567.2 (M+H$^+$).

To a solution of compound 2a (1 g, 1.77 mmol) in CH$_2$Cl$_2$ (20 mL) at 0° C. was added TMSCN (1.4 mL, 10.5 mmol) and BF$_3$-Et$_2$O (1 mL, 8.1 mmol). The reaction mixture was stirred at 0° C. for 0.5 h, then at room temperature for additional 0.5 h. The reaction was quenched with NaHCO$_3$ at 0° C., and diluted with CH$_3$CO$_2$Et. The organic phase was separated, washed with brine, dried over Na$_2$SO$_4$, filtered and concentrated. The residue was purified by chromatography on silica gel, eluted with CH$_3$CO$_2$Et-hexanes (1:1 to 2:1), to give the desired compound 5a (620 mg, 61%) as an isomeric mixture. MS=576.1 (M+H$^+$).

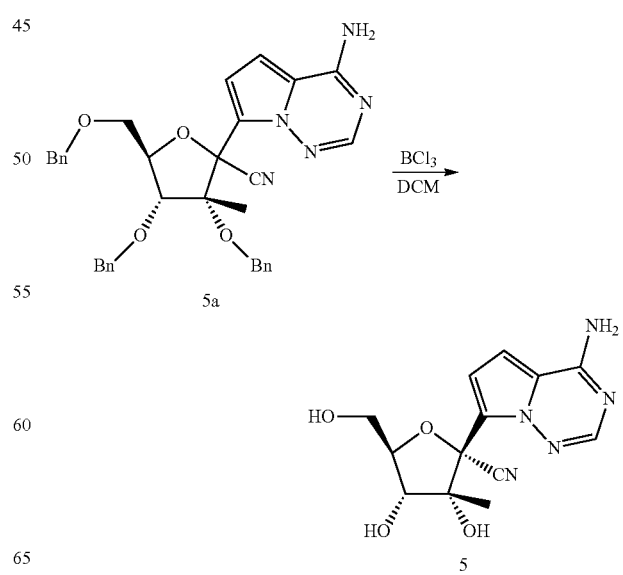

To a solution of compound 5a (150 mg, 0.26 mmol) in CH$_2$Cl$_2$ (4 mL) at −78° C. was added BCl$_3$ (2 mL, 1M in CH$_2$Cl$_2$). The reaction mixture was stirred at −78° C. for 1 h. The reaction was quenched at −78° C. by dropwise addition of TEA (2 mL) and MeOH (5 mL). The mixture was allowed to warm up to room temperature, evaporated, and co-evaporated with MeOH several times. The residue was treated with NaHCO$_3$ (1 g in 10 mL H$_2$O), concentrated and purified by HPLC to give the desired product Compound 5 (48 mg, 60%). $^1$H NMR (300 MHz, D$_2$O): δ 7.74 (s 1H), 6.76 (d, J=5 Hz, 1H), 6.73 (d, J=5 Hz, 1H), 4.1 (m, 1H), 3.9 (m, 1H), 3.8 (m, 2H), 0.84 (s, 3H). MS=305.9 (M+H$^+$). The other alpha-anomer was also obtained (9 mg, 11%): $^1$H NMR (300 MHz, D$_2$O): δ 7.70 (s 1H), 6.8 (d, J=5 Hz, 1H), 6.7 (d, J=5 Hz, 1H), 4.25 (d, J=9 Hz, 1H), 4.07 (m, 1H), 3.85 (m, 1H), 3.7 (m, 1H), 1.6 (s, 3H). MS=306.1 (M+H$^+$).

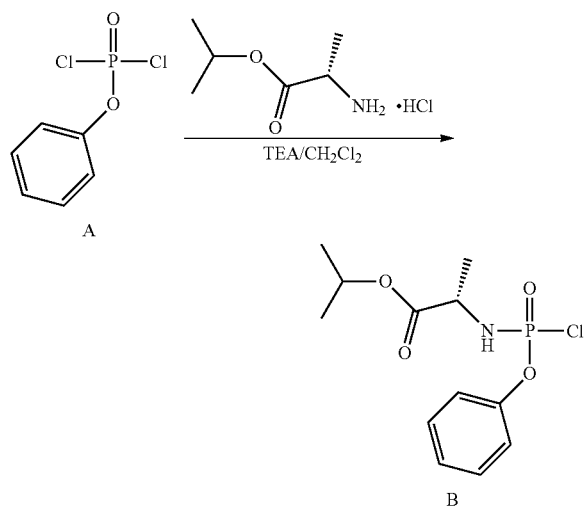

A

B

Compound A (commercially available, 4.99 g, 23.8 mmol) was dissolved in dichloromethane (100 mL) and alanine isopropyl ester hydrochloride (3.98 g, 23.8 mmol) was added. The resulting clear solution was cooled −78° C. for 30 min. Triethylamine (6.63 mL, 47.5 mmol) was added dropwise over 15 min. The mixture was then allowed to warm to room temperature. After 16 h, the solvent was removed by argon stream. The residue was re-dissolved in MTBE (25 mL) and the insoluble was removed by filtration under argon. The filtrate was then condensed by argon stream and the crude product B was used for the next reaction without further purification. $^1$H NMR (300 MHz, CDCl$_3$): 7.1-7.4 (m, 5H), 5.1 (m, 1H), 4.35 (m, 1H), 4.15 (m, 1H), 1.5 (d, 3H), 1.2 (m, 6H). $^{31}$P NMR (121.4 MHz, CDCl$_3$): δ 7.8 and 8.4 (2 s).

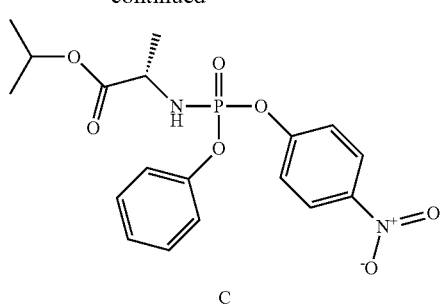

C

Alanine isopropyl ester hydrochloride (7.95 g, 47.4 mmol) was suspended in dichloromethane (100 mL). Compound A (10 g, 47.4 mmol) was added. Triethylamine (13.2 mL, 95 mmol) was then dropwise added over a period of 15 min. (internal reaction temperature; −10° C.~−3° C.). When the reaction was almost complete (by phosphorous NMR), p-nitrophenol (6.29 g, 45.0 mmol) was added as a solid in one portion. To the resulting slurry was added triethylamine (6.28 mL, 45 mmol) over a period of 15 min. The mixture was then warmed up to room temperature. When the reaction was complete, MTBE (100 mL) was added. The white precipitate was removed by filtration. The filter cake was washed with MTBE (3×50 mL). The filtrate and washings were combined and concentrated. The residue was purified by silica gel column chromatography (0 to 50% ethyl acetate/hexanes), affording compound C as a 1:1 ratio of diasteromeric mixture (14.1 g, 77%). $^1$H NMR (300 MHz, CDCl$_3$): δ 8.22 (2d, 2H), 7.2-7.4 (m, 7H), 5.0 (m, 1H), 4.09 (m, 1H), 3.96 (m, 1H), 1.39 (2d, 3H), 1.22 (m, 6H). MS=409.0 (M+H$^+$), 407.2 (M−H$^+$).

Separation of Two Diatereomers of Compound C

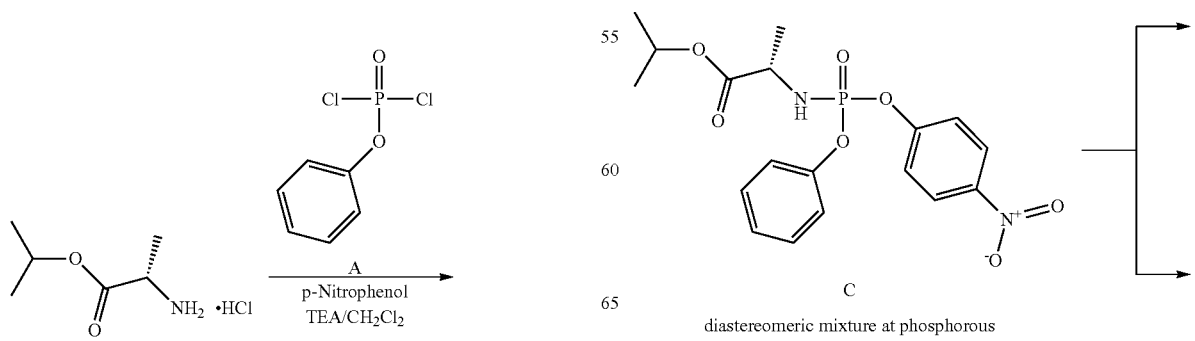

C diastereomeric mixture at phosphorous

-continued

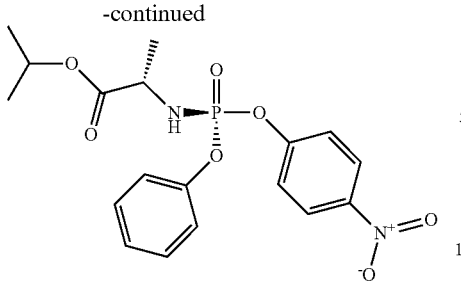

(S)-C

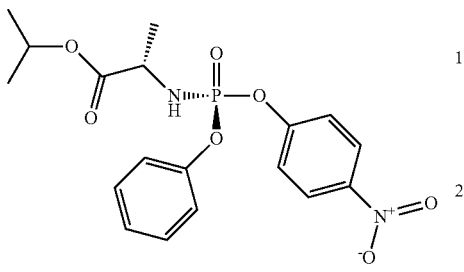

(R)-C

The two diastereomers were separated by chiral column chromatography under the following conditions;

Column: Chiralpak IC, 2×25 cm

Solvent system: 70% heptane and 30% isopropanol (IPA)

Flow rate: 6 mL/min.

Loading volume per run: 1.0 mL

Concentration of loading sample: 150 mg/mL in 70% heptane and 30% IPA (S)-compound C: retention time 43 min. $^{31}$P NMR (161.9 MHz, CDCl$_3$): δ −2.99 (s). (R)-compound C: retention time 62 min. $^{31}$P NMR (161.9 MHz, CDCl$_3$): δ −3.02 (s).

Alternatively, the two diasteromers were separated by crystallization under the following procedures;

Compound C was dissolved in diethyl ether (~10 mL/gram). While stirring, hexanes was then added until the solution became turbid. Seed crystals (~10 mg/gram of compound C) were added to promote crystallization. The resulting suspension was gently stirred for 16 h, cooled to ~0° C., stirred for an additional 2 h, and filtered to collect the crystalline material (recovery yield of the crystalline material 35%-35% The crystalline material contains ~95% of (S)-compound C and ~5% of (R)-compound C. Re-crystallization afforded 99% diastereomerically pure (S)-isomer.

Compound (S)-6

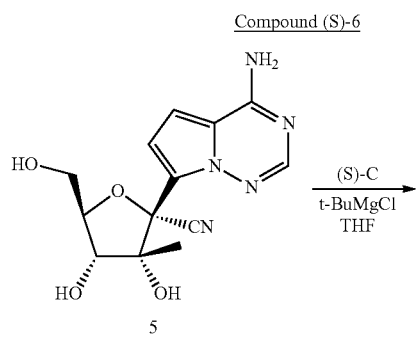

-continued

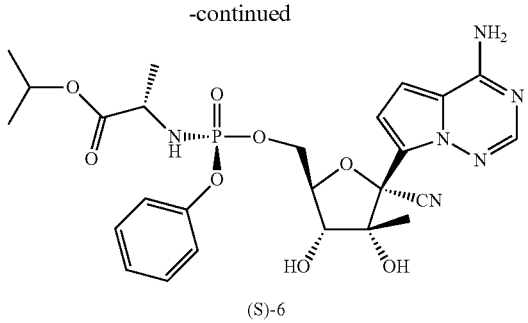

(S)-6

To a dry, argon purged round-bottom flask were added compound 5 (1.0 g, 3.28 mmol) and anhydrous THF (15 mL). The slurry was stirred for 10 min. and the flask was place in a water bath at room temperature. t-Butylmagnesium chloride in THF (1.0 M, 4.91 mL) was dropwise added, and the mixture was stirred for an additional 10 min. A solution of (S)-C (2.68 g, 6.55 mmol) in THF (10 mL) was then added. The flask was place in a heating oil bath pre-set at 50° C. and the mixture was stirred until compound 1 was almost consumed. After ~2.5 h, the reaction mixture was cooled to room temperature, and methanol (5 mL) was added. Solvents were removed under reduced pressure and the residue was purified by silica gel column chromatography (70% ethyl acetate/hexanes to remove less polar impurities, 10% methanol/dichloromethane to elute the product), affording (S)-6 as an off-white solid (1.45 g, 77%). $^1$H NMR (400 MHz, DMSO-d$_6$): δ 7.89 (s, 1H), 7.84 (brs, 2H), 7.36 (t, 2H), 7.23 (d, 2H), 7.17 (t, 1H), 6.87 (d, J=4.4 Hz, 1H), 6.74 (d, J=4.4 Hz, 1H), 6.02 (dd, 1H), 5.96 (s, 1H), 5.41 (d, 1H), 4.82 (m, 1H), 4.38 (dd, 1H), 4.22 (q, 1H), 4.16 (m, 1H), 3.81 (m, 1H), 3.67 (dd, 1H), 1.22 (d, 3H), 1.11 (dd, 6H), 0.89 (s, 3H). $^{31}$P NMR (161.9 MHz, DMSO-d$_6$): δ 3.99 (s). MS=575.0 (M+H$^+$), 572.7 (M−H$^+$).

Compound (S)-8

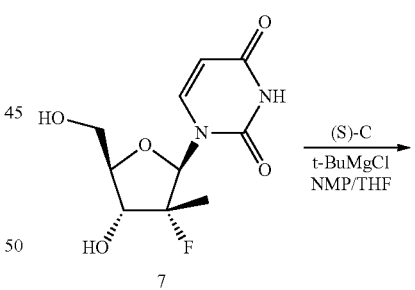

7

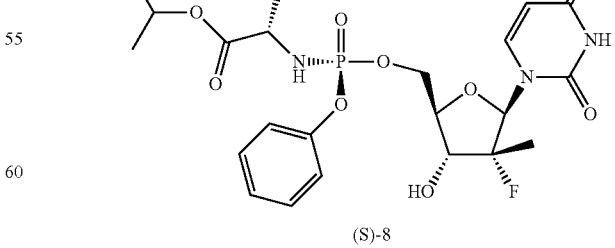

(S)-8

To a dry, argon purged round-bottom flask were added compound 7 (prepared according to J. Med. Chem., 2005, 48, 5504-5508, 100 mg, 0.38 mmol), anhydrous THF (3 mL) and anhydrous NMP (1 mL). The slurry was stirred for 10 min. and the flask was place in a water bath at room temperature. t-Butylmagnesium chloride in THF (1.0 M, 0.76 mL) was dropwise added, and the mixture was stirred for an additional 10 min. A solution of (S)-C (313 mg, 0.76 mmol) in THF (2 mL) was then added. The flask was place in a heating oil bath pre-set at 55° C. and the mixture was stirred until compound 7 was almost consumed. After ~2.5 h, the reaction mixture was cooled to room temperature, and methanol (1 mL) was added. Solvents were removed under reduced pressure and the residue was purified by RP-HPLC followed by silica gel column chromatography, affording (S)-8 (130 mg, 65%). $^1$H NMR (400 MHz, CDCl$_3$): δ 8.51 (brs, 1H), 7.46 (d, 1H), 7.2-7.4 (m, 5H), 6.28 (d, 1H), 5.70 (dd, 1H), 5.01 (m, 1H), 4.49 (m, 2H), 3.8-4.1 (m, 4H), 1.41 (d, 3H), 1.35 (d, 3H), 1.24 (d, 6H). $^{31}$P NMR (162.1 MHz, CDCl$_3$): δ 3.70 (s). MS=530.0 (M+H$^+$), 528.0 (M–H$^+$). Chiral HPLC retention time (Chiralpak AS-H, 250×4.6 mm 5 micron, 100% CH$_3$CN, 1 mL/min flow rate); 6.5 min vs. 5.2 min for the R-isomer).

Using the general procedures described for the preparation of Compound (S)-C or Compound (R)-C, Compounds 10-24 may be prepared.

Compound 10

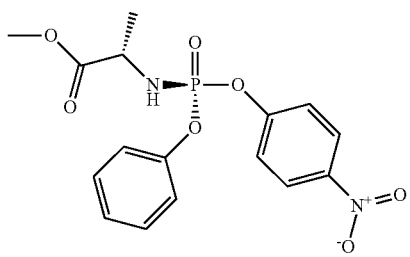

Compound 11

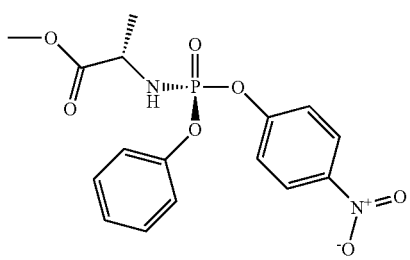

Compound 12

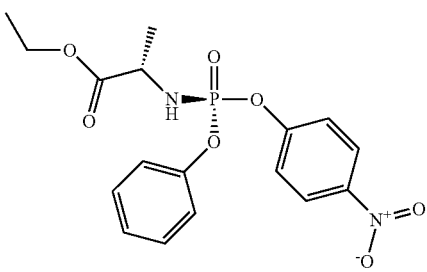

Compound 13

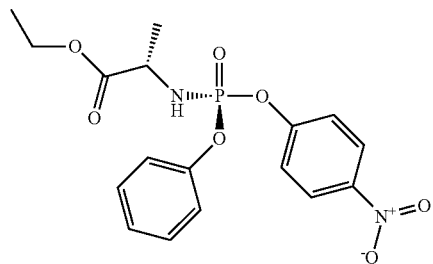

Compound 14

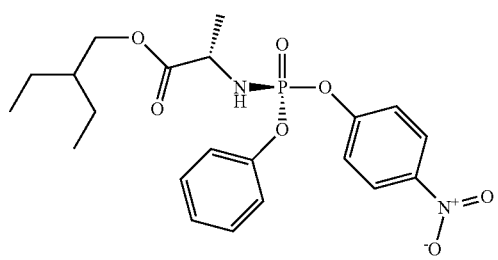

Compound 15

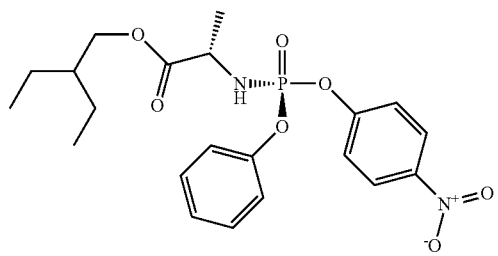

Compound 16

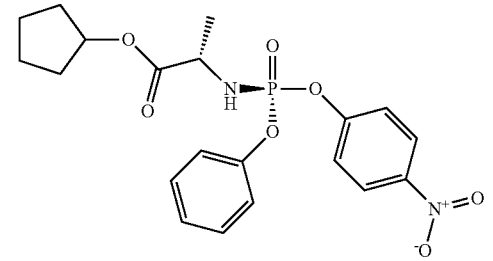

Compound 17

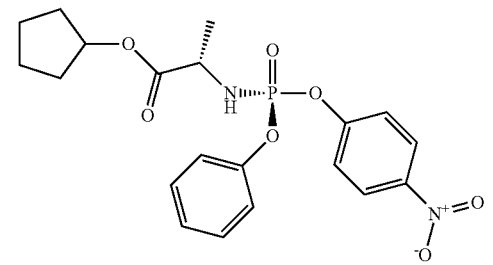

Compound 18
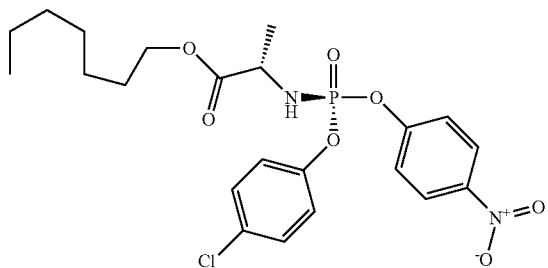
Compound 19
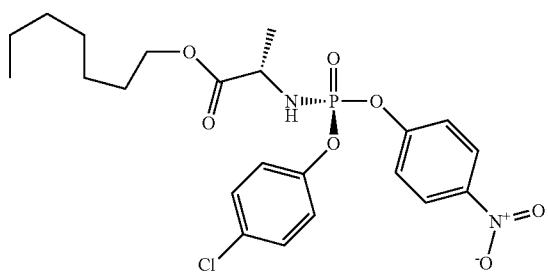
Compound 20
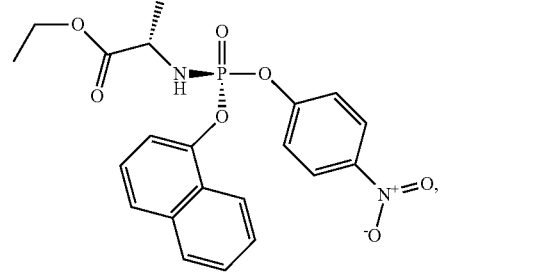
Compound 21
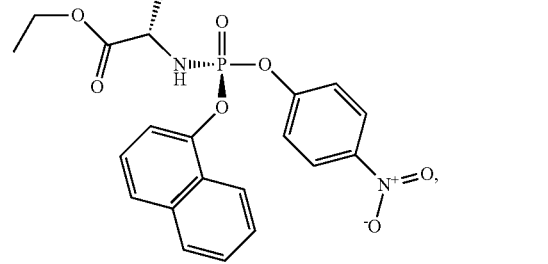
Compound 22
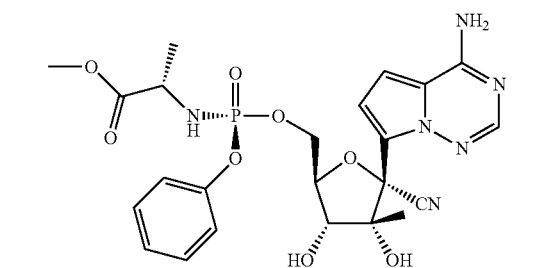
Compound 23
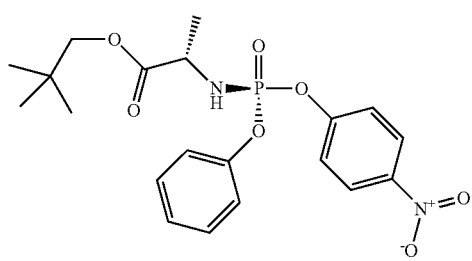
Compound 24
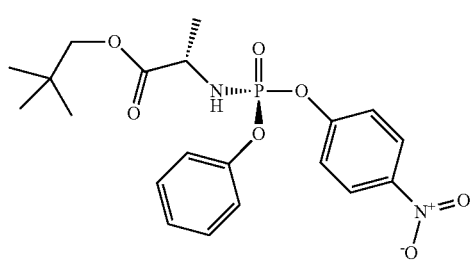
Using the general procedures described for the preparation of Compound (S)-6, Compounds 25-38 may be prepared using either Compound (S)-C or Compound (R)-C.
Compound 25
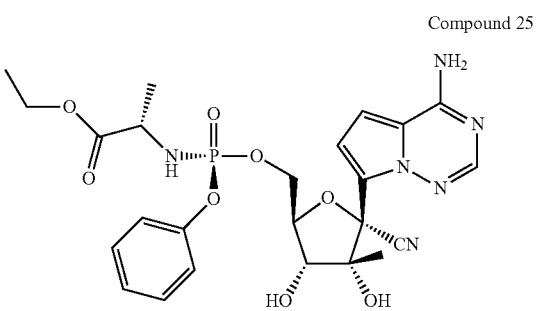
Compound 26
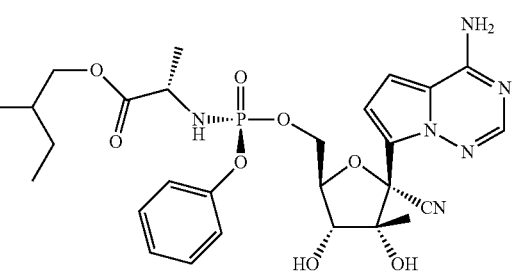
Compound 27
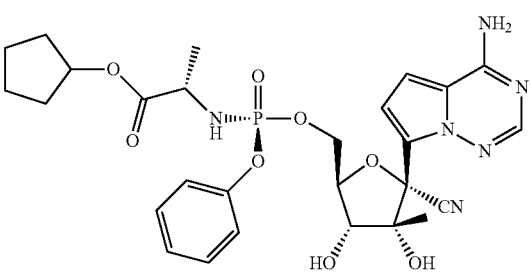

Compound 28
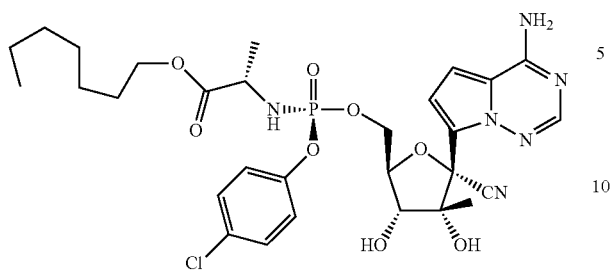
Compound 29
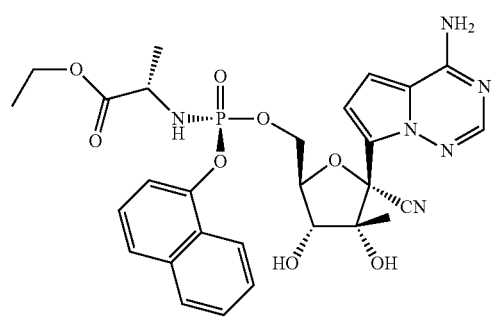
Compound 30
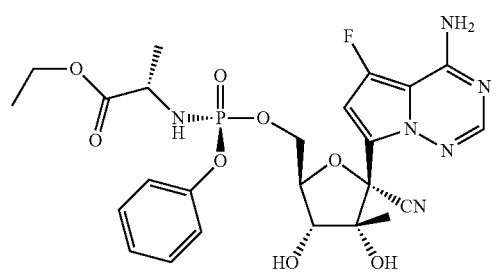
Compound 31
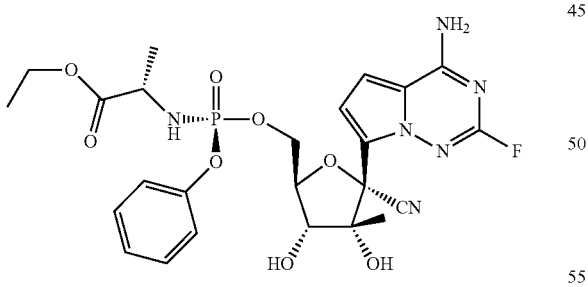
Compound 32
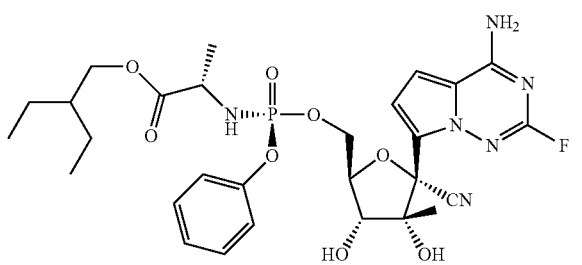
Compound 34
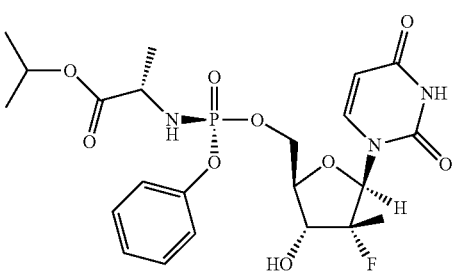
Compound 35
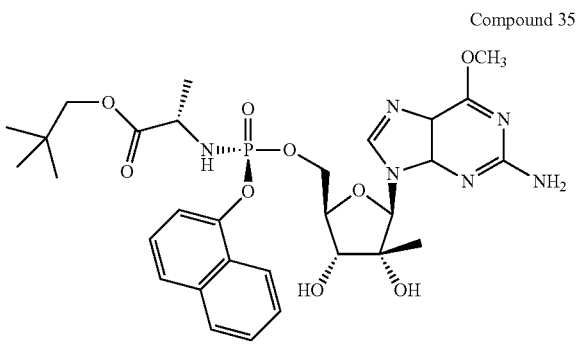
Compound 36
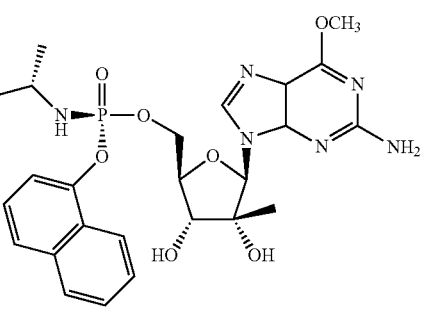
Compound 37
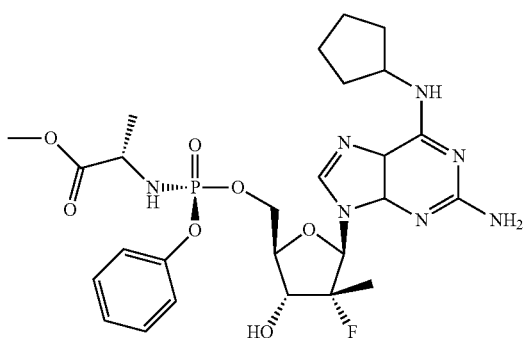

-continued

Compound 38

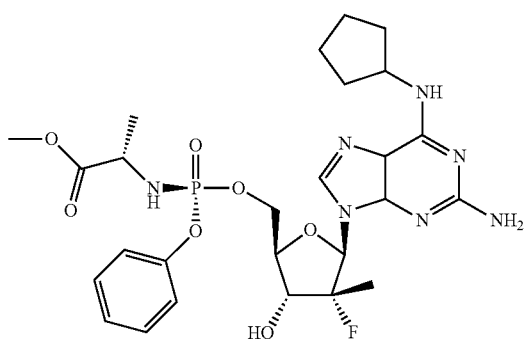

What is claimed is:

1. A method for preparing a compound of Formula Ia or Ib:

Formula Ia

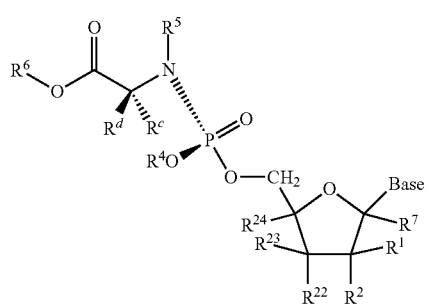

Formula Ib

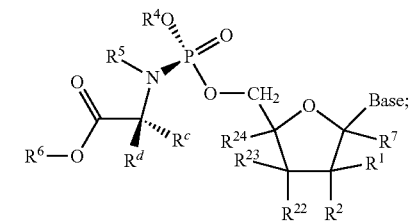

or a pharmaceutically acceptable salt or acid thereof; wherein:

each $R^1$, $R^2$, $R^7$, $R^{22}$, $R^{23}$ or $R^{24}$ is independently H, $OR^{11}$, $NR^{11}R^{12}$, $C(O)NR^{11}R^{12}$, —$OC(O)NR^{11}R^{12}$, $C(O)OR^{11}$, $OC(O)OR^{11}$, $S(O)_nR^a$, $S(O)_2NR^{11}R^{12}$, $N_3$, CN, halogen, $(C_1-C_8)$alkyl, $(C_3-C_8)$carbocyclyl, $(C_4-C_8)$carbocyclylalkyl, $(C_2-C_8)$alkenyl, $(C_2-C_8)$alkynyl or aryl $(C_1-C_8)$alkyl;

or any two $R^1$, $R^2$, $R^7$, $R^{22}$, $R^{23}$ or $R^{24}$ on adjacent carbon atoms when taken together are —O(CO)O— or —O(CR$^{11}$R$^{12}$)O— or when taken together with the ring carbon atoms to which they are attached form a double bond;

each Base is independently a naturally occurring or modified purine or pyrimidine base linked to the furanose ring through a carbon or nitrogen atom;

provided that Base is not uracil;

each n is independently 0, 1, or 2;

each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl provided that $R^c$ and $R^d$ are not the same;

each $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, —C(=O)$(C_1-C_8)$alkyl, —S(O)$_n$$(C_1-C_8)$ alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —NR$^a$—; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl $(C_1-C_8)$alkyl, heterocyclyl$(C_1-C_8)$alkyl, $(C_6-C_{20})$aryl, $(C_2-C_{20})$heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$;

said method comprising:

(a) providing a compound of Formula II

Formula II

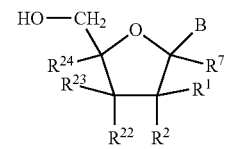

and (b) treating the compound of Formula II with a compound of Formula IIIa and a base Formula IIIa

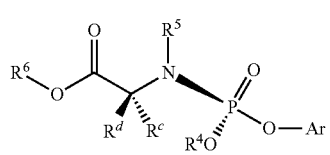

thereby forming a compound of Formula Ia or (c) treating the compound of Formula II with a compound of Formula IIIb and a base Formula IIIb

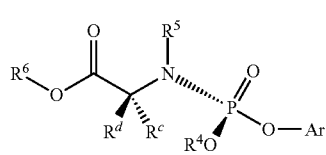

thereby forming a compound of Formula Ib;
wherein:

each Ar is a ($C_6$-$C_{20}$) aryl or heteroaryl wherein said ($C_6$-$C_{20}$) aryl or heteroaryl is substituted with one or more halogen, $NO_2$, or ($C_1$-$C_8$)haloalkyl and optionally substituted with with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$, the method further comprising a method of preparing a compound of Formula IIIa or Formula IIIb

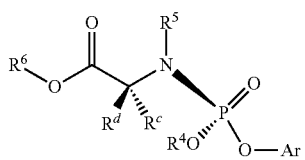

Formula IIIa

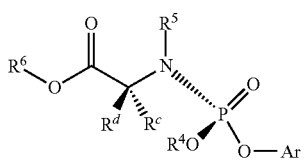

Formula IIIb wherein:

each $R^a$, $R^4$ or $R^6$ is independently ($C_1$-$C_8$)alkyl, ($C_2$-$C_8$) alkenyl, ($C_2$-$C_8$)alkynyl, ($C_3$-$C_8$)carbocyclyl, ($C_4$-$C_8$) carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl;

each $R^c$ or $R^d$ is independently H, ($C_1$-$C_8$)alkyl, ($C_2$-$C_8$) alkenyl, ($C_2$-$C_8$)alkynyl, ($C_3$-($C_8$)carbocyclyl, ($C_4$-$C_8$) carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl provided that $R^c$ and $R^d$ are not the same;

each $R^5$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl;

wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl ($C_1$-$C_8$)alkyl, heterocyclyl ($C_1$-$C_8$)alkyl, ($C_6$-$C_{20}$)aryl, ($C_2$-$C_{20}$)heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$ $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$ $S(O)_2N(R^a)_2$, $S(O)_2NH(R^a)$, $S(O)_2NH_2$, $OR^a$ or $R^a$; and each Ar is a ($C_6$-$C_{20}$) aryl or heteroaryl wherein said ($C_6$-$C_{20}$) aryl or heteroaryl is substituted with one or more halogen, $NO_2$, or ($C_1$-$C_8$)haloalkyl and optionally substituted with with one or more CN, $N_3$, $N(R^a)_2$ $C(O)N(R^a)_2$, $OC(O)N(R^a)_2$, $C(O)OR^a$, $OC(O)OR^a$, $C(O)R^a$, $OC(O)R^a$, $S(O)_n$ $R^a S(O)_2N(R^a)_2$, $OR^a$ or $R^a$ with the proviso that Ar is different from $R^4$;

said method comprising:

(d) providing a diastereomeric compound of Formula VIII

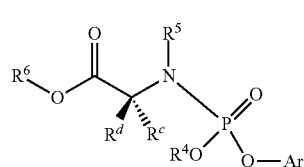

Formula VIII and (e) dissolving the compound of Formula VIII in a suitable solvent and inducing crystallization by addition of a $C_5$-$C_8$ hydrocarbon or $C_5$-$C_8$ cyclic hydrocarbon;

thereby forming a pure diasteromer of Formula IIIa or Formula IIIb.

2. The method of claim 1 wherein Formula Ia is Formula IVa, Formula Ib is Formula IVb and Formula II is Formula V:

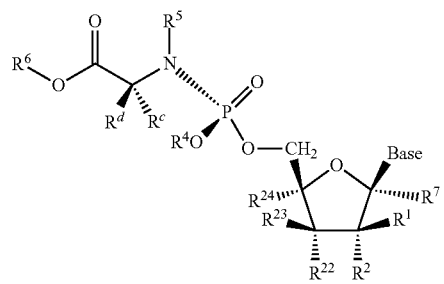

Formula IVa

Formula IVb

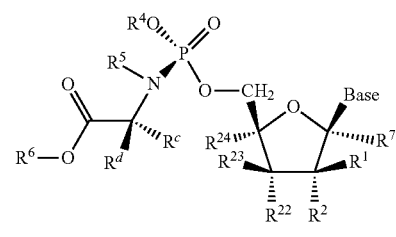

Formula V

3. The method of claim 1 wherein Base is selected from the group consisting of:

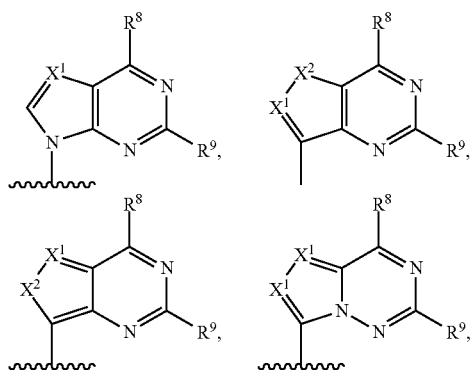

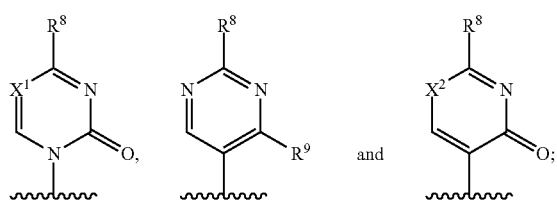

wherein:

each $X^1$ is independently N or $CR^{10}$;

each $X^2$ is independently $NR^{11}$, O, or $S(O)_n$;

each $R^8$ is independently halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, ($C_1$-$C_8$)alkyl, ($C_2$-$C_8$)alkenyl, ($C_2$-$C_8$)alkynyl, ($C_4$-$C_8$)carbocyclylalkyl, ($C_6$-$C_{20}$)aryl, ($C_2$-$C_{20}$)heterocyclyl, heteroaryl, —C(=O)($C_1$-$C_8$)alkyl, —S(O)$_n$($C_1$-$C_8$)alkyl, aryl($C_1$-$C_8$)alkyl, $OR^{11}$ or $SR^{11}$;

each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, $R^{11}$, $OR^{11}$ or $SR^{11}$;

each $R^{11}$ or $R^{12}$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl, heteroaryl, —C(=O)($C_1$-$C_8$)alkyl, —S(O)$_n$($C_1$-$C_8$)alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —$NR^a$—;

wherein each ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl of each $R^c$, $R^d$, $R^1$, $R^2$, $R^{22}$, $R^{23}$, $R^{24}$, $R^4$, $R^5$, $R^6$, $R^7$, $R^8$, $R^9$, $R^{10}$, $R^{11}$ or $R^{12}$ is, independently, optionally substituted with one or more halo, hydroxy, CN, $N_3$, $N(R^a)_2$, $NH(R^a)$, $NH_2$, $NO_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$; and provided that Base is not uracil.

4. The method of claim 3 wherein Base is selected from the group consisting of:

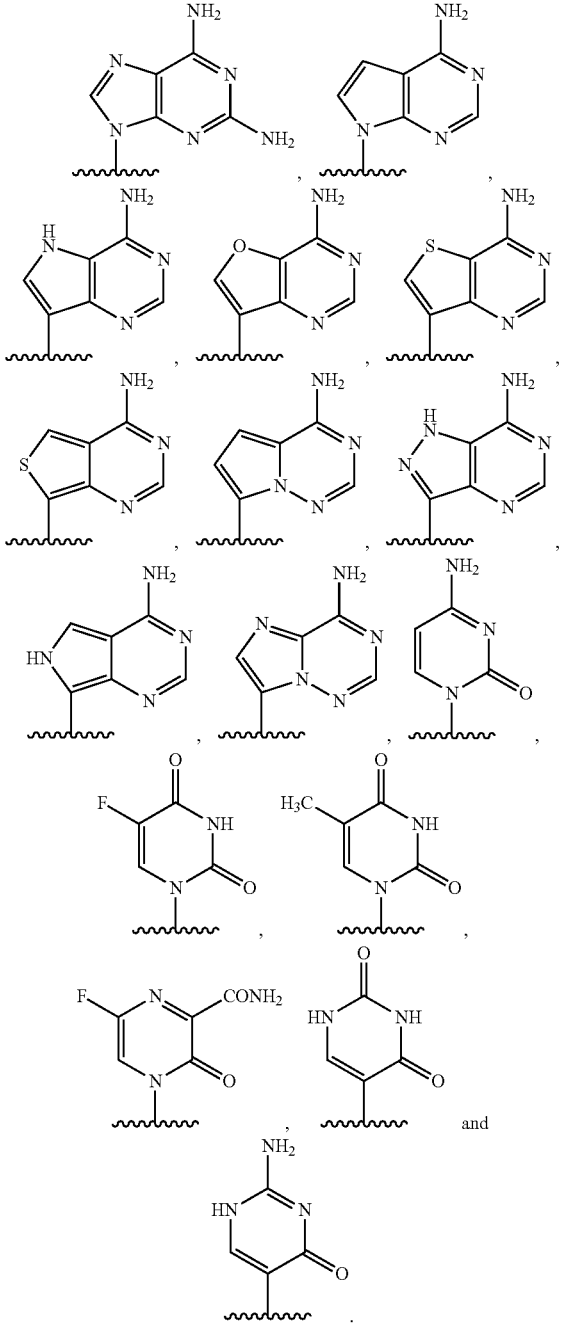

5. The method of claim 1 wherein Formula Ia is Formula VIa, Formula Ib is Formula VIb and Formula II is Formula VII:

Formula VIa

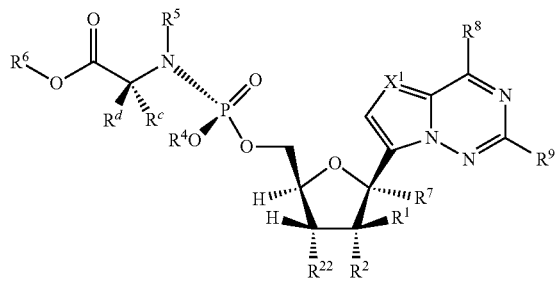

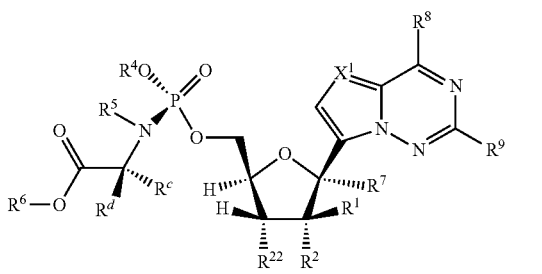

Formula VIb

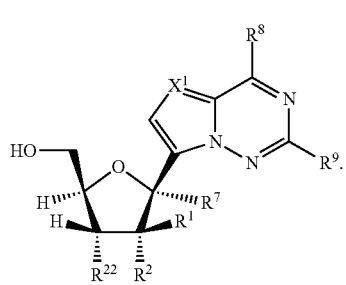

Formula VII

6. The method of claim 1 wherein Formula Ia is Formula XIa, Formula Ib is Formula XIb and Formula II is Formula XII:

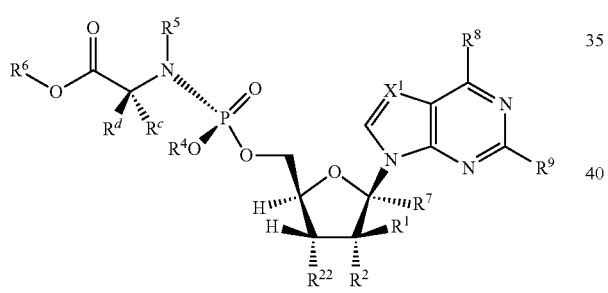

Formula XIa

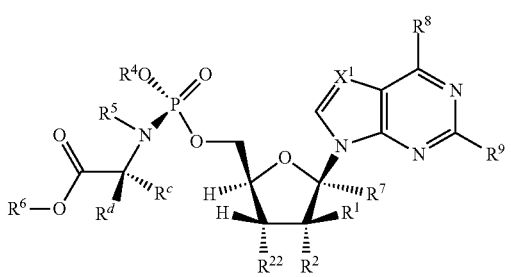

Formula XIb

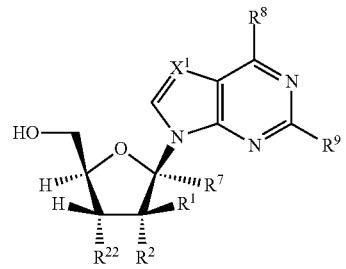

Formula XII wherein:
each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H; and
each $R^{22}$ is $OR^{11}$.

7. The method of claim 1 wherein Formula Ia is Formula XIIIa, Formula Ib is Formula XIIIb and Formula II is Formula XIV:

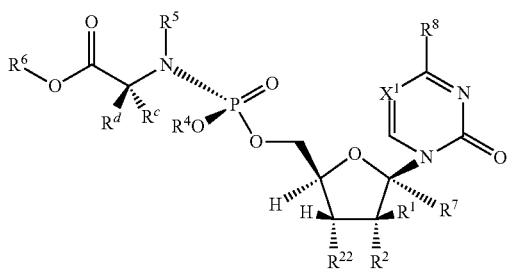

Formula XIIIa

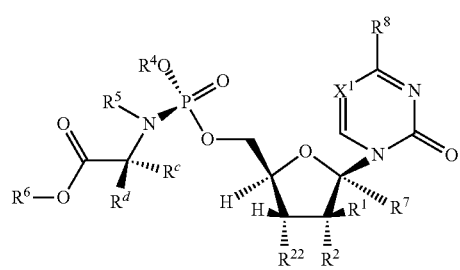

Formula XIIIb

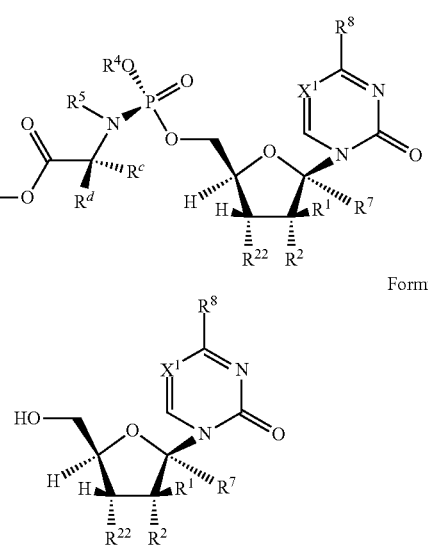

Formula XIV wherein:
each $R^1$ is independently H, halogen, optionally substituted $(C_1-C_8)$alkyl, optionally substituted $(C_2-C_8)$alkenyl or optionally substituted $(C_2-C_8)$alkynyl;
each $R^2$ is independently halogen or $OR^{11}$;
each $R^5$ is H; and
each $R^{22}$ is $OR^{11}$.

8. The method of claim 1 wherein $R^1$ is H, halogen, optionally substituted $(C_1-C_8)$alkyl, optionally substituted $(C_2-C_8)$alkenyl or optionally substituted $(C_2-C_8)$alkynyl.

9. The method of claim 8 wherein $R^1$ is H, $CH_3$ or F.

10. The method of claim 1 wherein each $R^5$, $R^{23}$ and $R^{24}$ is H.

11. The method of claim 1 wherein one of $R^c$ or $R^d$ is H and the other of $R^c$ or $R^d$ is optionally substituted $(C_1-C_8)$alkyl.

12. The method of claim 1 wherein $R^6$ is optionally substituted $(C_1-C_8)$alkyl.

13. The method of claim 1 wherein $R^8$ is $NR^{11}R^{12}$ or $OR^{11}$.

14. The method of claim 13 wherein $R^9$ is H or $NR^{11}R^{12}$.

15. The method of claim 1 wherein when $R^8$ or $R^9$ is $OR^{11}$ or $NR^{11}R^{12}$ then each $R^{11}$ and $R^{12}$ of said $OR^{11}$ or $NR^{11}R^{12}$ is H.

16. The method of claim 14 wherein $R^8$ is $NH_2$ and $R^9$ is H.

17. The method of claim 1 wherein $R^4$ is optionally substituted $(C_6\text{-}C_{20})$aryl.

18. The method of claim 1 wherein the compound of Formula VIII is dissolved in an ether solvent and the crystallization is induced by addition of a $C_5\text{-}C_8$ hydrocarbon.

19. The method of claim 1 wherein the compound of Formula VIII is dissolved in diethyl ether or methyl-t-butyl ether and crystallization is induced by the addition of hexane.

20. The method of claim 19 wherein the compound of Formula VIII is dissolved in diethyl ether and crystallization is induced by the addition of hexane.

21. The method of claim 1 further comprising a method of preparing a compound of Formula VIII

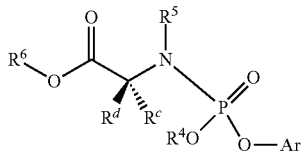

Formula VIII wherein:

each $R^a$, $R^4$ or $R^6$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

each $R^c$ or $R^d$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl provided that $R^c$ and $R^d$ are not the same;

each $R^5$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

wherein each $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a $(C_6\text{-}C_{20})$ aryl or heteroaryl wherein said $(C_6\text{-}C_{20})$ aryl or heteroaryl is substituted with one or more halogen, $NO_2$, or $(C_1\text{-}C_8)$haloalkyl and optionally substituted with with one or more CN, $N_3$, $N(R^a)_2$, $C(O)N(R^a)_2$, $OC(O)N(R^a)_2$, $C(O)OR^a$, $OC(O)OR^a$, $C(O)R^a$, $OC(O)R^a$, $S(O)_nR^a$, $S(O)_2N(R^a)_2$, $OR^a$ or $R^a$ with the proviso that Ar is different from $R^4$;

said method comprising:

(f) providing a chirally pure amino acid ester of Formula IX or a salt thereof

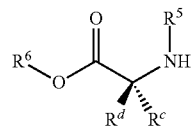

Formula IX (g) treating the compound of Formula IX with a compound of Formula X in the presence of a base

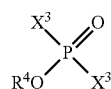

Formula X wherein each $X^3$ is halogen; and (h) treating the resulting mixture with ArOH;

thereby forming a compound of Formula VIII.

22. A method of preparing a compound of Formula IIIa or Formula IIIb

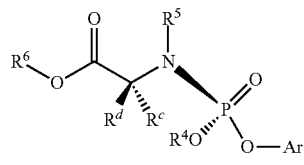

Formula IIIa

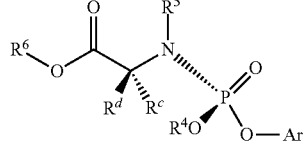

Formula IIIb or a salt or ester thereof, wherein:

each $R^a$, $R^4$ or $R^6$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

each $R^c$ or $R^d$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl provided that $R^c$ and $R^d$ are not the same;

each $R^5$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

wherein each $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl of each $R^c$, $R^d$, $R^4$, $R^5$ or $R^6$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$; and each Ar is a $(C_6\text{-}C_{20})$ aryl or heteroaryl wherein said $(C_6\text{-}C_{20})$ aryl or heteroaryl is substituted with one or more halogen, NO$_2$, or (C$_1$-C$_8$)haloalkyl and optionally substituted with with one or more CN, N$_3$, N(R$^a$)$_2$, C(O)N(R$^a$)$_2$, OC(O)N(R$^a$)$_2$, C(O)OR$^a$, OC(O)OR$^a$, C(O)R$^a$, OC(O)R$^a$, S(O)$_n$R$^a$, S(O)$_2$N(R$^a$)$_2$, OR$^a$ or R$^a$ with the proviso that Ar is different from R$^4$;

said method comprising:

(d) providing a diastereomeric compound of Formula VIII

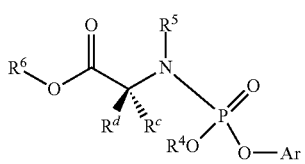

Formula VIII and (e) dissolving the compound of Formula VIII in a suitable solvent and inducing crystallization by addition of a C$_5$-C$_8$ hydrocarbon or C$_5$-C$_8$ cyclic hydrocarbon;

thereby forming a pure diasteromer of Formula IIIa or Formula IIIb.

23. The method of claim 22 wherein the compound of Formula VIII is dissolved in an ether solvent and the crystallization is induced by addition of a C$_5$-C$_8$ hydrocarbon.

24. The method of claim 23 wherein the compound of Formula VIII is dissolved in diethyl ether or methyl-t-butyl ether and crystallization is induced by the addition of hexane.

25. The method of claim 24 wherein the compound of Formula VIII is dissolved in diethyl ether and crystallization is induced by the addition of hexane.

26. The method of claim 22 further comprising a method of preparing a compound of Formula VIII

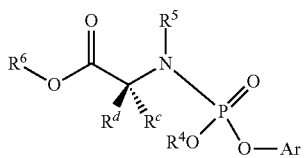

Formula VIII or a salt or ester thereof, wherein each R$^a$, R$^4$ or R$^6$ is independently (C$_1$-C$_8$)alkyl, (C$_2$-C$_8$)alkenyl, (C$_2$-C$_8$)alkynyl, (C$_3$-C$_8$)carbocyclyl, (C$_4$-C$_8$)carbocyclylalkyl, aryl(C$_1$-C$_8$)alkyl, heterocyclyl(C$_1$-C$_8$)alkyl, (C$_6$-C$_{20}$)aryl, (C$_2$-C$_{20}$)heterocyclyl or heteroaryl;

each R$^c$ or R$^d$ is independently H, (C$_1$-C$_8$)alkyl, (C$_2$-C$_8$)alkenyl, (C$_2$-C$_8$)alkynyl, (C$_3$-C$_8$)carbocyclyl, (C$_4$-C$_8$)carbocyclylalkyl, aryl(C$_1$-C$_8$)alkyl, heterocyclyl(C$_1$-C$_8$)alkyl, (C$_6$-C$_{20}$)aryl, (C$_2$-C$_{20}$)heterocyclyl or heteroaryl provided that R$^c$ and R$^d$ are not the same;

each R$^5$ is independently H, (C$_1$-C$_8$)alkyl, (C$_2$-C$_8$)alkenyl, (C$_2$-C$_8$)alkynyl, (C$_3$-C$_8$)carbocyclyl, (C$_4$-C$_8$)carbocyclylalkyl, aryl(C$_1$-C$_8$)alkyl, heterocyclyl(C$_1$-C$_8$)alkyl, (C$_6$-C$_{20}$)aryl, (C$_2$-C$_{20}$)heterocyclyl or heteroaryl;

wherein each (C$_1$-C$_8$)alkyl, (C$_2$-C$_8$)alkenyl, (C$_2$-C$_8$)alkynyl, (C$_3$-C$_8$)carbocyclyl, (C$_4$-C$_8$)carbocyclylalkyl, aryl(C$_1$-C$_8$)alkyl, heterocyclyl(C$_1$-C$_8$)alkyl, (C$_6$-C$_{20}$)aryl, (C$_2$-C$_{20}$)heterocyclyl or heteroaryl of each R$^c$, R$^d$, R$^4$, R$^5$ or R$^6$ is, independently, optionally substituted with one or more halo, hydroxy, CN, N$_3$, N(R$^a$)$_2$, NH(R$^a$), NH$_2$, C(O)N(R$^a$)$_2$, C(O)NH(R$^a$), C(O)NH$_2$, OC(O)N(R$^a$)$_2$, OC(O)NH(R$^a$), OC(O)NH$_2$, C(O)OR$^a$, OC(O)OR$^a$, S(O)$_n$R$^a$, S(O)$_2$N(R$^a$)$_2$, S(O)$_2$NH(R$^a$), S(O)$_2$NH$_2$, OR$^a$ or R$^a$; and each Ar is a (C$_6$-C$_{20}$) aryl or heteroaryl wherein said (C$_6$-C$_{20}$) aryl or heteroaryl is substituted with one or more halogen, NO$_2$, or (C$_1$-C$_8$)haloalkyl and optionally substituted with with one or more CN, N$_3$, N(R$^a$)$_2$, C(O)N(R$^a$)$_2$, OC(O)N(R$^a$)$_2$, C(O)OR$^a$, OC(O)OR$^a$, C(O)R$^a$, OC(O)R$^a$, S(O)$_n$R$^a$, S(O)$_2$N(R$^a$)$_2$, OR$^a$ or R$^a$ with the proviso that Ar is different from R$^4$;

said method comprising:

(f) providing a chirally pure amino acid ester of Formula IX or a salt thereof

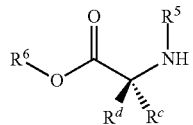

Formula IX (g) treating the compound of Formula IX with a compound of Formula X in the presence of a base

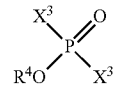

Formula X wherein each X$^3$ is halogen; and (h) treating the resulting mixture with ArOH;

thereby forming a compound of Formula VIII.

27. The method of claim 22 wherein R$^5$ is H and one of R$^c$ or R$^d$ is H.

28. The method of claim 22 wherein R$^6$ is optionally substituted (C$_1$-C$_8$)alkyl and R$^4$ is optionally substituted (C$_6$-C$_{20}$)aryl.

29. The method of claim 22 wherein R$^4$ is optionally substituted phenyl.

30. The method of claim 22 wherein one of R$^c$ or R$^d$ is H and the other of R$^c$ or R$^d$ is CH$_3$.

31. The method of claim 22 wherein Ar is optionally substituted para-nitrophenyl.

32. The method of claim 22 wherein the chirality at the carbon directly attached to R$^c$ and R$^d$ is S.

33. The method of claim 22 wherein the chirality at the carbon directly attached to R$^c$ and R$^d$ is R.

34. The method of claim 22 wherein the compound is selected from the group consisting of

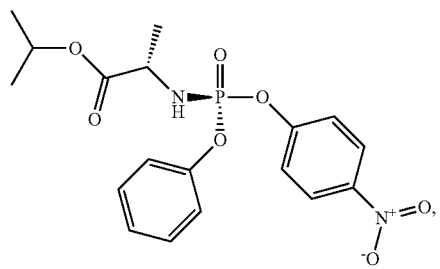

-continued
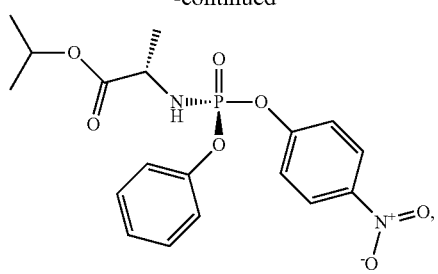
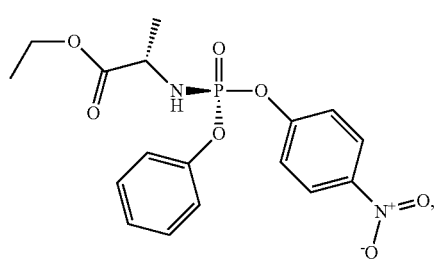
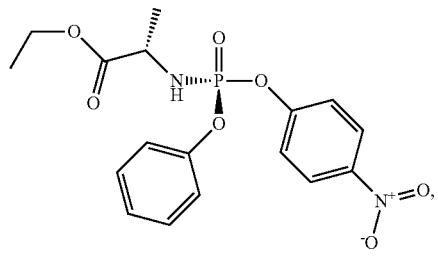
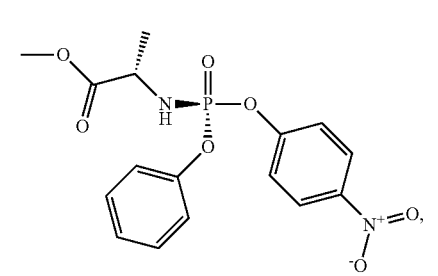
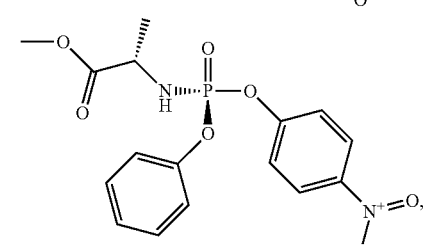
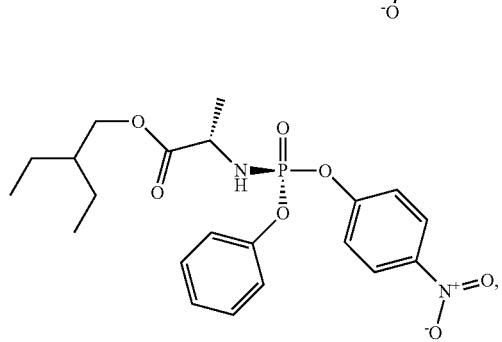
-continued
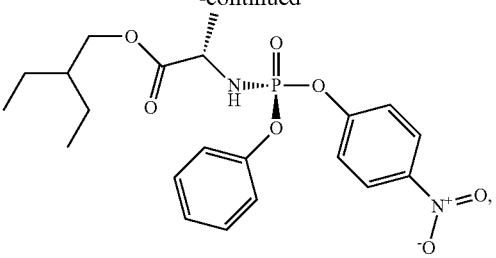
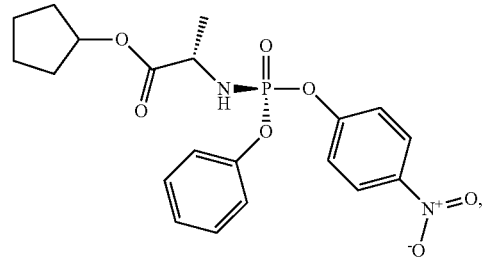
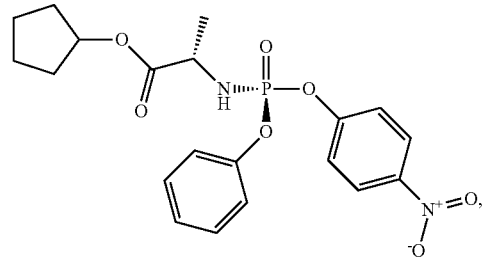
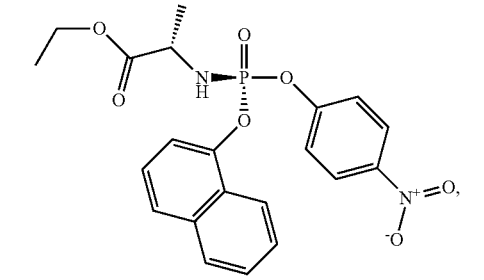
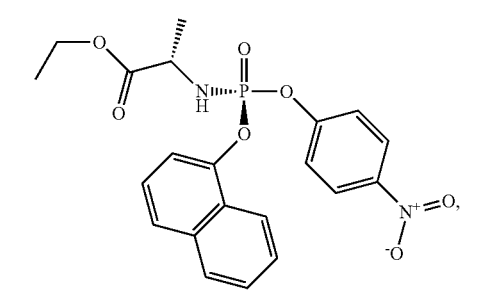
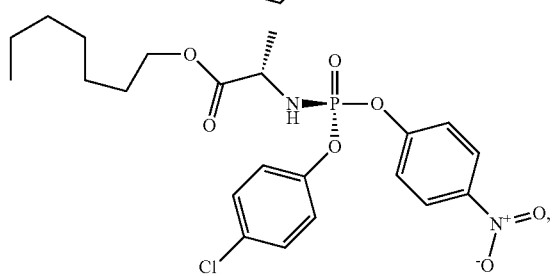

-continued
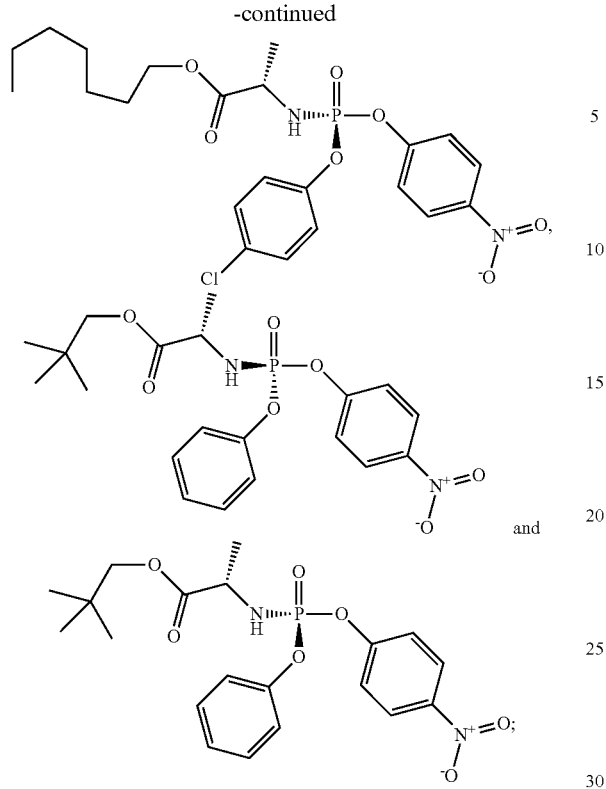
or salts or esters thereof.
* * * * *